US009879020B2

(12) United States Patent
Stafford et al.

(10) Patent No.: US 9,879,020 B2
(45) Date of Patent: Jan. 30, 2018

(54) GABAA AGONISTS AND METHODS OF USING TO CONTROL AIRWAY HYPERRESPONSIVENESS AND INFLAMMATION IN ASTHMA

(71) Applicants: UWM Research Foundation, Inc., Milwaukee, WI (US); The Trustees of Columbia University in the City of New York, New York, NY (US)

(72) Inventors: Douglas C. Stafford, Fitchburg, WI (US); James M. Cook, Whitefish Bay, WI (US); Alexander E. Arnold, Milwaukee, WI (US); Charles W. Emala, Woodcliff Lake, NJ (US); George Gallos, Tenafly, NJ (US); Michael Rajesh Stephen, Milwaukee, WI (US)

(73) Assignees: UWM Research Foundation, Inc., Milwaukee, WI (US); The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 14/429,808

(22) PCT Filed: Sep. 20, 2013

(86) PCT No.: PCT/US2013/060859
§ 371 (c)(1),
(2) Date: Mar. 20, 2015

(87) PCT Pub. No.: WO2014/047413
PCT Pub. Date: Mar. 27, 2014

(65) Prior Publication Data
US 2015/0232473 A1 Aug. 20, 2015

Related U.S. Application Data

(60) Provisional application No. 61/703,902, filed on Sep. 21, 2012.

(51) Int. Cl.
| | | |
|---|---|---|
| *C07D 487/04* | (2006.01) | |
| *C07D 487/14* | (2006.01) | |
| *C07D 487/22* | (2006.01) | |

(52) U.S. Cl.
CPC .................. *C07D 487/22* (2013.01)

(58) Field of Classification Search
CPC ............................ C07D 487/04; C07D 487/14
See application file for complete search history.

(56) References Cited

U.S. PATENT DOCUMENTS

| | | | |
|---|---|---|---|
| 6,743,789 B2 * | 6/2004 | Masciadri ............ | C07D 487/14 514/219 |
| 7,119,196 B2 | 10/2006 | Cook et al. | |
| 7,595,395 B2 | 9/2009 | Cook et al. | |
| 7,618,958 B2 | 11/2009 | Cook et al. | |
| 2007/0049580 A1 | 3/2007 | Cook et al. | |
| 2007/0166251 A1 | 7/2007 | Dayan et al. | |
| 2008/0152894 A1 | 6/2008 | Beihoffer et al. | |
| 2009/0306212 A1 | 12/2009 | Polak et al. | |
| 2010/0317619 A1 | 12/2010 | Cook et al. | |
| 2011/0224278 A1 | 9/2011 | Carmichael et al. | |

FOREIGN PATENT DOCUMENTS

| | | |
|---|---|---|
| CA | 1266671 | 3/1990 |
| CA | 2606658 | 4/2008 |
| EP | 2298296 | 3/2011 |
| WO | WO 2005063248 | 7/2005 |
| WO | WO 2005063297 | 7/2005 |
| WO | WO 2006036557 | 4/2006 |
| WO | WO 2006078399 | 7/2006 |
| WO | WO 2008013757 | 1/2008 |
| WO | 2008055932 | 5/2008 |
| WO | WO 2008060778 | 5/2008 |
| WO | 2008073257 | 6/2008 |
| WO | WO 2008079806 | 7/2008 |
| WO | 2008130314 | 10/2008 |
| WO | WO 2011024115 | 3/2011 |
| WO | WO 2011042550 | 4/2011 |
| WO | WO 2011153377 | 8/2011 |
| WO | WO 2012051707 | 4/2012 |
| WO | WO 2012068161 | 5/2012 |

OTHER PUBLICATIONS

Abraham, R.T. et al., "Jurkat T Cells and Development of the T-Cell Receptor Signalling Paradigm," Nature Reviews Immunology, vol. 4, pp. 301-308 (2004).
Akinbami, L.J. et al., "Asthma Prevalence, Health Care Use, and Mortality: United States, 2005-2009," National Heath Statistics Reports, vol. 32, pp. 1-14 (2011).
Alam, S. et al., "Human Peripheral Blood Mononuclear Cells Express GABAA Receptor Subunits," Molecular Immunology, vol. 43, pp. 1432-1442 (2006).
Allen, M.S. et al., "Synthesis of Novel 2-Phenyl-2H-pyrazolo[4,3-c] isoquinolin-3-ols: Topological Comparisons with Analogues of 2-Phenyl-2,5-dihydropyrazolo[4,3-c] quinolin-3(3H)-ones at Benzodiazepine Receptors," Journal of Medicinal Chemistry, vol. 35, pp. 368-374 (1992).
Arnold, L.A. et al., "Inhibitors of the Interaction of a Thyroid Hormone Receptor and Coactivators: Preliminary Structure—Activity Relationships," Journal of Medicinal Chemistry, vol. 50, pp. 5269-5280 (2007).

(Continued)

*Primary Examiner* — Bruck Kifle
(74) *Attorney, Agent, or Firm* — Michael Best & Friedrich LLP

(57) ABSTRACT

Novel methods of treating inflammation and airway constriction using GABAergic compounds with reduced benzodiazepine-like CNS activity are provided. Novel compounds which selectively target alpha-4 and alpha-5 $GABA_A$ receptors and methods of using those compounds to treat bronchoconstriction and inflammation are provided herein.

10 Claims, 26 Drawing Sheets

(56) References Cited

OTHER PUBLICATIONS

Ator, N.A. et al., "Reducing Abuse Liability of GABAA/Benzodiazepine Ligands via Selective Partial Agonist Efficacy at $\alpha_1$ and $\alpha_{2/3}$ Subtypes," The Journal of Pharmacology and Experimental Therapeutics, vol. 332, pp. 4-16 (2010).

Bates, J.H.T. et al., "Animal Models of Asthma," American Journal of Physiology Lung Cellular and Molecular Physiology, vol. 297, pp. L401-L410 (2009).

Bhat, R. et al., "Inhibitory Role for Gaba in Autoimmune Inflammation," Proceedings of the National Academy of Sciences of the United States of America, vol. 107, pp. 2580-2585 (2010).

Bibolini, M.J. et al., "Inhibitory Role of Diazepam on Autoimmune Inflammation in Rats with Experimental Autoimmune Encephalomyelitis," Neuroscience, vol. 199, 421-428 (2011).

Bjurström, H. et al., "GABA, a Natural Immunomodulator of T Lymphocytes," Journal of Neuroimmunology, vol. 205, pp. 44-50 (2008).

Boulet, L., "Perception of the Role and Potential Side Effects of Inhaled Corticosteroids Among Asthmatic Patients," Chest, vol. 113, pp. 587-592 (1998).

Cain, M. et al., "Beta-Carbolines: Synthesis and Neurochemical and Pharmacological Actions on Brain Benzodiazepine Receptors," Journal of Medicinal Chemistry, vol. 25, pp. 1081-1091 (1982).

Centers for Disease Control and Prevention, "Asthma in the US Growing Every Year," Vital Signs, pp. 1-4 (2011).

Chandra, D. et al., "$GABA_A$ Receptor $\alpha 4$ Subunits Mediate Extrasynaptic Inhibition in Thalamus and Dentate Gyrus and the Action of Gaboxadol," Proceedings of the National Academy of Sciences of the United States of America, vol. 103, pp. 15230-15235 (2006).

Chen, Q. et al., "Comparison of Cell Expression Formats for the Characterization of $GABA_A$ Channels Using a Microfluidic Patch Clamp System," ASSAY and Drug Development Technologies, vol. 10, pp. 325-335 (2012).

Clayton, T. et al., "An Updated Unified Pharmacophore Model of the Benzodiazepine Binding Site on $\gamma$-Aminobutyric Acid$_a$ Receptors: Correlation with Comparative Models," Current Medicinal Chemistry, vol. 14, pp. 2755-2775 (2007).

Clayton, T.S., "Part I. Unified Pharmacophore Protein Models of the Benzodiazepine Receptor Subtypes. Part II. Subtype Selective Ligands for $\alpha 5$ GABA(A)/BZ Receptors," PhD Dissertation, Department of Chemistry and Biochemistry, University of Wisconsin-Milwaukee, pp. i-xliv, 1-776 (2011).

Diaz-Arauzo, H. et al., "Synthetic and Computer Assisted Analysis of the Pharmacophore for Agonists at Benzodiazepine Receptors," Life Sciences, vol. 49, pp. 207-216 (1991).

Dionisio, L. et al., "An Intrinsic GABAergic System in Human Lymphocytes," Neuropharmacology, vol. 60, pp. 513-519 (2011).

Edwankar, R.V., "Part I. HZ166, A Novel $\gamma$-aminobutyric Acid (A) Receptor Subtype-selective Ligand Active Against Neuropathic Pain. Part II. The First Enantiospecific, Stereospecific Total Synthesis of the C-19 Methyl Substituted Sarpagine Indole Alkaloids 19(S), 20(R)-dihydroperaksine, 19(S),20(R)-dihydroperaksine-17-al and Peraksine. Part III. Application of Metal-carbenoid Chemistry adn Bronsted Acid Mediated Cyclization of Enaminones for the Rapid and Efficient Access to teh Tetracyclic (Abce) Skeleton of the Strychnos Alkaloids Contained in Bisindole Alkaloids," PhD Dissertation, Department of Chemistry and Biochemistry, University of Wisconsin-Milwaukee, pp. i-xix, 1-436 (2010).

Fischer, B.D. et al., "Anxiolytic-like Effects of 8-acetylene Imidazobenzodiazepines in a Rhesus Monkey Conflict Procedure," Neuropharmacology, vol. 59, pp. 612-618 (2010).

Gallos, G. et al., "Targeting the Restricted $\alpha$-subunit Repertoire of Airway Smooth Muscle $GABA_A$ Receptors Augments Airway Smooth Muscle Relaxation," American Journal of Physiology Lung Cellular and Molecular Physiology, vol. 302, pp. L248-L256 (2012).

Girodet, P.-O. et al., "Airway Remodeling in Asthma: New Mechanisms and Potential for Pharmacological Intervention," Pharmacology & Therapeutics, vol. 130, pp. 325-337 (2011).

Golden, A.P. et al., "IonFlux: A Microfluidic Patch Clamp System Evaluated with Human Ether-à-go-go Related Gene Cahnnel Physiology and Pharmacology," ASSAY and Drug Development Technologies, vol. 9, pp. 608-619 (2011).

Gonda, I., "Systemic Delivery of Drugs to Humans via Inhalation," Journal of Aerosol Medicine, vol. 19, pp. 47-53 (2006).

Gundavarapu, S. et al., "Role of Nicotinic Receptors and Acetylcholine in Mucous Cell Metaplasia, Hyperplasia and Airway Mucus Formation in vitro and in vivo," Journal of Allergy and Clinical Immunology, vol. 130, pp. 770-780 (2012).

Hakonarson, H. et al., "Bi-Directional Activation Between Human Airway Smooth Muscle Cells and T Lymphocytes: Role in Induction of Altered Airway Responsiveness," The Journal of Immunology, vol. 166, pp. 293-303 (2001).

Han, D. et al., "A Study of the Structure-activity Relationship of $GABA_A$-benzodiazepine Receptor Bivalent Ligands by Conformational Analysis with Low Temperature NMR and X-ray Analysis," Bioorganic and Medicinal Chemistry, vol. 16, pp. 8853-8862 (2008).

Harvey, S.C. et al., "The $GABA_A$ Receptor $\alpha 1$ Subtype in the Ventral Pallidum Regulates Alcohol-Seeking Behaviors," The Journal of Neuroscience, vol. 22, pp. 3765-3775 (2002).

He, X. et al., "Pharmacophore/Receptor Models for $GABA_A$/BzR $\alpha 2\beta 3\gamma 2$, $\alpha 3\beta 3\gamma 2$, $\alpha 4\beta 3\gamma 2$ Recombinant Subtypes. Included Volume Analysis and Comparison to $\alpha 1\beta 3\gamma 2$, $\alpha 5\beta 3\gamma 2$ and $\alpha 6\beta 3\gamma 2$ Subtypes," Drug Design and Discovery, vol. 17, pp. 131-171 (2000).

He, X., "Studies of Molecular Pharmacophore/receptor Models for $GABA_A$/BzR Subtypes: Chemical and Computer Assisted Approach in Search of Selective Ligands for $GABA_A$/BzR Subtypes," PhD Dissertation, Department of Chemistry and Biochemistry, University of Wisconsin-Milwaukee, pp. i-xviii, 1-300 (2000).

Hirota, J.A. et al., "Modeling Asthma in Mice—What Have We Learned about the Airway Epithelium," American Journal of Respiratory Cell and Molecular Biology, vol. 44, pp. 431-438 (2011).

Huang, Q. et al., "Benzo-fused Benzodiazepines Employed as Topological Probes for the Study of Benzodiazepine Receptor Subtypes," Medicinal Chemistry Research, vol. 6, pp. 384-391 (1996).

Huang, Q. et al., "Pharmacophore/Receptor Models for $GABA_A$/BzR Subtypes ($\alpha 1\beta 3\gamma 2$, $\alpha 5\beta 3\gamma 2$, and $\alpha 6\beta 3\gamma 2$) via a Comprehensive Ligand-Mapping Approach," Journal of Medicinal Chemistry, vol. 43, pp. 71-95 (2000).

Huang, Q. et al., "Predictive Models for $GABA_A$/Benzodiazepine Receptor Subtypes: Studies of Quantitative Structure—Activity Relationships for Imidazobenzodiazepines at Five Recombinant $GABA_A$/Benzodiazepine Receptor Subtypes $[\alpha\chi\beta 3\gamma 2$ ($\chi$ = 1-3, 5, and 6)] via Comparative Molecular Field Analysis," Journal of Medicinal Chemistry, vol. 41, pp. 4130-4142 (1998).

Jonas, D.E. et al., "Drug Class Review, Controller Medications for Asthma, Final Update 1 Report," Oregon Health & Science University, pp. 1-26 (2011).

Khelef, N. et al., "Characterization of Murine Lung Inflammation After Infection with Parenteral *Bordetella pertussis* and Mutants Deficient in Adhesions or Toxins," Infection and Immunity, vol. 62, pp. 2893-2900 (1994).

Koziol-White, C.J. et al., "Airway Smooth Muscle and Immunomodulation in Acute Exacerbations of Airway Disease," Immunological Reviews, vol. 242, pp. 178-185 (2011).

Kubin, M. et al., "Differential Regulation of Interleukin-12 (IL-12), Tumor Necrosis Factor $\alpha$, and IL-1$\beta$ Production in Human Myeloid Leukemia Cell Lines and Peripheral Blood Mononuclear Cells," Blood, vol. 83, pp. 1847-1855 (1994).

Li, X. ,"Synthesis of Selective Ligands for $GABA_A$/Benzodiazepine Receptors," PhD Dissertation, Department of Chemistry and Biochemistry, UW-Milwaukee, pp. i-xviii, 1-247 (2004).

Li, X. et al., "Synthesis, in Vitro Affinity, and Efficacy of a Bis 8-Ethynyl-4H-imidazo[1,5a]-[1,4]benzodiazepine Analogue, the First Bivalent $\alpha 5$ Subtype Selective BzR/$GABA_A$ Antagonist," Journal of Medicinal Chemistry, vol. 46, pp. 5567-5570 (2003).

Li, X. et al., "Studies in Search of Diazepam-Insensitive Subtype Selective Agents for $GABA_A$/Bz Receptors," Medicinal Chemistry Research, vol. 11, pp. 504-537 (2002).

(56) References Cited

OTHER PUBLICATIONS

Liu, R. et al., "Synthesis and Pharmacological Properties of Novel 8-Substituted Imidazobenzo-diazepines: High Affinity, Selective Probes for α5 Containing $GABA_A$ Receptors," Journal of Medicinal Chemistry, vol. 39, pp. 1928-1934 (1996).

Liu, R. et al., "Evidence for the Conservation of Conformational Topography at Five Major $GABA_A$/Benzodiazepine Receptor Subsites. Potent Affinities of The (S)-Enantiomers of Framework-Constrained 4,5-Substituted Pyrroloimidazobenzodiazepines," Medicinal Chemistry Research, vol. 7, pp. 25-35 (1997).

Locksley, R., "Asthma and Allergic Inflammation," Cell, vol. 140, pp. 777-783 (2010).

Long, A., "Addressing Unmet Needs in Asthma Care," P&T Digest, Asthma, vol. 14, pp. 16-22 (2005).

Lorenz, M. et al., "A Two Step Synthesis of BzR/GABAergic Active Flavones via a Wacker-related Oxidation," Tetrahedron Letters, vol. 51, pp. 1095-1098 (2010).

Lu, W.-Y., "The Potential Use of GABAergic Drugs in the Treatment of Asthma," Future Medicinal Chemistry, vol. 3, pp. 145-147 (2011).

MacDonald, R. L., "Benzodiazepines Mechanisms of Action, In Antiepileptic Drugs," Lippincott Williams and Wilkins, 5th edition, pp. 179-186 (2002).

Martin, M.J. et al., "Molecular Yardsticks. Rigid Probes to Define the Spatial Dimensions of the Benzodiazepine Receptor Binding Site," Journal of Medicinal Chemistry, vol. 35, pp. 4105-4117 (1992).

Mizuta, K. et al., "$GABA_A$ Receptors are Expressed and Facilitate Relaxation in Airway Smooth Muscle," American Journal of Physiology Lung Cellular and Molecular Physiology, vol. 294, L1206-L1216 (2008).

Munroe, M.E. et al., "Anti-inflammatory Effects of the Neurotransmitter Agonist Honokiol in a Mouse Model of Allegeric Asthma," The Journal of Immunology, vol. 185, pp. 5586-5597 (2010).

Namjoshi, O.A. et al., "Development of a Two-step Route to 3-PBC and βCCt, Two Agents Active Against Alcohol Self-Adminisitration in Rodent and Primate Models," The Journal of Organic Chemistry, vol. 76, pp. 4721-4727 (2011).

National Asthma Education and Prevention Program. Expert Panel Report 3: Guidelines for the diagnosis and management of asthma. National Heart, Lung, and Blood Institute, National Institutes of Health, US. Department of Health and Human Services. (2007).

Navarro, S. et al., "Regulation of the Expression of IL-6 in Human Monocytes," The Journal of Immunology, vol. 142, pp. 4339-4345 (1989).

Ohar, J.A., "Asthma Treatment Guidelines: Current Recommendations, Future Goals," P&T Digest, Asthma, vol. 14, pp. 23-27 (2005).

Opacka-Juffry, J. et al., "Evaluation of [Methyl- $^3$H]L655,708 and [Ethyl- $^3$H]RY80 as Putative PET Ligands for Central $GABA_A$ Receptors Containing α5 Subunit," Nuclear Medicine & Biology, vol. 26, pp. 743-748 (1999).

Pajouhesh, H. et al., "Medicinal Chemical Properties of Sucessful Central Nervous System Drugs," NeuroRx: The Journal of the American Society for Experimental NeuroTherapeutics, vol. 2, pp. 541-553 (2005).

Pawelec, G. et al., "Constitutive Interleukin 2 Production by the JURKAT Human Leukemic T Cell Line," European Journal of Immunology, vol. 12, pp. 387-392 (1982).

PCT/US2013/060859 International Search Report and Written Opinion dated Jan. 29, 2014 (12 pages).

PCT/US2013/060859 International Preliminary Report on Patentability and Written Opinion dated Mar. 24, 2015 (8 pages).

Reyes-García, M.G. et al.,"GABA (A) Receptor Subunits Rna Expression in Mice Peritoneal Macrophages Modulate Their IL-6/IL-12 Production," Journal of Neuroimmunology, vol. 188, pp. 64-68 (2007).

Rogers, D.F., "Airway Mucus Hypersecretion in Asthma: an Undervalued Pathology?," Current Opinion in Pharmacology, vol. 4, pp. 241-250 (2004).

Roland, N.J. et al., "The Local Side Effects of Inhaled Corticosteroids: Current Understanding and Review of the Literature," Chest, vol. 126, pp. 213-219 (2004).

Rudolf, U. et al., "Beyond Classical Benzodiazepines: Novel Therapeutic Potential of Gabaa Receptor Subtypes," Nature Reveiws Drug Discovery, vol. 10, pp. 685-697 (2011).

Saari, T.I. et al., "Enhancement of GABAergic Activity: Neuropharmacological Effects of Benzodiapines and Therapeutic Use in Anesthesiology," Pharmacological Reviews, vol. 63, pp. 243-267 (2011).

Savic, M.M. et al., "Novel Positive Allosteric Modulators of GABAA Receptors: Do Subtle Differences in Activity at α1 Plus α5 versus α Plus α3 Subunits Account for Dissimilarities in Behaviorial Effects in Rats?," Progress in Neuro-Psychopharmacology and Biological Psychiatry, vol. 34, pp. 376-386 (2010).

Sieghart, W. et al., "A Novel $GABA_A$ Receptor Pharmacology: Drugs Interacting with the $\alpha^+\beta^-$Interface," British Journal of Pharmacology, vol. 166, pp. 476-485 (2012).

Skolnick, P. et al., "β-Carbolines and Benzodiazepine Receptors: Structure-Activity Relationships and Pharmacologic Activity," Beta-Carbolines and Tetrahydroisoquinolines, Alan R. Liss, Inc., New York, pp. 233-252 (1982).

Stuckey, D.J. et al., "Detection of the Inhibitory Neurotransmitter GABA in Macrophages by Magnetic Resonance Spectroscopy," Journal of Leukocyte Biology, vol. 78, pp. 393-400 (2005).

Su, B. et al., "JNK Is Involved in Signal Integration during Costimulation of T Lymphocytes," Cell, vol. 77, pp. 727-736 (1994).

Takeshita, S. et al., "Differential Regualtion of IL-6 Gene Transcription and Expression by IL-4 and IL-10 in Human Monocytic Cell Lines," The Journal of Immunology, vol. 156, pp. 2591-2598 (1996).

Tan, K.R. et al., "Neural Bases for Addictive Properties of Benzodiazepines," Nature, vol. 463, pp. 769-774 (2010).

Tian, J. et al., "γ-Aminobutyric Acid Inhibits T Cell Autoimmunity and the Development of Inflammatory Responses in a Mouse Type 1 Diabetes Model," The Journal of Immunology, vol. 173, pp. 5298-5304.

Tliba, O. et al., "Is Airway Smooth Muscle the "Missing Link" Modulating Airway Inflammation in Asthma?," CHEST, vol. 133, pp. 236-242 (2008).

To, T. et al., "Global Asthma Prevalence in Adults: Findings from the Cross-Sectional World Health Survey," BMC Public Health, vol. 12, pp. 204-211 (2012).

Trudell, M.L. et al., "Synthesis of Substituted 7,12-Dihydropyrido[3,2-b:5,4-b"]diindoles: Rigid Planar Benzodiazepine Receptor Ligands with Inverse Agonist/Antagonist Properties," Journal of Medicinal Chemistry, vol. 33, pp. 2412-2420 (1990).

U.S. Food and Drug Administration, "FDA Drug Safety Communication: Drug labels now contain updated recommendations on the appropriate use of long-acting inhaled asthma medications called Long-Acting Beta-Agonists (LABAs)" Retrieved from URL: <http://www.fda.gov/Drugs/DrugSafety/PostmarketDrugSafetyInformationforPatientsandProviders/ucm213836.htm> (2010).

Weir, N.A. et al., "Achieving Symptom Control in Patients with Moderate Asthma," Clinical Medicine Insights: Circulatory, Respiratory and Pulmonary Medicine, vol. 6, pp. 1-11 (2012).

Wheeler, D.W. et al., Anaesthetic Impairment of Immune Function is Mediated via $GABA_A$ Receptors, PLoS One, vol. 6, pp. e17152-e17152 (2011).

Willis-Karp, M., "Interleukin-13 in Asthma Pathogenesis," Immunological Reviews, vol. 202, pp. 175-190 (2004).

Winkler, J. et al., "How the Lung Handles Drugs—Pharmacokinetics and Pharmacodynamics of Inhaled Corticosteroids," Proceedings of the American Thoracic Society, vol. 1, pp. 356-363 (2004).

Wong, G. et al., "Synthetic and Computer-Assisted Analysis of the Structural Requirements for Selective, High-Affinitiy Ligand Binding to Diazepam-Insensitive Benzodiazepine Receptors," Journal of Medicinal Chemistry, vol. 36, pp. 1820-1830 (1993).

(56) References Cited

OTHER PUBLICATIONS

Xiang, Y.-Y. et al., "A GABAergic System in Airway Epithelium is Essential for Mucus Overproduction in Asthma," Nature Medicine, vol. 13, pp. 862-867 (2007).
Xu, J. et al., "Cortisol Suppression as a Surrogate Marker for Inhaled Corticosteroid-Induced Growth Retardation in Children," European Journal of Pharmaceutical Sciences, vol. 36, pp. 110-121 (2008).
Yang, J. et al., "An Improved Process for the Synthesis of 4H-Imidazo[1,5-a][1,4] benzodiazepines," Synthesis, vol. 40, nihpa145687 (2009).
Zaidi, S. et al., "Regulation of Functional GABA Transporters in Human Airway Epithelial Cells by Protein Kinases," American Thoracic Society. Thematic Poster Session—Poster Presentation, [D76] Alveolar Epithelium: Novel Tools and Phenotypes, New York (2012).
Zaidi, S. et al., "Regulation of Functional GABA Transporter 2 in Human Airway Smooth Muscle and Epithelial Cells," American Thoracic Society. Thematic Poster Session—Poster Presentation, [D66] Airway Epithelium Injury, Infection and Repair, New York (2010).
Zhang, P. et al., "Synthesis of Novel Imidazobenzodiazepines as Probes of the Pharmacophore for "Diazepam-Insensitive" $GABA_A$ Receptors," Journal of Medicinal Chemistry, vol. 38, pp. 1679-1688 (1995).
Zhang, W. et al., "Chemical and Computer Assisted Development of an Inclusive Pharmacophore for the Benzodiazepine Receptor," Biological Inhibitors—Studies in Medicinal Chemistry, vol. 2, pp. 303-371 (1996).
Filizola et al., "Development of a 3D Pharmacophore for Nonspecific Ligand Recognition of cx1, cx2, cx3, cx5, and cx6 Containing GABAa / Benzodiazepine Receptors," Bioorganic & Medicinal Chemistry (2000) pp. 1799-1807, XP055251386.
EP13838190.0 Extended European Search Report dated Mar. 1, 2016 (9 pages).
Mohler, "Cognitive enhancement by pharmacological and behavioral interventions: the murine down syndrome model," article, Biochemical Pharmacology (2012), 84(8), 994-999.
Zurek et al., "Inhibition of x5 γ-Aminobutyric Acid Type A Receptors Restores Recognition Memory After General Anesthesia," article, Anesthesia & Analgesia (Hagerstown, MD, United States) (2012), 114(4), 845-855.
Numata et al., "Lack of an endogenous GABAA receptor-mediated tonic current in hypoglossal motoneurons," article, Journal of Physiology (Oxford, United Kingdom) (2012), 590(13), 2965-2976.
Atack, "GABAA receptor subtype-selective modulators. II. a5-selective inverse agonists for cognition enhancement," article, Current Topics in Medicinal Chemistry 2011), 11(9), 1203-1214.
Yoon et al., "Neurosteroid modulation of benzodiazepine-sensitive GABAA tonic inhibition in supraoptic magnocellular neurons," American Journal of Physiology (2011), 300(6, Pt. 2), R1578-R1587.
Vandormael et al., "Superpotent [Dmt1]Dermorphin Tetrapeptides Containing the 4-Aminotetrahydro-2-benzazepin-3-one Scaffold with Mixed m/d Opioid Receptor Agonistic Properties," Journal of Medicinal Chemistry (2011), 54(22), 7848-7859.
Saab et al., "Short-term memory impairment after isoflurane in mice is prevented by the a5 g-aminobutyric acid type a receptor inverse agonist L-655, 708," Anesthesiology (2010), 113(5), 1061-1071.
Ramerstorfer et al., "The point mutation g2F77I changes the potency and efficacy of benzodiazepine site ligands in different GABAA receptor subtypes," European Journal of Pharmacology (2010), 636(1-3), 18-27.
"Isojima et al., ""CkIe/d-dependent phosphorylation is a temperature-insensitive, period-determining process in them ammalian circadian clock,"" Proceedings of the National Academy of Sciences of the United States of America (2009), 106(37), 15744-15749, S15744/1-S15744/74."
Balic et al., "The a5 (H105R) mutation impairs a5 selective binding properties by altered positioning of the a5 subunit in GABAA receptors containing two distinct types of a subunits," Journal of Neurochemistry (2009), 110(1), 244-254.
Nasrallah et al., "Understanding your inhibitions: effects of GABA and GABAA receptor modulation on brain cortical metabolism," Journal of Neurochemistry (2009), 108(1), 57-71.
Sarantis et al., "Differential pharmacological properties of GABAA/benzodiazepine receptor complex in dorsal compared to ventral rat hippocampus," Neurochemistry International (2008), 52(6), 1019-1029.
Atack et al., "L-655708 enhances cognition in rats but is not proconvulsant at a dose selective for a5-containing GABAA receptors," Neuropharmacology (2006), 51(6), 1023-1029.
Khom et al., "Pharmacological properties of GABAA receptors containing gl subunits," Molecular Pharmacology (2006), 69(2), 640-649.
Atack et al., "Rat pharmacokinetics and pharmacodynamics of a sustained release formulation of the GABAA a5-selective compound L-655, 708," Drug Metabolism and Disposition (2006), 34(5), 887-893.
Orser et al., "Anesthetic sensitivity is reduced in hippocampal pyramidal neurons from GABAA receptor a5 subunit null mutant mice," International Congress Series (2005), 1283(Basic and Systemic Mechanisms of Anesthesia), 38-42.
Platt et al., "Contribution of a1GABAA and a5GABAA receptor subtypes to the discriminative stimulus effects of ethanol in squirrel monkeys," Journal of Pharmacology and Experimental Therapeutics (2005), 313(2), 658-667.
Atack et al., "In vivo labelling of a5 subunit-containing GABAA receptors using the selective radioligand [3H]L-655,708," Neuropharmacology (2005), 49(2), 220-229.
Ogris et al., "Affinity of various benzodiazepine site ligands in mice with a point mutation in the GABAA receptor g2 subunit," Biochemical Pharmacology (2004), 68(8), 1621-1629.
Navarro et al., "Behavioral profile of L-655,708, a selective ligand for the benzodiazepine site of GABA-A receptors which contain the a5 subunit, in social encounters between male mice," Aggressive Behavior (2004), 30(4), 319-325.
Li et al., "Development of selective ligands for benzodiazepine receptor subtypes by manipulating the substituents at positions 3- and 7- of optically active BzR ligands," Medicinal Chemistry Research (2004), 13(5), 259-281.
Caraiscos et al., "Tonic inhibition in mouse hippocampal CA1 pyramidal neurons is mediated by a5 subunit-containing g-aminobutyric acid type A receptors," Proceedings of the National Academy of Sciences of the United States of America (2004), 101(10), 3662-3667.
Chambers et al., "Identification of a novel, selective GABAA a5 receptor inverse agonist which enhances cognition," Journal of Medicinal Chemistry (2003), 46(11), 2227-2240.
Li et al., "Synthesis, in Vitro Affinity, and Efficacy of a Bis 8-Ethynyl-4H-imidazo[1,5a] [1,4]benzodiazepine Analogue, the First Bivalent a5 Subtype Selective BzR/GABAA Antagonist," Journal of Medicinal Chemistry (2003), 46(26), 5567-5570.
Navarro et al., "Anxiogenic-like activity of L-655,708, a selective ligand for the benzodiazepine site of GABAA receptors which contain the alpha-5 subunit, in the elevated plus-maze test," Progress in Neuro-Psychopharmacology & Biological Psychiatry (2002), 26(7-8), 1389-1392.
Lingford-Hughes et al., "Imaging the GABA-benzodiazepine receptor subtype containing the a5-subunit in vivo with [11C]Ro15 4513 positron emission tomography," Journal of Cerebral Blood Flow and Metabolism (2002), 22(7), 878-889.
Casula et al., "Identification of amino acid residues responsible for the a5 subunit binding selectivity of L-655,708, a benzodiazepine binding site ligand at the GABAA receptor," Journal of Neurochemistry (2001), 77(2), 445-451.
Del Rio et al., "Prevalence between different a subunits performing the benzodiazepine binding sites in native heterologous GABAA receptors containing the a2 subunit," Journal of Neurochemistry (2001), 79(1), 183-191.

(56) References Cited

OTHER PUBLICATIONS

Filizola et al., "Development of a 3D pharmacophore for nonspecific ligand recognition of a1, a2, a3, a5, and a6 containing gabaA/benzodiazepine receptors," Bioorganic & Medicinal Chemistry (2000), 8(7), 1799-1807.

He et al., "Pharmacophore/receptor models for GABAA/BzR a2b3g2, a3b3g2 and a4b3g2 recombinant subtypes. Included volume analysis and comparison to a1b3g2, a5b3g2 and a6b3g2 subtypes," Drug Design and Discovery (2000), 17(2), 131-171.

Huang et al., "Pharmacophore/receptor models for GABAA/BzR subtypes (a1b3g2, a5b3g2, and a6b3g2) via a comprehensive ligand-mapping approach," Journal of Medicinal Chemistry (2000), 43(1), 71-95.

Opacka-Juffry et al., "Evaluation of [methyl-3H] L655,708 and [ethyl-3H]RY80 as putative PET ligands for central GABAA receptors containing a5 subunit," Nuclear Medicine and Biology (1999), 26(7), 743-748.

Araujo et al., "Native g-aminobutyric acid type A receptors from rat hippocampus, containing both, a1 and a5 subunits, exhibit a single benzodiazepine binding site with a5 pharmacological properties," Journal of Pharmacology and Experimental Therapeutics (1999), 290(3), 989-997.

Huang et al., "Predictive Models for GABAA/Benzodiazepine Receptor Subtypes: Studies of Quantitative Structure-Activity Relationships for Imidazobenzodiazepines at Five Recombinant GABAA/Benzodiazepine Receptor Subtypes [axb3g2 (x = 1-3, 5, and 6)] via Comparative Molecular Field Analysis," Journal of Medicinal Chemistry (1998), 41(21), 4130-4142.

Sur et al., "Rat and human hippocampal a5 subunit-containing g-aminobutyric acidA receptors have a5b3g2 pharmacological characteristics," Molecular Pharmacology (1998), 54(5), 928-933.

Quirk et al., "[3H] L-655,708, a novel ligand selective for the benzodiazepine site of GABAA receptors which contain the a5 subunit," Neuropharmacology (1996), 35(9/10), 1331-1335.

Li et al., "Studies in search of diazepam-insensitive subtype selective agents for GABAA/Bz receptors," Medicinal Chemistry Research (2003), 11(9), 504-537.

EP13838190.0 European Examination and Search Report dated Jan. 3, 2017 (6 pages).

Belvisi et al., "Modulation of non-adrenergic, non-cholinergic neural bronchoconstrictin in guinea-pig airways via GABAb-receptors," specification (1989) Br. J. Pharmacol, 97, pp. 1225-1231.

Office Action from the Japanese Patent Office for Application No. 2015-533213 dated Jan. 6, 2017 (8 pages).

* cited by examiner

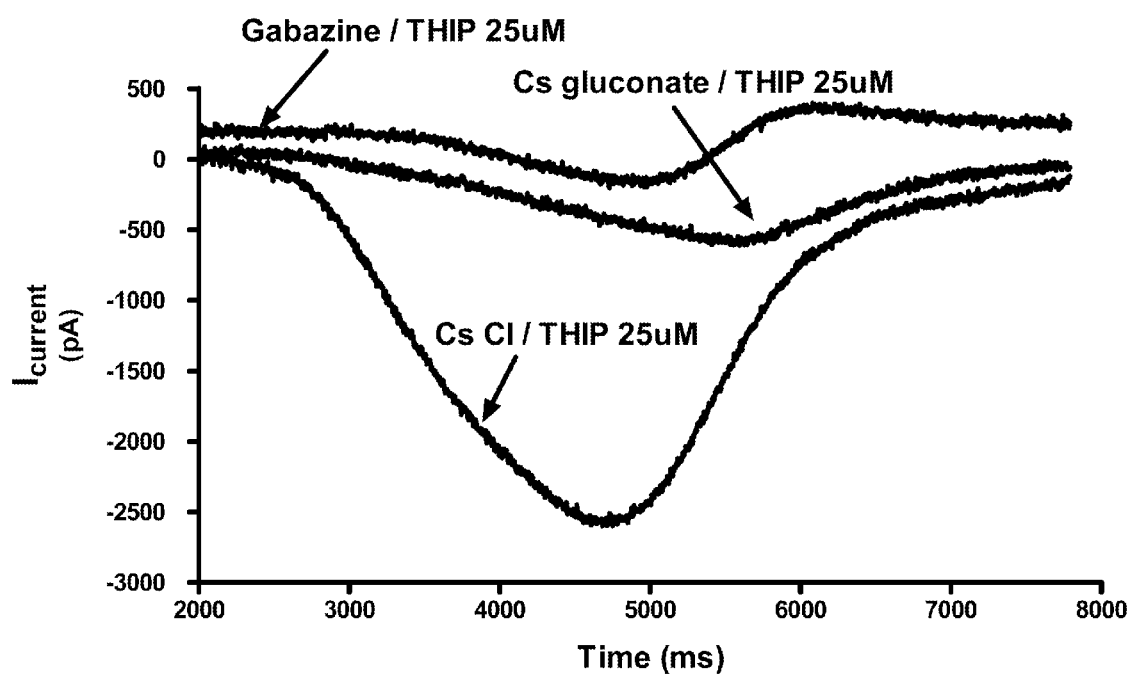

MRS-XHE-III-74 ETHYL

MRS-XHe-III-74

MRS-01-53

MRS-01-36

MRS-XHE-III-74 C-3-ACID

MRS-01-68

MRS-01-64

MRS-01-66

MRS-01-52

MRS-01-67 n=1 or 2; R = CH(CD₃)CH₃ (R)
n=1 or 2; R = CH(CD₃)CH₃ (S)
n=1 or 2; R = CH(CF₃)CH₃ (R)
n=1 or 2; R = CH(CF₃)CH₃ (S)

n=1 or 2; R = CH(CH₃)C₂H₅ (R)
n=1 or 2; R = CH(CH₃)C₂H₅ (S)
n=1 or 2; R = CH(CF₃)C₂H₅ (R)
n=1 or 2; R = CH(CF₃)C₂H₅ (S)

n=1 or 2; R = CH(CH₃)
n=1 or 2; R = CH(CH₃)

n=1 or 2; R = cyclopropane n=1 or 2; R = CH(2,2-difluoro)
    cyclopropane (R)
n=1 or 2; R = CH(2,2-difluoro)
    cyclopropane (S)

X=OCH₃,I,F; n=1 or 2; R₁=H, R₂=CH₃
X=OCH₃,I,F; n=1 or 2; R₁=CH₃, R₂=CH₃

Rotamers
X=OCH₃,I,F; n=1 or 2; R₁=CF₃, R₂=CH₃
X=OCH₃,I,F; n=1 or 2; R₁=CH₃, R₂=CF₃

X=OCH₃,I,F; n=1 or 2

X=OCH₃,I,F; n=1 or 2

GABAA AGONISTS AND METHODS OF USING TO CONTROL AIRWAY HYPERRESPONSIVENESS AND INFLAMMATION IN ASTHMA

CROSS-REFERENCE TO RELATED APPLICATIONS

This application is a national stage filing under 35 U.S.C. 371 of International Application No. PCT/US2013/060859, filed Sep. 20, 2013, and claims to the benefit of U.S. Provisional Patent Application No. 61/703,902, filed on Sep. 21, 2012, the entire contents of which are hereby incorporated by reference in their entireties.

STATEMENT REGARDING FEDERALLY SPONSORED RESEARCH OR DEVELOPMENT

This invention was made with United States government support under NIH grant numbers MH-046851, MH-096463, GM065281 and GM093137. The United States government has certain rights to this invention.

BACKGROUND

Bronchoconstrictive diseases are a major health concern worldwide. This includes chronic obstructive pulmonary disease (COPD), bronchopulmonary dysplasia (BPD), and despite existing treatments such as β-adrenergic agonists, inhaled corticosteroids, and inhaled anti-cholinergics, bronchoconstrictive diseases remain highly prevalent. Asthma by itself affects 300 million people worldwide. Since this asthma predisposes patients to severe acute airway constriction, novel mechanisms capable of promoting airway smooth muscle relaxation would be clinically valuable.

Thus there continues to be demand and need for effective therapeutics and treatments against bronchoconstrictive diseases. New pharmacologic approaches to treat these diseases are limited. Therapeutic limitations are especially apparent with regard to medications that promote acute airway smooth muscle relaxation, as α-adrenoceptor agonists and anti-cholinergics remain the only drug classes currently utilized to treat acute airway constriction.

SUMMARY

In one embodiment, the invention provides a compound according to formula (I):

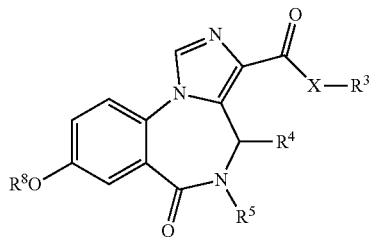

and all isomers and salts thereof,
wherein
$R^3$ is selected from $C_{1-4}$ alkyl, $C_{1-5}$ cycloalkyl, adamantyl, or H;
X is —O—, —S—, —$NR^N$—, or —$NR^NC(O)$—;
$R^N$ is selected from H or $C_{1-4}$ alkyl;
$R^4$ is selected from $C_{1-4}$ alkyl;
$R^5$ is selected from H or $C_{1-4}$ alkyl;
or $R^4$ and $R^5$ together form a ring of 4 to 5 member atoms;
$R^8$ is selected from $C_{1-4}$ alkyl or $C_{1-4}$ cycloalkyl.

In one embodiment, the present invention provides a pharmaceutical composition including a compound of formula (I) and a pharmaceutically acceptable carrier. In some embodiments, the composition may be an oral or an aerosol formulation.

In one embodiment, the invention provides a method of reducing airway constriction comprising administering an effective amount of a GABAergic agent having reduced benzodiazepine-type CNS effects to a subject in need thereof In one embodiment, the invention provides a method of reducing lung inflammation comprising administering an effective amount of a GABAergic agent having reduced benzodiazepine-type CNS effects to a subject in need thereof.

In one embodiment, the invention provides a method of reducing development of disease in a subject having risk factors associated with lung inflammation comprising administering an effective amount of a GABAergic agent having reduced benzodiazepine-type CNS effects to a subject in need thereof.

In one embodiment, the invention provides a method of treating lung disease comprising administering an effective amount of a GABAergic agent having reduced benzodiazepine-type CNS effects to a subject in need thereof.

Other aspects of the invention will become apparent by consideration of the detailed description and accompanying drawings.

DETAILED DESCRIPTION

Figure 1:
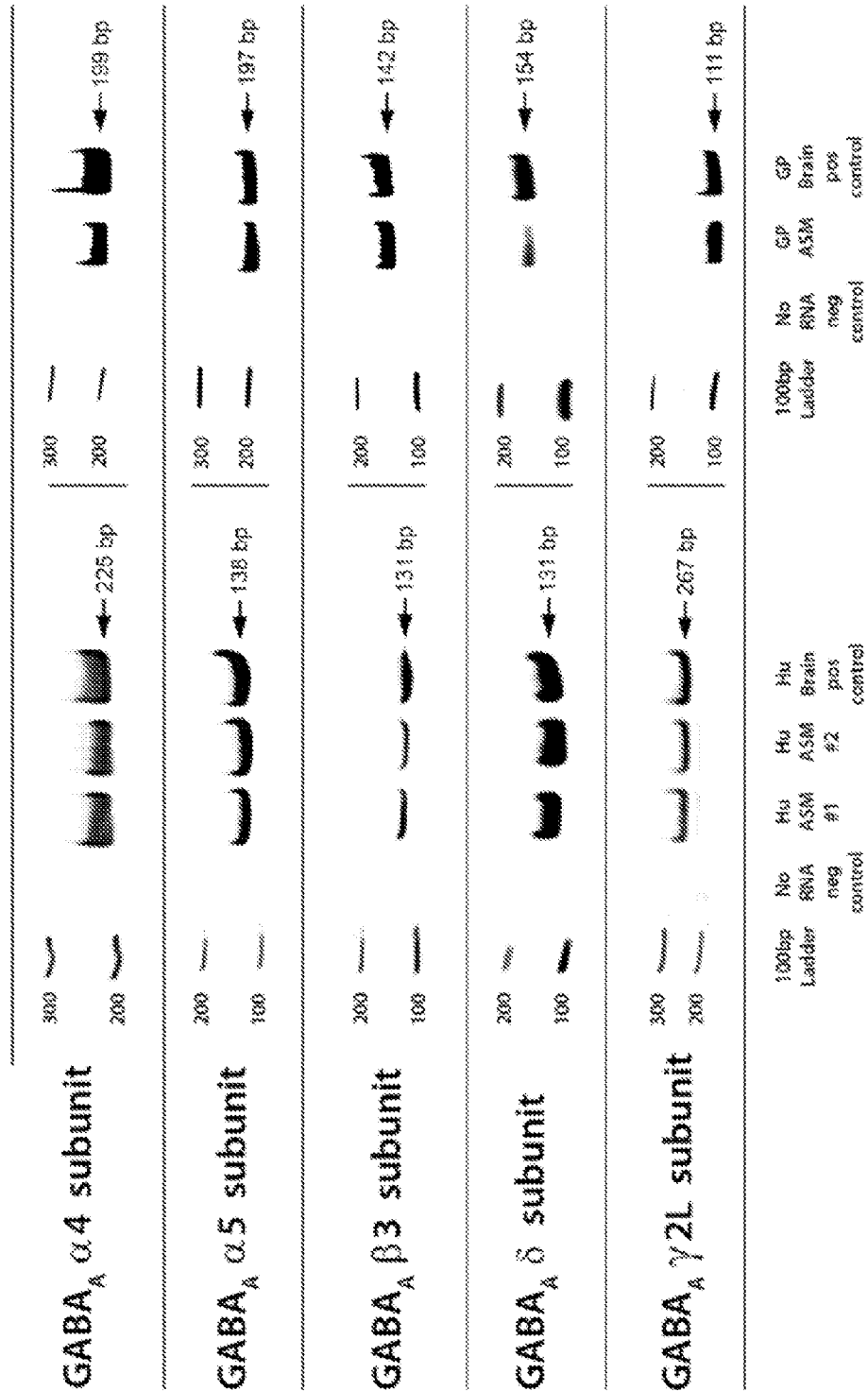
FIG. 1 shows representative images of RTPCR products corresponding to specific GABAA subunits following laser capture microdissection of airway smooth muscle cells harvested from human and guinea pig tracheal airway smooth muscle. (bp=base pairs, ASM=airway smooth muscle, Hu=human, GP=guinea pig, neg=negative, and pos=positive). Representative of 2 separate individual human or guinea pig tracheas.

Recent studies have shown the presence of functional gamma-amino butyric acid type A receptors ($GABA_A R$) on the surface of cell types involved in asthmatic lung pathophysiology. Importantly, $GABA_A R$ signaling can influence the contractile state of airway smooth muscle (ASM), inflammatory processes, and proliferation of airway epithelial cells (AEC). Despite the growing appreciation of $GABA_A R$ signaling acting locally in the lung, a strategy that unifies and targets $GABA_A R$ responses has not been developed or exploited therapeutically for asthma treatment. Accordingly, the inventors contemplate the identification of a novel asthma therapy by systematically probing human lung cell types to identify agonists that are suppressive for ASM and immune/inflammatory cells without stimulating AEC hypertrophy.

Activation of endogenous airway smooth muscle $GABA_A$ receptors potentiate α-adrenoceptor-mediated relaxation, and molecular analysis of airway smooth muscle reveals that the α-subunit component of these $GABA_A$ receptors is limited to the α4 and α5 subunits.

The present invention provides novel compounds, which may bind to specific ionotropic (ligand-gated) ion channels expressed in lymphatic tissue on immune/inflammatory cells and airway smooth muscle and consequently relax contraction. This novel finding details a new signaling pathway and protein target for relaxing airway smooth muscle contraction and can potentially be developed in to a novel therapeutic against airway constriction, lung inflammation and inflammation associated with autoimmune diseases. Thus, among other things, the present invention provides novel compounds which provide a novel therapeutic option against airway constriction, lung inflammation and inflammation associated with autoimmune diseases. and methods of using these compounds to treat various diseases.

Definitions

Definitions of specific functional groups and chemical terms are described in more detail below. For purposes of this invention, the chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March March's Advanced Organic Chemistry, 5th Edition, John Wiley & Sons, Inc., New York, 2001; Larock, Comprehensive Organic Transformations, VCH Publishers, Inc., New York, 1989; Carruthers, Some Modern Methods of Organic Synthesis, 3rd Edition, Cambridge University Press, Cambridge, 1987; the entire contents of each of which are incorporated herein by reference.

The term "acyl" refers to an alkylcarbonyl, cycloalkylcarbonyl, heterocyclylcarbonyl, arylcarbonyl or heteroarylcarbonyl substituent, any of which may be further substituted (e.g., with one or more substituents).

The term "alkyl" refers to a straight or branched hydrocarbon chain, containing the indicated number of carbon atoms. For example, $C_1$-$C_{12}$ alkyl indicates that the alkyl group may have from 1 to 12 (inclusive) carbon atoms, and $C_1$-$C_4$ alkyl indicates that the alkyl group may have from 1 to 4 (inclusive) carbon atoms. An alkyl group may be optionally substituted. Examples of C1-C4 alkyl groups include methyl, ethyl, n-propyl, isopropyl, n-butyl, sec-butyl and tert-butyl.

The term "alkenyl" refers to a straight or branched hydrocarbon chain having one or more double bonds. Examples of alkenyl groups include, but are not limited to, allyl, propenyl, 2-butenyl, 3-hexenyl and 3-octenyl groups. One of the double bond carbons may optionally be the point of attachment of the alkenyl substituent. An alkenyl group may be optionally substituted.

The term "alkynyl" refers to a straight or branched hydrocarbon chain having one or more triple bonds. Examples of alkynyl groups include, but are not limited to, ethynyl, propargyl, and 3-hexynyl. One of the triple bond carbons may optionally be the point of attachment of the alkynyl substituent. An alkynyl group may be optionally substituted.

The term "aryl" refers to an aromatic monocyclic, bicyclic, or tricyclic hydrocarbon ring system, wherein any ring atom capable of substitution can be substituted (e.g., with one or more substituents). Examples of aryl moieties include, but are not limited to, phenyl, naphthyl, and anthracenyl.

The term "arylalkyl" refers to an alkyl moiety in which an alkyl hydrogen atom is replaced with an aryl group. Arylalkyl includes groups in which more than one hydrogen atom has been replaced with an aryl group. Examples of arylalkyl groups include benzyl, 2-phenylethyl, 3-phenylpropyl, 9-fluorenyl, benzhydryl, and trityl groups.

The term "cycloalkyl" as used herein refers to nonaromatic, saturated or partially unsaturated cyclic, bicyclic, tricyclic or polycyclic hydrocarbon groups having 3 to 12 carbons (e.g., 3, 4, 5, 6 or 7 carbon atoms). Any ring atom can be substituted (e.g., with one or more substituents). Cycloalkyl groups can contain fused rings. Fused rings are rings that share one or more common carbon atoms. Examples of cycloalkyl groups include, but are not limited to, cyclopropyl, cyclobutyl, cyclopentyl, cyclohexyl, cyclohexenyl, cyclohexadienyl, methylcyclohexyl, adamantyl, norbornyl and norbornenyl.

The term "halo" or "halogen" as used herein refers to any radical of fluorine, chlorine, bromine or iodine.

The term "haloalkyl" as used herein refers to an alkyl in which one or more hydrogen atoms are replaced with a halogen, and includes alkyl moieties in which all hydrogens have been replaced with halogens (e.g., perfluoroalkyl such as $CF_3$).

The term "heteroaryl" as used herein refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms independently selected from O, N, S, P and Si (e.g., carbon atoms and 1-3, 1-6, or 1-9 heteroatoms independently selected from O, N, S, P and Si if monocyclic, bicyclic, or tricyclic, respectively). Any ring atom can be substituted (e.g., with one or more substituents). Heteroaryl groups can contain fused rings, which are rings that share one or more common atoms. Examples of heteroaryl groups include, but are not limited to, radicals of pyridine, pyrimidine, pyrazine, pyridazine, pyrrole, imidazole, pyrazole, oxazole, isoxazole, furan, thiazole, isothiazole, thiophene, quinoline, isoquinoline, quinoxaline, quinazoline, cinnoline, indole, isoindole, indolizine, indazole, benzimidazole, phthalazine, pteridine, carbazole, carboline, phenanthridine, acridine, phenanthroline, phenazine, naphthyridines and purines.

The term "heterocyclyl" as used herein refers to a non-aromatic, saturated or partially unsaturated 3-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, S, Si and P (e.g., carbon atoms and 1-3, 1-6, or 1-9 heteroatoms of O, N, S, Si and P if monocyclic, bicyclic, or tricyclic, respectively). Any ring atom can be substituted (e.g., with one or more substituents). Heterocyclyl groups can contain fused rings, which are rings that share one or more common atoms. Examples of heterocyclyl groups include, but are not limited to, radicals of tetrahydrofuran, tetrahydrothiophene, tetrahydropyran, piperidine, piperazine, morpholine, pyrroline, pyrimidine, pyrrolidine, indoline, tetrahydropyridine, dihydropyran, thianthrene, pyran, benzopyran, xanthene, phenoxathiin, phenothiazine, furazan, lactones, lactams such as azetidinones and pyrrolidinones, sultams, sultones, and the like.

The term "hydroxy" refers to an —OH radical. The term "alkoxy" refers to an —O-alkyl radical. The term "aryloxy" refers to an —O-aryl radical. The term "haloalkoxy" refers to an —O-haloalkyl radical.

The term "substituent" refers to a group "substituted" on an alkyl, alkenyl, alkynyl, cycloalkyl, heterocyclyl, aryl, arylalkyl or heteroaryl group at any atom of that group. Suitable substituents include, without limitation: acyl, acylamido, acyloxy, alkoxy, alkyl, alkenyl, alkynyl, amido, amino, carboxy, cyano, ester, halo, hydroxy, imino, nitro, oxo (e.g., C=O), phosphonate, sulfinyl, sulfonyl, sulfonate, sulfonamino, sulfonamido, thioamido, thiol, thioxo (e.g., C=S), and ureido. In embodiments, substituents on a group are independently any one single, or any combination of the aforementioned substituents. In embodiments, a substituent may itself be substituted with any one of the above substituents.

The above substituents may be abbreviated herein, for example, the abbreviations Me, Et and Ph represent methyl, ethyl and phenyl, respectively. A more comprehensive list of the abbreviations used by organic chemists appears in the first issue of each volume of the Journal of Organic Chemistry; this list is typically presented in a table entitled Standard List of Abbreviations. The abbreviations contained in said list, and all abbreviations used by organic chemists of ordinary skill in the art, are hereby incorporated by reference.

For compounds, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

Where substituent groups are specified by their conventional chemical formulae, written from left to right, they optionally encompass substituents resulting from writing the structure from right to left, e.g., —CH$_2$O— optionally also recites —OCH$_2$—.

In accordance with a convention used in the art, the group:

is used in structural formulas herein to depict the bond that is the point of attachment of the moiety or substituent to the core or backbone structure.

In the context of treating a disorder, the term "effective amount" as used herein refers to an amount of the compound or a composition comprising the compound which is effective, upon single or multiple dose administrations to a subject, in treating a cell, or curing, alleviating, relieving or improving a symptom of the disorder in a subject. An effective amount of the compound or composition may vary according to the application. In the context of treating a disorder, an effective amount may depend on factors such as the disease state, age, sex, and weight of the individual, and the ability of the compound to elicit a desired response in the individual. In an example, an effective amount of a compound is an amount that produces a statistically significant change in a given parameter as compared to a control, such as in cells (e.g., a culture of cells) or a subject not treated with the compound.

It is specifically understood that any numerical value recited herein (e.g., ranges) includes all values from the lower value to the upper value, i.e., all possible combinations of numerical values between the lowest value and the highest value enumerated are to be considered to be expressly stated in this application. For example, if a concentration range is stated as 1% to 50%, it is intended that values such as 2% to 40%, 10% to 30%, or 1% to 3%, etc., are expressly enumerated in this specification. These are only examples of what is specifically intended.

Compounds

Compounds of the present invention may be a compound according to formula (I):

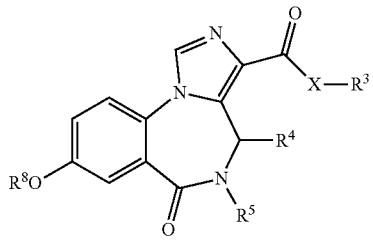

and all isomers and salts thereof,
wherein
R$^3$ is selected from C$_{1-4}$ alkyl, C$_{1-5}$ cycloalkyl, adamantyl, or H;
X is —O—, —S—, —NR$^N$—, or —NR$^N$C(O)—;
R$^N$ is selected from H or C$_{1-4}$ alkyl;
R$^4$ is selected from C$_{1-4}$ alkyl;

R$^5$ is selected from H or C$_{1-4}$ alkyl;
or R$^4$ and R$^5$ together form a ring of 4 to 5 member atoms;
R$^8$ is selected from C$_{1-4}$ alkyl or C$_{1-4}$ cycloalkyl.

In some embodiments, one or more hydrogens may be replaced with a deuterium.

Suitably, R$^3$ may be t-butyl or cyclopropyl. In some embodiments, R$^3$ is an alkyl group substituted with one or more halogens, such as a fluoro. In certain embodiments, R$^3$ may be H, —CH$_3$, i-butyl, —CH(CF$_3$)CH$_2$CH$_3$, —CH(CF$_3$)CH$_3$, —CH(CD$_3$)CH$_3$, —CF(CD$_3$)CH$_3$, i-propyl, t-butyl, —CH(CF$_3$)$_2$, cyclopropyl, —CH$_2$CD$_3$, -CD(CH$_3$)CH$_2$CH$_3$, -CD(CF$_3$)CH$_2$CH$_3$, -CD(CF$_3$)CH$_3$, -CD(CD$_3$)CH$_3$, —CF(CD$_3$)CH$_3$ and -CD(CH$_3$)$_2$ Suitably, R$^8$ is isopropyl, cyclopropyl, methyl, ethyl, t-butyl, or CD$_3$.

Suitably X is —O— or NR$^N$—.

Suitably R$^4$ and R$^5$ form a four- or five-membered ring. The ring may be a carbocycle or a heterocycle.

Suitably, X—R$^3$ is —N(CF$_3$)CH$_3$, —NHCH$_3$, —N(CH$_3$)$_2$, —NHC(CH$_3$)$_3$, —SCH$_2$CH$_3$, —SC(CH$_3$)$_3$,

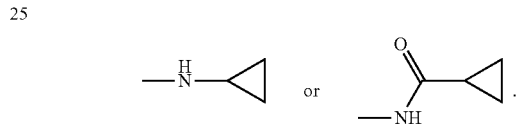

Suitably, the compound may be the S-isomer. Alternatively, the compound may be the R-isomer.

In another embodiment, a compound of the present invention is a compound of formula (IIA) or (IIB):
wherein

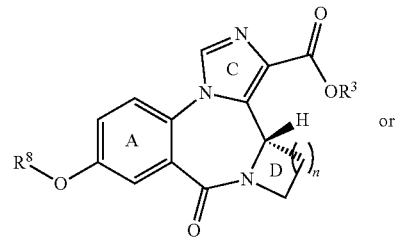

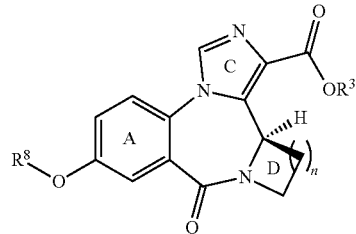

R$^8$ is -CD$_3$, —CH$_3$, ethyl, t-butyl or cyclopropyl;
R$^3$ is H, —CH$_3$, i-butyl, —CH(CF$_3$)CH$_2$CH$_3$, —CH(CF$_3$)CH$_3$, —CH(CD$_3$)CH$_3$, —CF(CD$_3$)CH$_3$, i-propyl, t-butyl, —CH(CF$_3$)$_2$, cyclopropyl, —CH$_2$CD$_3$, -CD(CH$_3$)CH$_2$CH$_3$, -CD(CF$_3$)CH$_2$CH$_3$, -CD(CF$_3$)CH$_3$, -CD(CD$_3$)CH$_3$, —CF(CD$_3$)CH$_3$ or -CD(CH$_3$)$_2$; and
n is 1 or 2.

In some embodiments, the compound of the present invention is a compound of formula (IIIA) or (IIIB):
wherein

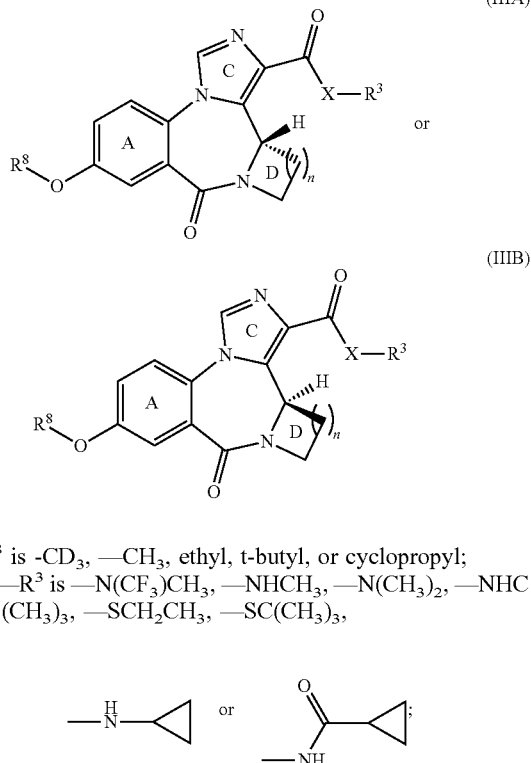

R[8] is -CD$_3$, —CH$_3$, ethyl, t-butyl, or cyclopropyl;
X—R[3] is —N(CF$_3$)CH$_3$, —NHCH$_3$, —N(CH$_3$)$_2$, —NHC(CH$_3$)$_3$, —SCH$_2$CH$_3$, —SC(CH$_3$)$_3$,

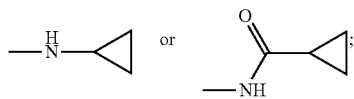

and
n is 1 or 2.

In some aspects the compounds of the present invention selectively target the α4 and α5 subunits of GABA$_A$ receptors. In some aspects, the compounds of the present invention are allosteric modulators of the GABA$_A$ receptors that are selective for the α4 and α5 benzodiazepine allosteric modulatory sites on GABA$_A$ receptors. In some aspects, the compounds of the present invention may have limited to no ability to cross the blood-brain barrier.

For compounds according to the present invention, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

Where substituent groups are specified by their conventional chemical formulae, written from left to right, they optionally encompass substituents resulting from writing the structure from right to left, e.g., —CH$_2$O— optionally also recites —OCH$_2$—.

Compounds according to the present invention include compounds that differ only in the presence of one or more isotopically enriched atoms. For example, compounds may have the present structures except for the replacement of hydrogen by deuterium or tritium, or the replacement of a carbon by a $^{13}$C- or $^{14}$C-enriched carbon.

A compound according to the present invention can be in the form of a salt, e.g., a pharmaceutically acceptable salt. The term "pharmaceutically acceptable salt" includes salts of the active compounds that are prepared with relatively nontoxic acids or bases, depending on the particular substituents found on the compounds. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulfuric acid, methanesulfonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts, alkaline earth metal salts, e.g. calcium or magnesium salts; and salts formed with suitable organic ligands, e.g. quaternary ammonium salts.

Neutral forms of the compounds may be regenerated by contacting the salt with a base or acid and isolating the parent compound in a conventional manner. The parent form of the compound differs from the various salt forms in certain physical properties, such as solubility in polar solvents, but otherwise the salts are equivalent to the parent form of the compound for the purposes of this disclosure.

In addition to salt forms, the present invention may also provide compounds according to the present invention in a prodrug form. Prodrugs of the compounds are those compounds that readily undergo chemical changes under physiological conditions to provide the active compounds. Prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Compounds according to the present invention can be, for example, an enantiomerically enriched isomer of a stereoisomer described herein. Enantiomer, as used herein, refers to either of a pair of chemical compounds whose molecular structures have a mirror-image relationship to each other. For example, a compound may have an enantiomeric excess of at least about 10%, 15%, 20%, 25%, 30%, 35%, 40%, 45%, 50%, 55%, 60%, 65%, 70%, 75%, 80%, 85%, 90%, 95%, 96%, 97%, 98%, or 99%.

A preparation of a compound according to the present invention may be enriched for an isomer of the compound having a selected stereochemistry, e.g., R or S, corresponding to a selected stereocenter. For example, the compound may have a purity corresponding to a compound having a selected stereochemistry of a selected stereocenter of at least about 60%, 65%, 70%, 75%, 80%, 85%, 90%, 95%, 96%, 97%, 98%, or 99%. A compound can, for example, include a preparation of a compound disclosed herein that is enriched for a structure or structures having a selected stereochemistry, e.g., R or S, at a selected stereocenter.

In some embodiments, a preparation of a compound according to the present invention may be enriched for isomers (subject isomers) which are diastereomers of the compound. Diastereomer, as used herein, refers to a stereoisomer of a compound having two or more chiral centers that is not a mirror image of another stereoisomer of the same compound. For example, the compound may have a purity corresponding to a compound having a selected diastereomer of at least about 60%, 65%, 70%, 75%, 80%, 85%, 90%, 95%, 96%, 97%, 98%, or 99%.

When no specific indication is made of the configuration at a given stereocenter in a compound, any one of the configurations or a mixture of configurations is intended.

Compounds may be prepared in racemic form or as individual enantiomers or diastereomers by either stereospecific synthesis or by resolution. The compounds may, for example, be resolved into their component enantiomers or diastereomers by standard techniques, such as the formation of stereoisomeric pairs by salt formation with an optically active base, followed by fractional crystallization and regeneration of the free acid. The compounds may also be resolved by formation of stereoisomeric esters or amides, followed by chromatographic separation and removal of the chiral auxiliary. Alternatively, the compounds may be resolved using a chiral HPLC column. The enantiomers also may be obtained from kinetic resolution of the racemate of corresponding esters using lipase enzymes.

A compound according to the present invention can also be modified by appending appropriate functionalities to enhance selective biological properties. Such modifications are known in the art and include those that increase biological penetration into a given biological system (e.g., blood, lymphatic system, central nervous system), increase oral availability, increase solubility to allow administration by injection, alter metabolism, and/or alter rate of excretion. Examples of these modifications include, but are not limited to, esterification with polyethylene glycols, derivatization with pivolates or fatty acid substituents, conversion to carbamates, hydroxylation of aromatic rings, and heteroatom substitution in aromatic rings.

The compounds of the present invention may also be adapted as "soft drugs". A soft drug may be defined as a biologically active compound having predictable and controllable in vivo metabolism to inert species after it achieves its desired therapeutic effect. That is, the compounds of the present invention may contain a moiety which allows for rapid metabolism of the compounds in the lung or other target tissue. In lungs, several cytochrome isoforms are found, as well as other biotransformation enzymes such as sulfotransferases, UDP glucuronosyl transferases, glutathione S-transferases, esterases, peptidases, cyclo-oxygenases, and flavine mono-oxygenases . The wide range of biotransformation enzymes enables metabolism of a broad spectrum of chemically different substrates, for example compounds with a labile ester function. Soft drugs would have shorter systemic half-life than compounds without the moiety and may limit undesirable systemic effects (such a distribution to CNS tissues).

Synthesis

Compounds of formulae (I), (II) and (III) may be synthesized using commercially available starting materials. Exemplary syntheses are illustrated below.

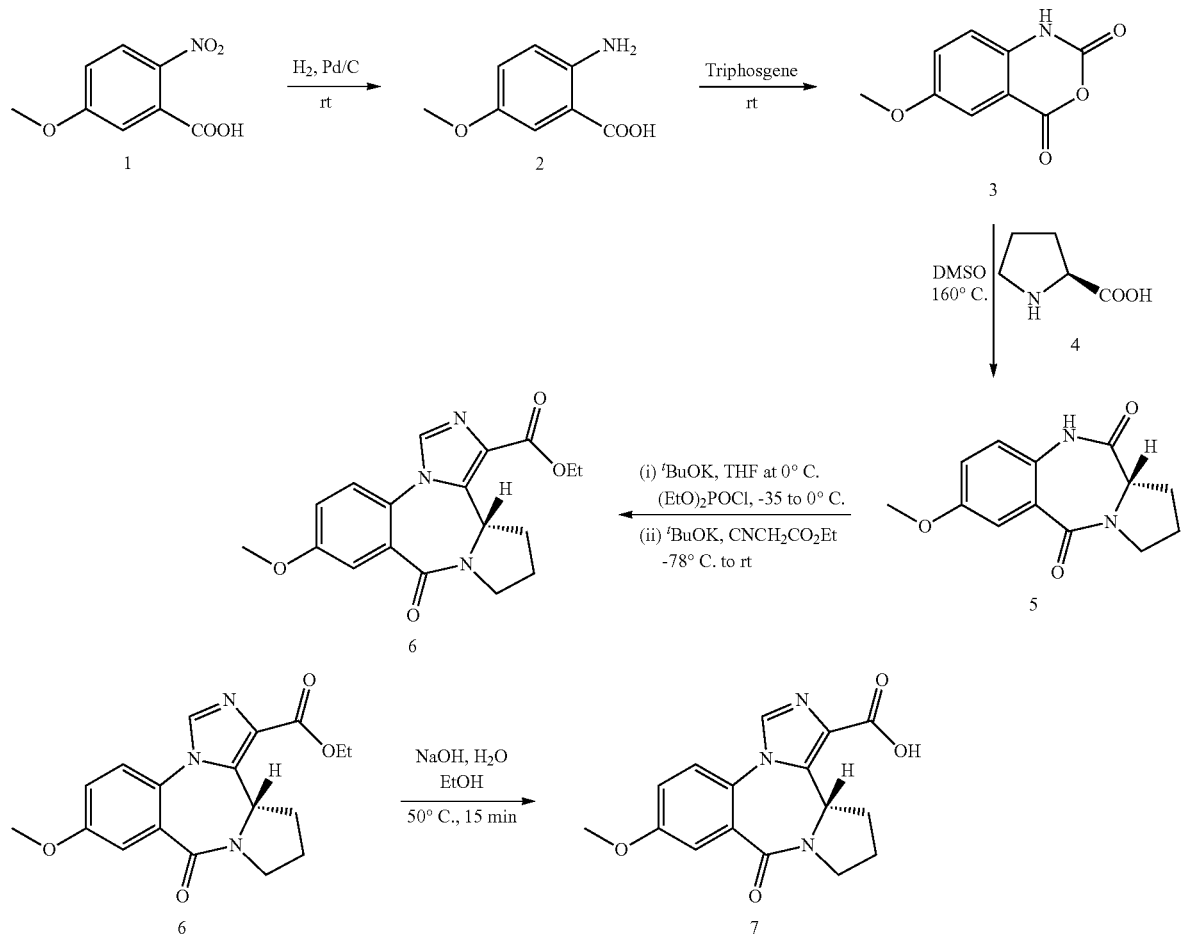

-continued

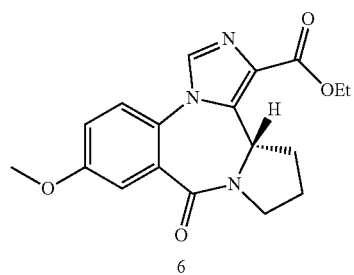 Li granules, THF
ROH
50° C. → 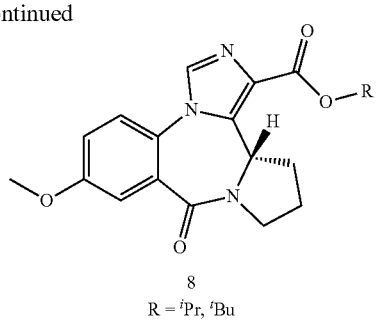

6

8
R = $^i$Pr, $^t$Bu

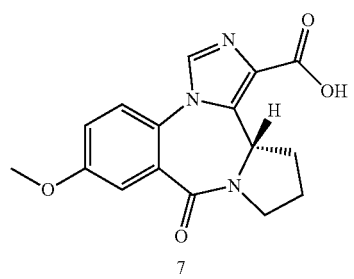 (i) CDI, toluene, 65° C.
(ii) (CF$_3$)$_2$CHOH → 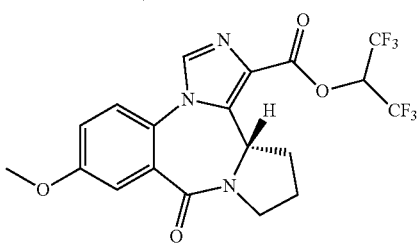

7

10

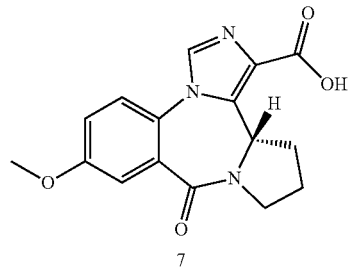 (i) CDI, toluene, mw
(ii) —NH$_2$, DBU → 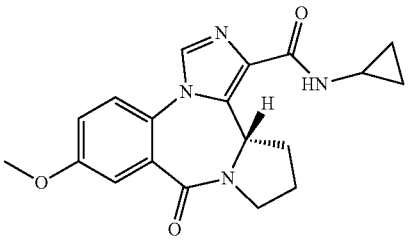

7

12

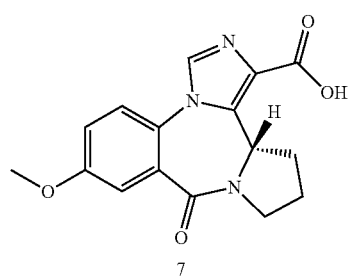 (i) SOCl$_2$, CH$_2$Cl$_2$
60° C., 1 h
(ii) R, Et$_3$N, rt, 7 h → 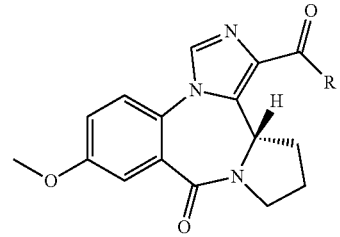

7

13
R = OCH$_3$, SCH$_2$CH$_3$,
NHCH$_3$, N(CH$_3$)$_2$

Figure 14:
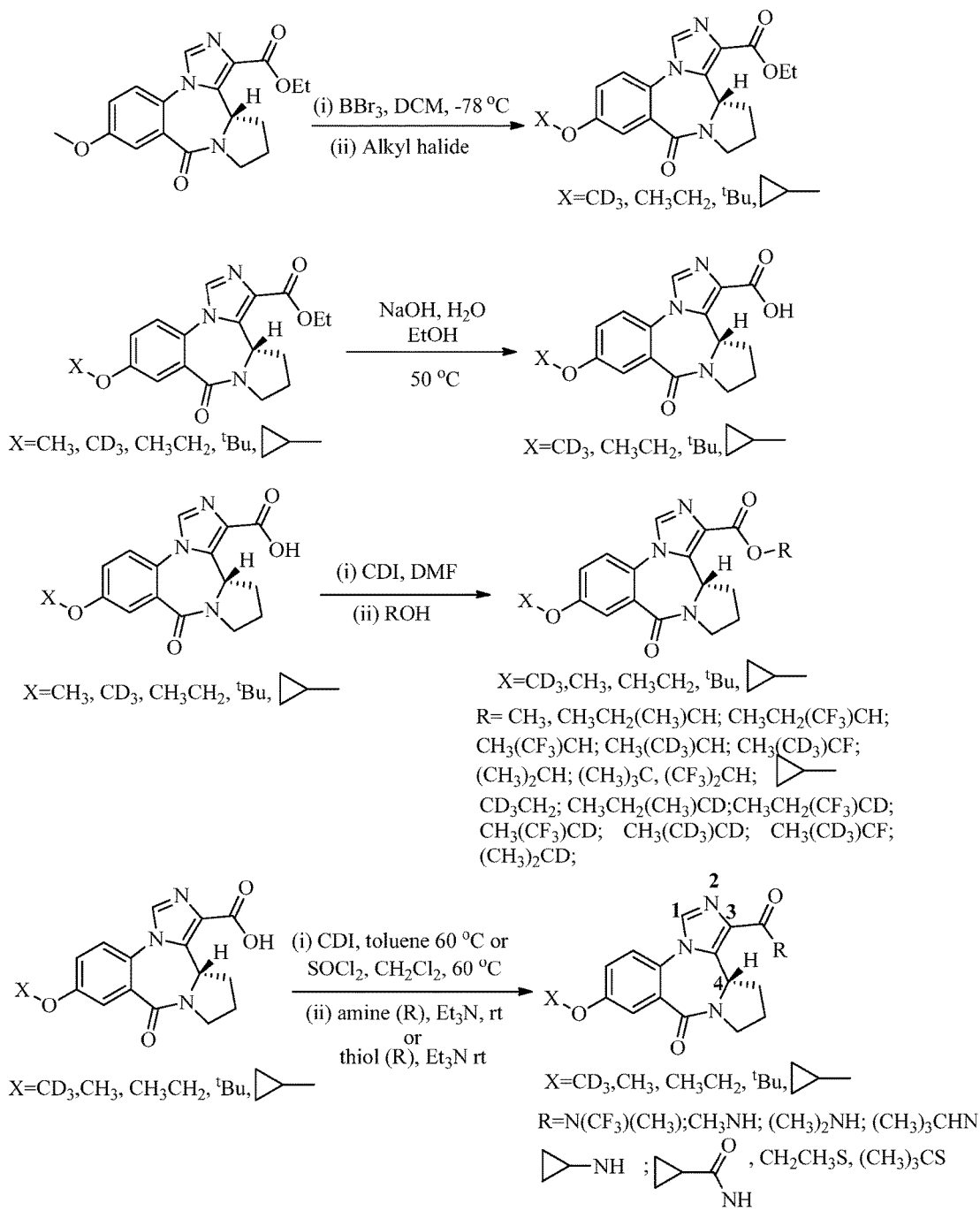
FIG. 14 shows various synthetic schemes for compounds of the present invention.
Figure 15:
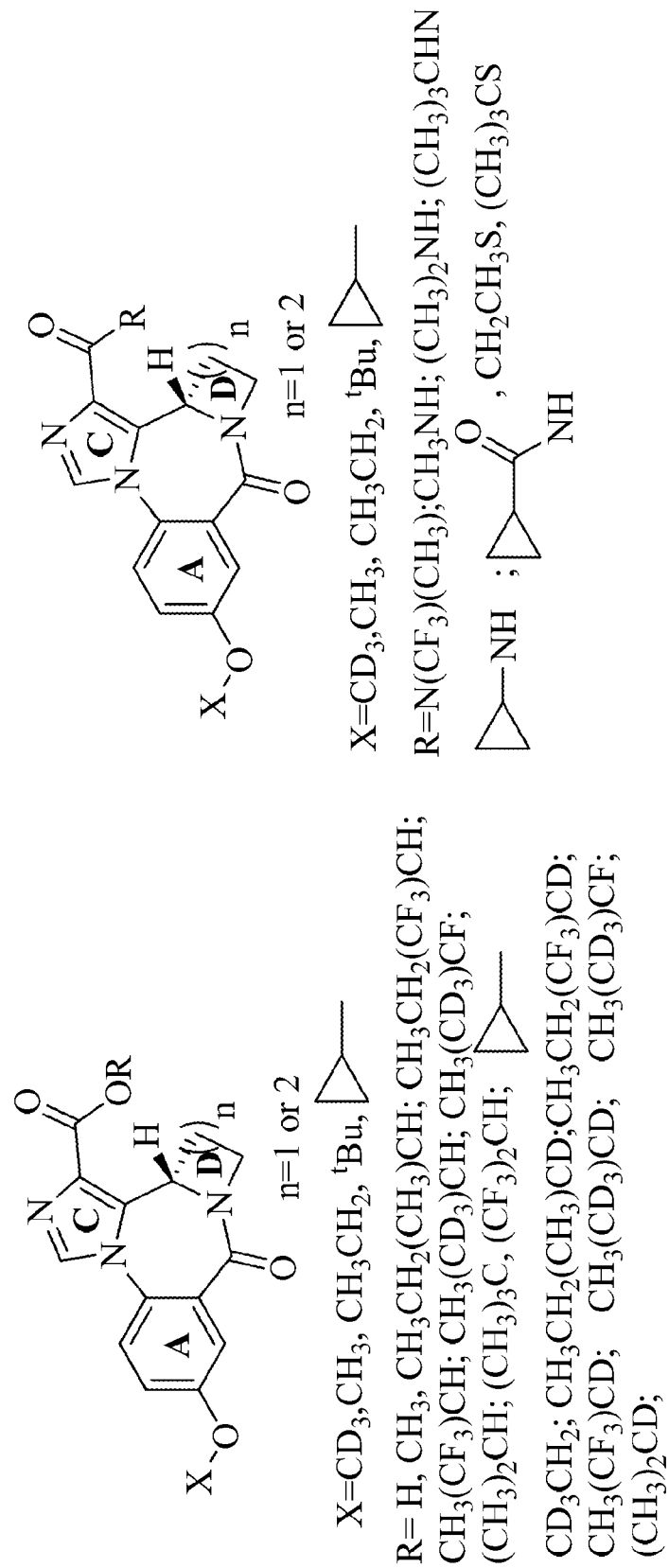
FIG. 15 shows various compounds according to the present invention.

Various routes to compounds of the present invention are shown in FIG. 14.

Other methods of synthesizing the compounds of the formulae herein will be evident to those of ordinary skill in the art. Synthetic chemistry transformations and protecting group methodologies (protection and deprotection) useful in synthesizing the compounds are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

Evaluation of Compounds

Compounds may be analyzed using a number of methods, including receptor binding studies and in vivo methods.

For example, the GABA$_A$ subunit selectivity of compounds can be evaluated, for example, using competitive binding assays. Such assays have been described (Choudhary et al. *Mol Pharmacol.* 1992, 42, 627-33; Savić et al. *Progress in Neuro-Psychopharmacology & Biological Psychiatry*, 2010, 34, 376-386). The assays involve the use of a radiolabeled compound known to bind to GABA$_A$ receptors, such as [$^3$H]flunitrazepam. Membrane proteins can be harvested and incubated with the radiolabeled compound, and non-specific binding can be evaluated by comparing binding of the radiolabeled compound to another, non-labeled compound (e.g., diazepam). Bound radioactivity can be quantified by liquid scintillation counting. Membrane protein concentrations can be determined using commercially available assay kits (e.g., from Bio-Rad, Hercules, Calif.).

Compounds can also be evaluated in electrophysiological assays in *Xenopus* oocytes. Compounds can be preapplied to the oocytes before the addition of GABA, which can then be coapplied with the compounds until a peak response is observed. Between applications, oocytes can be washed to ensure full recovery from desensitization. For current measurements, the oocytes can be impaled with microelectrodes, and recordings performed using voltage clamps.

Compounds described herein may be $GABA_A$ receptor ligands which bind to endogenous airway smooth muscle $GABA_A$ receptors and potentiate α-adrenoceptor-mediated relaxation. This is due to increased targeting for the benzodiazepine allosteric modulatory sites at the α4 and α5 subunits. The compounds may possess at least 2-fold, suitably at least 5-fold, and advantageously at least a 10-fold, selective efficacy for the $GABA_A/\alpha 4$ and/or $GABA_A/\alpha 5$ allosteric modulatory sites relative to those $GABA_A/\alpha 1$, $GABA_A/\alpha 2$, and $GABA_A/\alpha 3$. However, compounds which are not selective for the benzodiazepine allosteric modulatory binding sites on $GABA_A/\alpha 4$ and/or $GABA_A/\alpha 5$ receptors are also encompassed within the scope of the present invention. Such compounds will desirably exhibit functional selectivity by demonstrating decreased efficacy at the benzodiazepine allosteric modulatory sites of other $GABA_A$ receptors.

A selective or preferential therapeutic agent has less binding affinity or efficacy to the other benzodiazepine allosteric modulatory sites on $GABA_A$ receptors as compared to the benzodiazepine allosteric modulatory sites on the $GABA_A/\alpha 4$ or $GABA_A/\alpha 5$ subunits. Alternatively, the agent targets benzodiazepine allosteric modulatory sites on all $GABA_A$ receptors with a comparable affinity but exerts preferential efficacy for the benzodiazepine allosteric modulatory sites on $GABA_A/\alpha 4$ and $GABA_A/\alpha 5$ receptors compared to those on other $GABA_A$ receptors. A selective agent of the present invention can also have a greater or lesser ability to bind benzodiazepine allosteric modulatory sites on other $GABA_A$ receptors relative to $GABA_A/\alpha 2$ and $GABA_A/\alpha 3$ receptors.

Other methods for evaluating compounds are known to those skilled in the art. To assess a compound's undesirable side effects (toxicity), animals may monitored for overt signs of impaired neurological or muscular function. In mice, the rotorod procedure (Dunham, M. S. et al. *J. Amer. Pharm. Ass. Sci. Ed.* 1957, 46, 208-209) is used to disclose minimal muscular or neurological impairment. When a mouse is placed on a rod that rotates at a speed of 6 rpm, the animal can maintain its equilibrium for long periods of time. The animal is considered toxic if it falls off this rotating rod three times during a 1-min period. In rats, minimal motor deficit is indicated by ataxia, which is manifested by an abnormal, uncoordinated gait. Rats used for evaluating toxicity are examined before the test drug is administered, since individual animals may have peculiarities in gait, equilibrium, placing response, etc., which might be attributed erroneously to the test substance. In addition to MMI, animals may exhibit a circular or zigzag gait, abnormal body posture and spread of the legs, tremors, hyperactivity, lack of exploratory behavior, somnolence, stupor, catalepsy, loss of placing response and changes in muscle tone.

Compositions and Routes of Administration

In another aspect, the invention provides pharmaceutical compositions comprising one or more compounds of this invention in association with a pharmaceutically acceptable carrier. Such compositions may be in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. It is also envisioned that compounds may be incorporated into transdermal patches designed to deliver the appropriate amount of the drug in a continuous fashion. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture for a compound of the present invention, or a pharmaceutically acceptable salt thereof. When referring to these preformulation compositions as homogeneous, it is meant that the active ingredient is dispersed evenly throughout the composition so that the composition may be easily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example, 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer, which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compositions of the present invention may be incorporated for administration orally or by injection include aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Suitable dosage level is about 0.01 to 250 mg/kg per day, about 0.05 to 100 mg/kg per day, or about 0.05 to 5 mg/kg per day. The compounds may be administered on a regimen of 1 to 4 times per day, or on a continuous basis via, for example, the use of a transdermal patch.

Pharmaceutical compositions for enteral administration, such as nasal, buccal, rectal or, especially, oral administration, and for parenteral administration, such as intravenous, intramuscular, subcutaneous, peridural, epidural or intrathecal administration, are suitable. The pharmaceutical compositions comprise from approximately 1% to approximately 95% active ingredient, or from approximately 20% to approximately 90% active ingredient.

For parenteral administration including intracoronary, intracerebrovascular, or peripheral vascular injection/infusion preference is given to the use of solutions of the subunit selective GABAA receptor agonist, and also suspensions or dispersions, especially isotonic aqueous solutions, dispersions or suspensions which, for example, can be made up shortly before use. The pharmaceutical compositions may be sterilized and/or may comprise excipients, for example preservatives, stabilizers, wetting agents and/or emulsifiers, solubilizers, viscosity-increasing agents, salts for regulating osmotic pressure and/or buffers and are prepared in a manner known per se, for example by means of conventional dissolving and lyophilizing processes.

For oral pharmaceutical preparations suitable carriers are especially fillers, such as sugars, for example lactose, saccharose, mannitol or sorbitol, cellulose preparations and/or calcium phosphates, and also binders, such as starches, cellulose derivatives and/or polyvinylpyrrolidone, and/or, if desired, disintegrators, flow conditioners and lubricants, for example stearic acid or salts thereof and/or polyethylene glycol. Tablet cores can be provided with suitable, optionally enteric, coatings. Dyes or pigments may be added to the tablets or tablet coatings, for example for identification purposes or to indicate different doses of active ingredient. Pharmaceutical compositions for oral administration also include hard capsules consisting of gelatin, and also soft, sealed capsules consisting of gelatin and a plasticizer, such as glycerol or sorbitol. The capsules may contain the active ingredient in the form of granules, or dissolved or suspended in suitable liquid excipients, such as in oils.

Transdermal application is also considered, for example using a transdermal patch, which allows administration over an extended period of time, e.g. from one to twenty days.

Methods of Use

The present invention provides a method of reducing airway constriction comprising administering an effective amount of a GABAergic agent having reduced benzodiazepine-type CNS effects to a subject in need thereof. In some embodiments, the GABAergic agent is a compound of formulae (I), (II) and (III). In some embodiments, airway constriction occur during anesthesia.

The present invention further provides a method of reducing lung inflammation comprising administering an effective amount of a GABAergic agent having reduced benzodiazepine-type CNS effects to a subject in need thereof. In some embodiments, the GABAergic agent is a compound of formulae (I), (II) and (III). In some embodiments, the lung inflammation is associated with asthma, chronic obstructive pulmonary disease, emphysema, cystic fibrosis, pulmonary fibrosis, bronchiectasis, fibrosing alveolitis, Wegener's granulomatosis, intrinsic alveolitis or infection. The infection is suitably caused by viral, bacterial and/or fungal agents.

Lung inflammation may be evidenced in a patient by impaired pulmonary function, shortness of breath, especially with exertion or exercise, coughing, or labored breathing. A wide variety of diagnostic tools, including chest x-rays, CT scans, and pulmonary function tests are used to diagnose inflammatory lung disease. Pulmonary function and exercise tests may be used to determine lung capacity impaired by inflammation. Tissue samples from the lungs can be obtained for more definite diagnosis of inflammation. This can be obtained with a bronchoscopy (transbronchial biopsy) or bronchoalveolar lavage or surgical lung biopsy. Histologically, inflammation may reveal increased numbers of macrophages, lymphocytes, or polymorphonuclear cells in sputum and bronchoalveolar lavage fluid or lung parenchema or airways. Migration and activation of immune/inflammatory cells to the lung is regulated by a variety of different mediators, including proteases, cytokines, and chemokines secreted by a variety of inflammatory and resident cells.

In another aspect, the present invention provides a method of reducing the development of disease in subjects having risk factors associated with lung inflammation. An effective amount of a GABAergic agent having reduced benzodiazepine-type CNS effects is administered to a subject in need thereof. Suitably, the GABAergic agent is a compound of formulae (I), (II) and (III).

A number of factors may increase the likelihood of developing inflammatory lung diseases: low birth weight, having a blood relative with a condition such as asthma (thus a genetic predisposition), the presence of specific gene mutations (such as in CFTR genes), obesity, smoking or exposure to smoke (including in-utero exposure), exposure to exhaust fumes or other types of environmental pollution, or exposure industrial or agricultural chemicals.

In some embodiments, the lung inflammation is associated with asthma, chronic obstructive pulmonary disease, emphysema, cystic fibrosis, pulmonary fibrosis, bronchiectasis, fibrosing alveolitis, Wegener's granulomatosis, intrinsic alveolitis or infection. The infection is suitably caused by viral, bacterial and/or fungal agents.

The present invention also provides a method of treating a lung disease comprising administering an effective amount of a GABAergic agent having reduced benzodiazepine-type CNS effects to a subject in need thereof. In some embodiments, the GABAergic agent is a compound of formulae (I), (II) and (III). In some embodiments, the lung disease is selected from asthma, chronic obstructive pulmonary disease, emphysema, cystic fibrosis, pulmonary fibrosis, bronchiectasis, fibrosing alveolitis, Wegener's granulomatosis, intrinsic alveolitis or infection. The infection is suitably caused by viral, bacterial and/or fungal agents.

The present invention further provides a method of reducing inflammation in a subject having an autoimmune disease comprising administering an effective amount of a GABAergic agent having reduced benzodiazepine-type CNS effects to a subject in need thereof. In some embodiments, the GABAergic agent is a compound of formulae (I), (II) and (III). In some embodiments, the autoimmune disease is selected from arthritis, diabetes, lupus and Crohn's disease.

The following non-limiting examples are intended to be purely illustrative of some aspects and embodiments, and show specific experiments that were carried out in accordance with the disclosure.

EXAMPLES

Statistical Analysis. Each experimental permutation included intra-experimental controls. Where appropriate, repeated measures in a one way ANOVA were employed using Bonferroni posttest comparisons. In addition, dose response curves were evaluated using a sigmoidal dose response analysis function in Prism 4.0 software (GraphPad San Diego Calif.) which employs a four-parameter logistic equation according to the Hill model: $Y=\text{minimum}+(E_{max}-\text{minimum})/(1+10(\text{dose}-\log EC_{50}))$, where the minimum represents the initial resting muscle tension. In cases where only 2 experimental groups were being compared a two tailed student t test was employed. Data is presented as mean±SEM; $p<0.05$ in all cases was considered significant.

Animal Studies. All animal studies were approved by Columbia University's Institutional Animal Care and Use Committee.

EXAMPLE 1

Synthesis of ethyl(S)-11,12,13,13a-tetrahydro-7-methoxy-9-oxo-9H-imidazo [1,5-α]pyrrolo[2,1-c][1,4]benzo-diazepine-1-carboxylate (6)

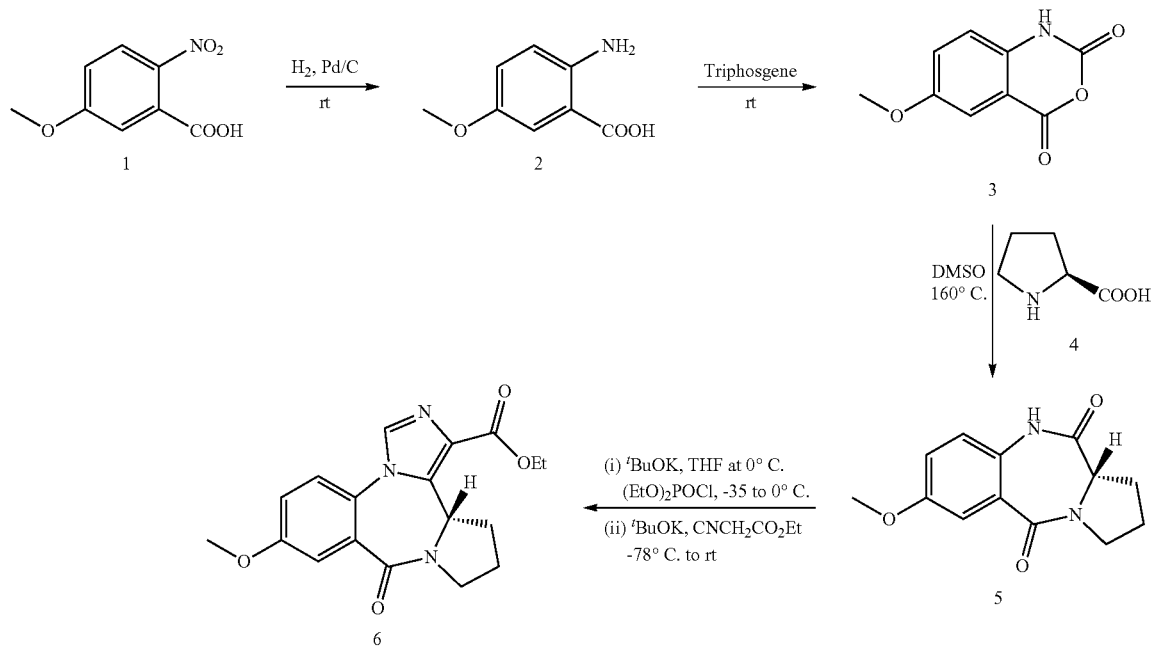

5-Methoxy anthranilic acid (2): To a solution of 2-nitro-5-methoxybenzoic acid 1 (25.0 g, 126 mmol) in ethyl acetate (600 mL), Pd on carbon (10%, 1.5 g) was added. The reaction flask was evacuated, after which an atmosphere of argon was filled over the solution, followed by $H_2$ employed with a balloon (repeated 3 times to make sure that the solution was saturated with $H_2$). The reaction mixture was stirred at ambient temperature for 6 h. After the completion of the reaction (TLC, silica gel), the solution was filtered over a bed of celite to remove the Pd. The solids were washed with ethyl acetate. The solvent was removed under reduced pressure to yield 2 as a yellow solid in 96% yield. M.p. 147-149° C.; $^1$H NMR (300 MHz, $CDCl_3$) δ 3.66 (s, 3H), 6.71 (d, 1H, J=9.0 Hz), 6.94 (dd, 1H, J=9.0 Hz, 3.0 Hz), 7.19 (d, 1H, J =3.0 Hz), 8.40 (bs, 2H). This material was used directly in the next experiment.

5-Methoxyisotic anhydride (3). The 5-methoxyanthranilic acid 2 (15.0 g, 89.6 mmol) was dissolved in a mixture of $H_2O$ (800 mL) and conc hydrochloric acid (6 mL), followed by the addition of triphosgene (39.8 g, 134.6 mmol). The contents were stirred at ambient temperature for 3-4 h until the completion of the reaction (TLC, silica gel). A white solid precipitated out of the solution after completion. The solids were collected by filtration and washed with $H_2O$ (2 L). The solids were dried under vacuum to give pure 3 in 83% (14.7 g) yield. M.p. 237-239° C.; $^1$H NMR (300 MHz, $CDCl_3$) δ 3.65 (s, 3H), 7.11 (d, 1H, J=8.9 Hz), 7.35 (dd, 1H, J=8.9 Hz, 2.7 Hz), 7.19 (d, 1H, J=2.7 Hz), 11.61 (bs, 1H). This material was used directly in the next experiment.

(S)-2,3-Dihydro-7-methoxy-1H-pyrrolo[2,1-c][1,4]benzodiazepine-5,11(10H,11aH)-dione (5): A mixture of 5-methoxyisotoic anhydride 3 (10.4 g, 53.8 mmol) and L-proline 4 (6.82 g, 59.2 mmol) in DMSO (70 mL) was heated with stirring at 160° C. for 2 h. The white turbid reaction mixture became a clear brown solution as the temperature was increased above 80° C. After the completion of the reaction by TLC (silica gel), the solution was cooled to rt. It was poured into 100 mL of ice water to yield 5 as a white solid. The solids were collected by vacuum filtration, washed with ice cold water (2×20 mL). The filtrate was extracted with ethyl acetate and the solvent was removed under reduced pressure to yield solid 5. The combined solids were dried in a vacuum oven at 80° C. for 4 h. The yield of 5 was 95% (11.0 g). M.p. 214-216° C.; $[α]_D^{25}$=+444.40 (c 1%, in $CH_2Cl_2$); $^1$H NMR (300 MHz, $CDCl_3$) δ 1.82-2.01 (m, 3H), 2.50-2.51 (m, 1H), 3.40-3.49 (m, 1H), 3.56-3.63 (m, 1H), 3.78 (s, 3H), 4.07-4.10 (m, 1H), 7.07 (d, 1H, J=8.7 Hz), 7.13 (dd, 1H, J=8.7 Hz, 3.0 Hz), 7.26 (d, 1H, J=3.0 Hz), 10.30 (bs, 1H). This material was used directly in the next experiment.

Ethyl(S)-11,12,13,13a-tetrahydro-7-methoxy-9-oxo-9H-imidazo[1,5-a]pyrrolo[2,1-c][1,4]benzo-diazepine-1-carboxylate (6): A well dried reaction flask was evacuated completely and flushed with argon. Then flask was charged with (S)-2,3-Dihydro-7-methoxy-1H-pyrrolo[2,1-c][1,4] benzodiazepine-5,11-(10H,-11aH)-dione 5 (10 g, 46.3 mmol)) in dry THF (200 mL). The turbid solution was cooled to 0° C. Potassium tert-butoxide (6.75 g, 60.2 mmol) was added to the flask and the solution was stirred for 40 min at 0° C. Then diethyl chlorophosphate (11.2 g, 64.82 mmol) was slowly added to the reaction mixture at −35° C. and it was allowed to stir at 0° C. over a period of 1 h. The cloudy reaction mixture became a clear golden brown solution. A second portion of potassium tert-butoxide (0.675 g, 6.0 mmol) and diethyl chlorophosphate (1.12 g, 6.5 mmol) was added in a similar manner. The reaction mixture was stirred at 0° C. for 30 min. After complete consumption of the starting material 5 (TLC), the reaction was cooled to −78° C. after which ethyl isocyanoacetate (7.3 g, 64.82 mmol) and potassium tert-butoxide (6.75 g, 60.2 mmol) were added. The reaction mixture was stirred at rt for 8 h. The reaction was quenched with a saturated aq solution of NaHCO$_3$ (20 mL). The THF was removed under reduced pressure and the aq layer was extracted with CH$_2$Cl$_2$ (100 mL×3). The combined organic layer was separated and washed with a brine solution (100 mL) and dried (Na$_2$SO$_4$). The CH$_2$Cl$_2$ was removed under reduced pressure and the dark brown pasty liquid residue which resulted was washed with ether to yield crude 6. This crude solid was recrystallized in CH$_2$Cl$_2$ to yield 6 as a pure white solid in 54% (8.5 g) yield. M.p 195-197° C.; (Lit. report: 175-176° C.)[1]; [α]$_D^{25}$=+18.00 (c 0.5%, in CH$_2$Cl$_2$); $^1$H NMR (300 MHz, CDCl$_3$) δ 1.44 (t, 3H, J=7.2 Hz), 2.15-2.35 (m, 3H), 3.49-3.61 (m, 2H), 3.75-3.85 (m, 1H), 3.91 (s, 3H), 4.41 (q, 2H, J=7.2 Hz), 4.75 (d, 1H, J=6.9 Hz), 7.15 (dd, 1H, J=8.9 Hz, 3.0 Hz), 7.32 (d, 1H, J=8.9 Hz), 7.59 (d, 1H, J=3.0 Hz), 7.81 (s, 1H); $^{13}$C NMR (75 MHz, CDCl$_3$) δ 14.3, 24.3, 28.4, 46.6, 53.4, 55.8, 61.2, 114.5, 119.7, 124.6, 126.0, 127.3, 130.6, 135.8, 137.6, 159.4, 162.6, 163.7; HRMS (ESI) (M+Na)$^-$, calcd. for C$_{18}$H$_{19}$N$_3$O$_4$Na 364.1273; Found 364.1279.

EXAMPLE 2

Synthesis of (S)-11,12,13,13a-tetrahydro-7-methoxy-9-oxo-9H-imidazo[1,5-a]pyrrolo[2,1-c][1,4]benzodia-zepine-1-carboxylic acid (7)

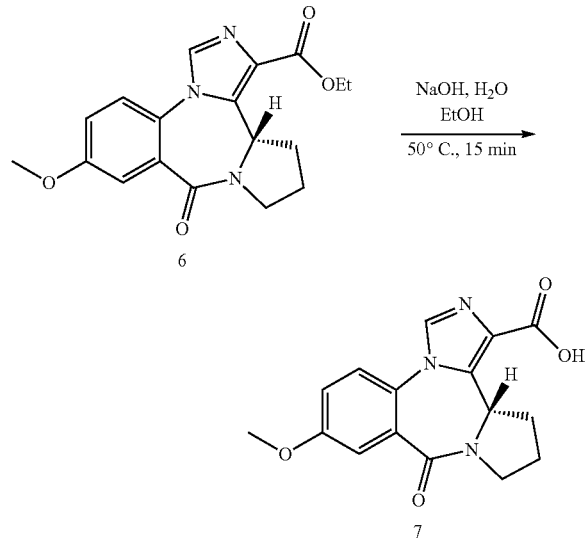

Ethyl(S)-11,12,13,13a-tetrahydro-7-methoxy-9-oxo-9H-imidazo[1,5-a]pyrrolo[2,1-c][1,4]benzo-diazepine-1-carboxylate 6 (2.12 g, 6.21 mmol) was dissolved in a mixture of EtOH (4 mL) and H$_2$O (3 mL) after which NaOH (1.2 g, 31.0 mmol) was added to the solution. This reaction mixture was heated to 50° C. for 15 min and the EtOH was removed under reduced pressure. The remaining aq solution was stirred at 0° C. for 10 min conc HCl was then added dropwise to the solution until the pH was 3-4 (pH paper). A pale yellow precipitate which formed was left in the solution and stirred at rt for 2 h. The solids of 7 were collected by filtration, washed with cold water (2×5 mL) and the aq layer also allowed to stand at rt for 10 h to yield additional 7. The combined solids were dried in a vacuum oven at 80° C. for 7 h to get pure 7 in 80% yield. M.p 210-211° C.; [α]$_D^{25}$=+8.00 (c 0.25%, in CH$_3$OH); $^1$H NMR (300 MHz, CDCl$_3$) δ 2.03-2.16 (m, 3H), 3.50-3.631 (m, 3H), 3.87 (s, 3H), 4.84 (d, 1H, J=7.5 Hz), 7.31 (dd, 1H, J=8.9 Hz, 3.0 Hz), 7.41 (d, 1H, J=3.0 Hz), 7.63 (d, 1H, J=8.9 Hz), 8.21 (s, 1H); $^{13}$C NMR (75 MHz, CDCl$_3$) δ 24.9, 28.7, 47.3, 53.6, 56.8, 115.3, 119.9, 126.7, 127.0, 128.6, 131.0, 137.5, 137.5, 159.5, 164.0, 165.3; HRMS (ESI) (M+H)$^+$, calcd. for C$_{16}$H$_{16}$N$_3$O$_4$ 314.1141; Found 314.1141.

EXAMPLE 3

Synthesis of isopropyl(S)-11,12,13,13a-tetrahydro-7-methoxy-9-oxo-9H-imidazo[1,5-a]pyrrolo[2,1-c][1,4]-benzodiazepine-1-carboxylate (8)

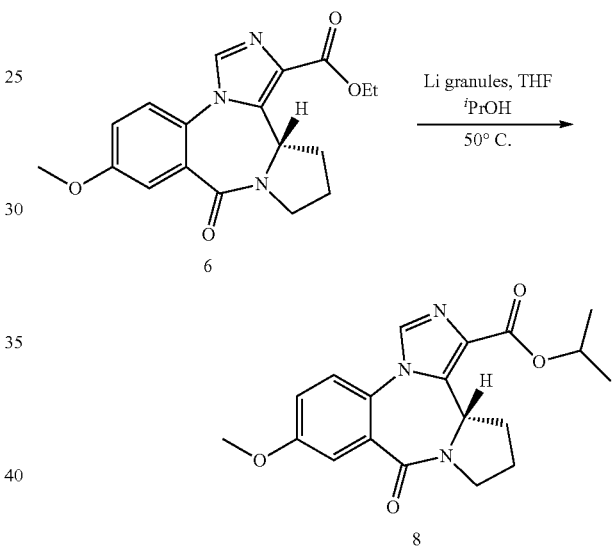

A heat dried reaction flask was evacuated completely and flushed with argon. Li granules (0.091 g, 13.2 mmol) were added to the dry THF solution (5 mL). Then dry iPrOH (1 mL, 13.2 mmol) was introduced into the flask using a syringe and the reaction mixture was heated to 50° C. and maintained at this temperature for 30 min. Ethyl(S)-11,12,13,13a-tetrahydro-7-methoxy-9-oxo-9H-imidazo[1,5-a]pyrro-lo[2,1-c][1,4]-benzodiazepine-1-carboxylate 6 (0.45 g, 1.32 mmol) was added to the above turbid solution and the reaction maintained at 50° C. for 20 min. After the completion of the reaction (TLC, silica gel), the flask was allowed to cool to rt and the THF removed under reduced pressure. Ice water (10 mL) was added to the residue and the solution was extracted with EtOAc. The organic layer was washed with water (2×10 mL) and brine (15 mL). The solvent was removed under reduced pressure to yield 8 as a solid in 80% yield. M.p 215-217° C.; (Lit. report: 153-154° C.)[1]; [α]D25=+8.00 (c 0.5%, in CH2Cl2); 1H NMR (300 MHz, CDCl3) δ 1.41-1.43 (m, 6H), 2.15-2.36 (m, 3H), 3.51-3.61 (m, 2H), 3.75-3.82 (m, 1H), 3.90 (s, 3H), 4.74 (d, 1H, J=7.2 Hz), 5.22-5.31 (m, 1H), 7.15 (dd, 1H, J=8.7 Hz, 3.0 Hz), 7.30 (d, 1H, J=8.7 Hz), 7.59 (d, 1H, J=3.0 Hz), 7.82 (s, 1H); 13C NMR (75 MHz, CDCl3) δ 21.8, 21.9, 24.4, 28.4, 46.6, 53.5, 55.9, 68.8, 114.5, 119.8, 124.7, 126.1, 127.7, 130.6, 135.9, 137.4, 159.5, 162.3, 163.7; HRMS (ESI) (M+Na)+, calcd. for C19H21N3O4Na 378.1430; Found 378.1424.

EXAMPLE 4

Synthesis of t-butyl(S)-11,12,13,13a-tetrahydro-7-methoxy-9-oxo-9H-imidazo [1,5-a]pyrrolo[2,1-c][1,4]-benzodiazepine-1-carboxylate 9

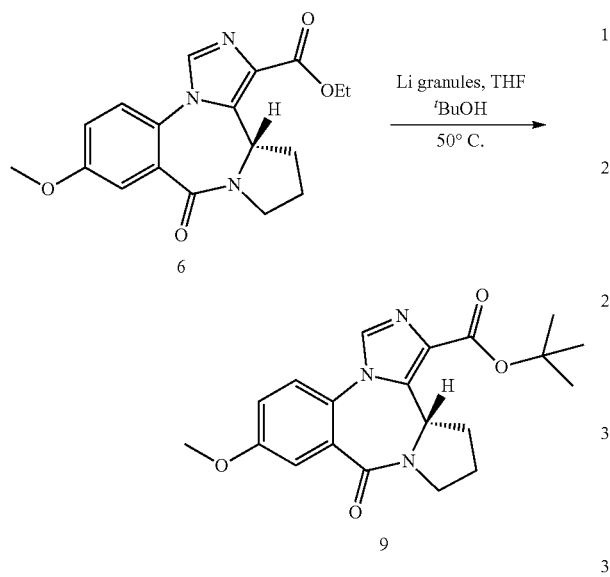

A well dried reaction flask was evacuated completely and back filled with argon and dry THF was added. Li granules (0.100 g, 14.6 mmol) were added to the dry THF solution (6 mL). Then dry $^t$BuOH (1.4 mL, 14.6 mmol) was introduced into the flask and the reaction mixture was heated to 50° C. and maintained at 50° C. for 30 min. Ethyl(S)-11,12,13,13 a-tetrahydro-7-methoxy-9-oxo-9H-imidazo[1,5-a]pyrro-lo [2,1-c][1,4]-benzodiazepine-1-carboxylate 6 (0.5 g, 1.46 mmol) was added to the above turbid solution and the reaction maintained at 50° C. for 20 min. After the completion of the reaction (TLC, silica gel), the flask was cooled to rt and the THF removed under reduced pressure. Ice water (10 mL) was added to the residue and it was then extracted with EtOAc. The organic layer was washed with water (2×10 mL) and brine solution (15 mL). The solvent was removed under reduced pressure and the residue was purified by flash column chromatography [silica gel, EtoAc/hexane (7:3)] to yield 9 as a solid in 30% yield. M.p 115-117° C. (119-121° C.)$^1$; $[\alpha]_D^{25}$=+36.00 (c 0.5%, in CH$_2$Cl$_2$); $^1$H NMR (300 MHz, CDCl$_3$) δ 1.63 (s, 9H), 2.14-2.33 (m, 3H), 3.47-3.59 (m, 2H), 3.74-3.81 (m, 1H), 3.90 (s, 3H), 4.73 (d, 1H, J=6.9 Hz), 7.14 (dd, 1H, J=8.8 Hz, 3.0 Hz), 7.30 (d, 1H, J=8.8 Hz), 7.57 (d, 1H, J=3.0 Hz), 7.83 (s, 1H); $^{13}$C NMR (75 MHz, CDCl$_3$) 6 24.4, 28.2, 28.4, 46.7, 53.5, 55.9, 82.0, 114.5, 119.8, 124.6, 126.2, 129.0, 130.6, 135.7, 136.5, 159.4, 162.3, 163.8; HRMS (ESI) (M+Na)$^+$, calcd. for C$_{20}$H$_{23}$N$_3$O$_4$Na 392.1586; Found 392.1574.

EXAMPLE 5

Synthesis of 1,1,1,3,3,3-hexafluoroprop-2-yl (S)-11,12,13,13a-tetrahydro-7-methoxy-9-oxo-9H-imidazo-[1,5-a]pyrrolo[2,1-c][1,4]-benzodiazepine-1-carboxylate (10)

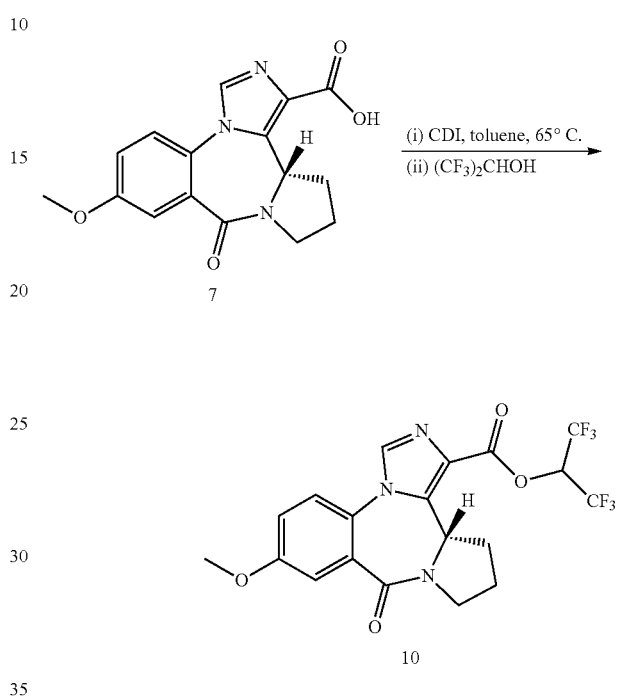

A mixture of (S)-11,12,13,13a-tetrahydro-7-methoxy-9-oxo-9H-imidazo[1,5-a]pyrrolo[2,1-c]-[1,4]-benzodiazepine-1-carboxylic acid (7) (0.15 g, 0.4 mmol), carbonyl diimidazole (0.093 g 0.48 mmol) and dry toluene (0.3 mL) were placed in a heat dried sealed tube. This suspension was allowed to stir at 65° C. for 1 h and then allowed to cool to rt. The absence of starting material was confirmed by TLC (silica gel). The solution cooled to 0° C. for 10 min and 1,1,1,3,3,3-hexafluoropropan-2-ol (0.75 mL, 6 mmol) was added to the suspension and the tube closed tightly. The suspension became a clear solution and the mixture was allowed to stir at rt for 2 h. The reaction was quenched with ice cold water (3 mL) and extracted with EtOAc (5 mL×2). The combined organic layer was washed with brine (5 mL). The solvent was removed under reduced pressure and the residue was purified by column chromatography [silica gel, EtOAc/hexane (1:1)] to yield pure 10 as a solid in 72% yield. M.p 204-205° C.; $[\alpha]_D^{25}$=+16.67 (c 0.3%, in CH$_2$Cl$_2$); $^1$H NMR (300 MHz, CDCl$_3$) δ 2.20-2.24 (m, 3H), 2.15-2.36 (m, 3H), 3.30-3.40 (m, 1H), 3.51-3.61 (m, 1H), 3.78-3.85 (m, 1H), 3.92 (s, 3H), 4.77 (d, 1H, J=7.2 Hz), 5.94-6.06 (sep, 1H, J=6.1 Hz), 7.15 (dd, 1H, J=8.8 Hz, 2.7 Hz), 7.33 (d, 1H, J=8.8 Hz), 7.61 (d, 1H, J=2.7 Hz), 7.89 (s, 1H); $^{13}$C NMR (75 MHz, CDCl$_3$) δ 24.3, 28.3, 46.6, 53.4, 55.9, 66.7, 114.7, 119.9, 124.3, 124.6, 125.6, 130.6, 136.8, 140.6, 159.4, 159.7, 163.6; HRMS (ESI) (M+Na)$^+$, calcd. for C$_{19}$H$_{15}$F$_6$N$_3$O$_4$Na 486.0864; Found 486.0875.

EXAMPLE 6

Synthesis of methyl (S)-11,12,13,13a-tetrahydro-7-methoxy-9-oxo-9H-imidazo -[1,5-a]pyrrolo-[2,1-c][1,4]-benzodiazepine-1-carboxylate (11)

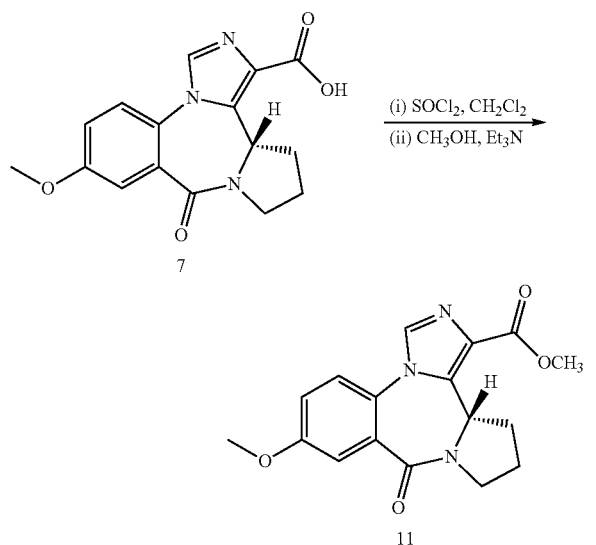

A mixture of (S)-11,12,13,13a-tetrahydro-7-methoxy-9-oxo-9H-imidazo[1,5-a]pyrrolo[2,1-c]-[1,4]-benzodiazepine-1-carboxylic acid (7) (0.1 g, 0.32 mmol), thionyl chloride (0.37 mL, 5.12 mmol) and dry CH2Cl2 (8 mL) were taken in a heat dried round bottomed flask under argon. This suspension was allowed to reflux at 60° C. for 1 h under an argon atmosphere. Then solution became a clear yellow color. The absence of starting material was confirmed by TLC (silica gel). The organic solvent and excess thionyl chloride were evaporated under reduced pressure. This evaporation was repeated a couple of times with dry CH2Cl2 (5 mL). Then the yellow residue which was obtained was dissolved in dry CH2Cl2 (10 mL) and this solution was cooled to 0° C. for 10 min under argon. A dry methanol solution (2 mL), followed by Et3N (0.2 mL, 1.6 mmol) was added to the reaction mixture and it was allowed to stir at rt for 7 h. After the completion of the reaction (TLC, silica gel) the solvent was removed under reduced pressure. The residue was quenched with ice cold water (5 mL) and extracted with CH2Cl2 (8 mL×2). The combined organic layer was washed with brine (5 mL). The solvent was removed under reduced pressure and the residue was purified by column chromatography [silica gel, EtoAc/hexane (7:3)] to yield pure 11 as a solid in 70% yield. M.p 180-182° C.; [α]D25=+8.00 (c 0.25%, in CH2Cl2); 1H NMR (300 MHz, CDCl3) δ 2.16-2.35 (m, 3H), 3.52-3.61 (m, 2H), 3.75-3.81 (m, 1H), 3.91 (s, 3H), 3.94 (s, 3H), 4.75 (d, 1H, J=6.9 Hz), 7.16 (dd, 1H, J=8.7 Hz, 2.7 Hz), 7.34 (d, 1H, J=8.7 Hz), 7.59 (d, 1H, J=2.7 Hz), 7.88 (s, 1H); 13C NMR (75 MHz, CDCl3) δ 24.4, 28.4, 46.6, 52.2, 53.4, 55.9, 114.5, 119.8, 124.7, 125.9, 126.9, 130.6, 135.9, 137.9, 159.5, 162.9, 163.7. HRMS (ESI) (M+Na)+, calcd. for C17H17N3O4Na 350.1117; Found 350.1125.

EXAMPLE 7

Synthesis of N-cyclopropyl (S)-11,12,13,13a-tetrahydro-7-methoxy-9-oxo-9H-imidazo -[1,5-a]pyrrolo-[2,1-c][1,4]-benzodiazepine-1-carboxamide (12)

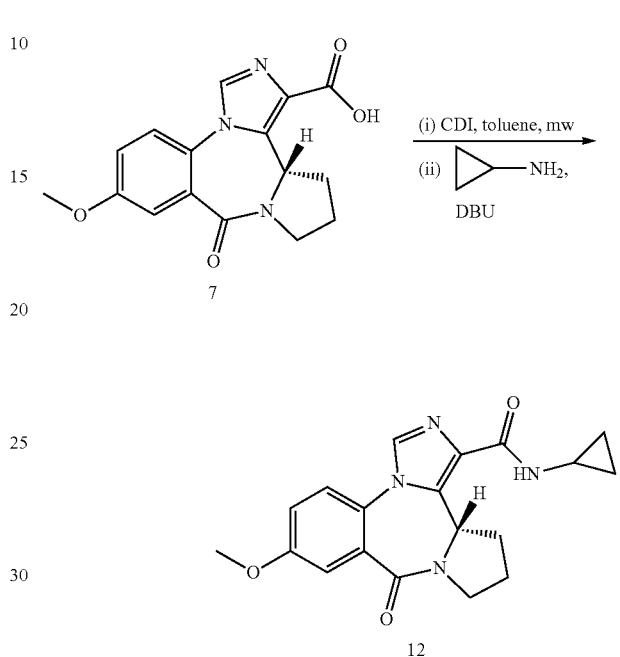

A mixture of (S)-11,12,13,13a-tetrahydro-7-methoxy-9-oxo-9H-imidazo[1,5-a]pyrrolo[2,1-c]-[1,4]-benzodiazepine-1-carboxylic acid (7) (0.1 g, 0.3 mmol), carbonyl diimidazole (0.057 g 0.33 mmol) and dry toluene (0.25 mL) were taken in a heat dried microwave boiling tube. This suspension was subjected to microwave irradiation for 2 min (1 min×2) at 100° C. The absence of starting material was confirmed by TLC (silica gel). The solution was cooled to 0° C. for 10 min. Cyclopropylamine (0.027 g, 0.45 mmol) and DBU (0.063 g, 0.4 mmol) were added to the suspension and the tube closed tightly. The suspension became a clear solution and the mixture was subjected to microwave irradiation for 1 min at 80° C. The reaction was quenched with ice cold water (3 mL) and extracted with EtOAc (5 mL×2). The combined organic layer was washed with brine (5 mL). The solvent was removed under reduced pressure and the residue was purified by column chromatography [silica gel, EtoAc/hexane (7:3)] to yield pure 12 as a solid in 55% yield. M.p 189-190° C.; [α]D25=−6.67 (c 0.3%, in CH2Cl2); 1H NMR (300 MHz, CDCl3) δ 0.61-0.66 (m, 2H), 0.82-0.88 (m, 2H), 2.17-2.24 (m, 2H), 2.31-2.43 (m, 1H), 2.81-2.89 (m, 1H), 3.49-3.59 (m, 1H), 3.74-3.88 (m, 2H), 3.91 (s, 3H), 4.71 (d, 1H, J=8.1 Hz), 7.15 (dd, 1H, J=8.7 Hz, 2.8 Hz), 7.26-7.30 (m, 1H), 7.59 (d, 1H, J=2.7 Hz), 7.65 (bs, 1H), 7.73 (s, 1H); 13C NMR (75 MHz, CDCl3) δ 6.5, 6.6, 22.3, 24.6, 28.8, 46.6, 53.6, 55.8, 114.4, 119.6, 124.4, 126.3, 130.0, 130.7, 134.5, 135.3, 159.3, 163.7, 163.8; HRMS (ESI) (M+Na)−, calcd. for C19H20N4O3Na 375.1433; Found 375.1440.

EXAMPLE 8

Synthesis of N-methyl (S)-11,12,13,13a-tetrahydro-7-methoxy-9-oxo-9H-imidazo-[1,5-a]pyrrolo-[2,1-c][1,4]-benzodiazepine-1-carboxamide (13)

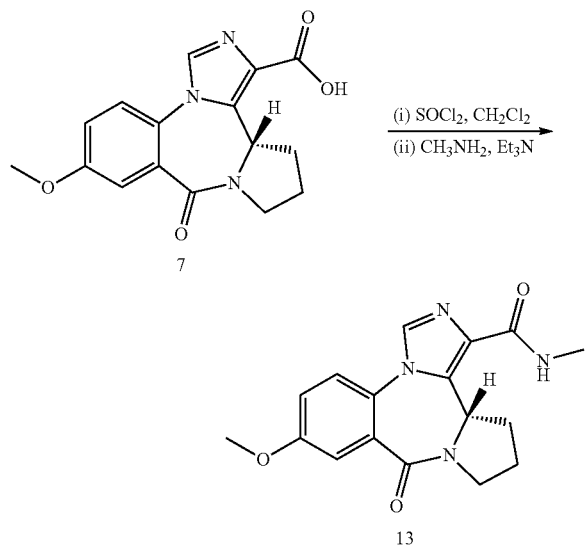

A mixture of (S)-11,12,13,13a-tetrahydro-7-methoxy-9-oxo-9H-imidazo[1,5-a]pyrrolo[2,1-c]-[1,4]-benzodiazepine-1-carboxylic acid 7 (0.17 g, 0.54 mmol), thionyl chloride (0.6 mL, 8.14 mmol) and dry $CH_2Cl_2$ (10 mL) were placed in a heat dried round bottomed flask under argon. This suspension was allowed to reflux at 60° C. for 1 h under argon atmosphere. Then solution became a clear yellow color. The absence of starting material was confirmed by TLC (silica gel). The organic solvent and excess thionyl chloride were evaporated under reduced pressure. This evaporation was repeated a couple of times with dry $CH_2Cl_2$ (5 mL). Then the yellow residue which was obtained was dissolved in dry $CH_2Cl_2$ (10 mL) and this solution was cooled to 0° C. for 10 min under argon. A solution of methylamine (33 wt % in absolute ethanol, 3 mL), followed by $Et_3N$ (0.3 mL, 2.5 mmol) was added to the reaction mixture and it was allowed to stir at rt for 7 h. After the completion of the reaction (TLC, silica gel) the solvent was removed under reduced pressure. The residue was quenched with ice cold water (5 mL) and extracted with $CH_2Cl_2$ (8 mL×3). The combined organic layer was washed with brine (5 mL). The solvent was removed under reduced pressure to yield pure 13 as a solid in 75% yield. M.p 180-182° C.; $[\alpha]_D^{25}$=+3.70 (c 0.5%, in $CH_2Cl_2$); $^1H$ NMR (300 MHz, $CDCl_3$) δ 2.13-2.24 (m, 2H), 2.30-2.41 (m, 1H), 2.97 (d, 1H, J=4.8 Hz), 3.49-3.59 (m, 1H), 3.74-3.88 (m, 2H), 3.91 (s, 3H), 4.72 (d, 1H, J=7.8 Hz), 7.14 (dd, 1H, J=8.7 Hz, 3.0 Hz), 7.29 (d, 1H, J=8.7 Hz), 7.49 (bs, 1H), 7.59 (d, 1H, J=3.0 Hz), 7.69 (s, 1H); $^{13}C$ NMR (75 MHz, $CDCl_3$) δ 24.6, 25.9, 28.8, 46.7, 53.6, 55.9, 114.4, 119.7, 124.5, 126.4, 130.5, 130.7, 134.6, 135.1, 159.3, 162.9, 163.8. HRMS (ESI) (M+Na)$^+$, calcd. for $C_{17}H_{18}N_4O_3Na$ 349.1277; Found 349.1300.

EXAMPLE 9

Synthesis of N,N-dimethyl (S)-11,12,13,13a-tetrahydro-7-methoxy-9-oxo-9H-imidazo-[1,5-a]pyrrolo-[2,1-c][1,4]-benzodiazepine-1-carboxamide (14)

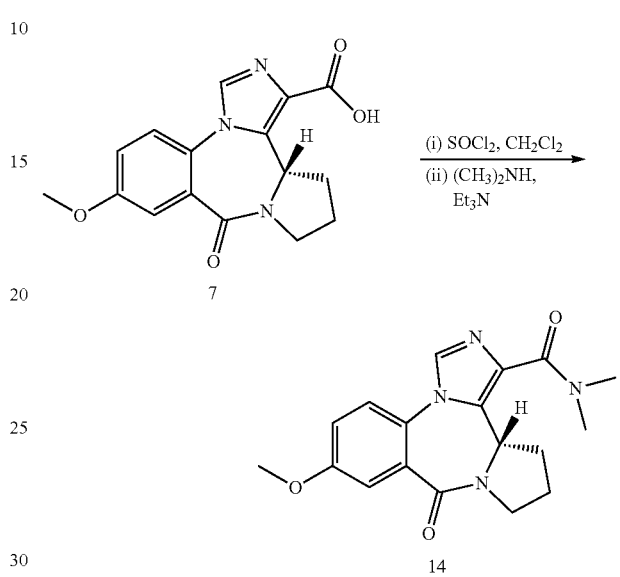

A mixture of (S)-11,12,13,13a-tetrahydro-7-methoxy-9-oxo-9H-imidazo[1,5-a]pyrrolo[2,1-c]-[1,4]-benzodiazepine-1-carboxylic acid (7) (0.15 g, 0.47 mmol), thionyl chloride (0.55 mL, 7.52 mmol) and dry $CH_2Cl_2$ (10 mL) were placed in a well heat dried round bottomed flask. This suspension was allowed to reflux at 60° C. for 1 h under argon. Then solution became a clear yellow color. The absence of starting material was confirmed by TLC (silica gel). The organic solvent and excess thionyl chloride were evaporated under reduced pressure. This evaporation was repeated couple of times with dry $CH_2Cl_2$ (5 mL). The yellow residue which was obtained was dissolved in dry $CH_2Cl_2$ (10 mL) and this solution was cooled to 0° C. for 10 min under argon. A solution of N,N-Dimethylamine (11% in ethanol, 5 mL), followed by $Et_3N$ (0.28 mL, 2.35 mmol) was added to the reaction mixture and it was allowed to stir at rt for 7 h. After the completion of the reaction (TLC silica gel) the solvent was removed under reduced pressure. The residue was quenched with ice cold water (5 mL) and extracted with $CH_2Cl_2$ (8 mL×3). The combined organic layer was washed with brine (5 mL). The solvent was removed under reduced pressure and the residue which resulted was subjected to purification by flash column chromatography [neutral alumina, 100% EtoAc] to yield pure 14 as a solid in 70% yield. M.p 186-188° C.; $[\alpha]D25$=+52.00 (c 0.25%, in $CH_2Cl_2$); 1H NMR (300 MHz, CDCl3) δ 2.01-2.08 (m, 2H), 2.25-2.38 (m, 1H), 2.89-2.94 (m, 1H), 3.08 (s, 3H), 3.14 (s, 3H), 3.63-3.82 (m, 2H), 3.90 (s, 3H), 4.73 (dd, 1H, J=8.4, 3.0 Hz), 7.15 (dd, 1H, J=8.9 Hz, 2.9 Hz), 7.34 (d, 1H, J=8.9 Hz), 7.57 (d, 1H, J=2.9 Hz), 7.97 (s, 1H); 13C NMR (75 MHz, $CDCl_3$) δ 23.9, 27.8, 35.3, 39.1, 47.2, 52.3, 55.8, 114.9, 119.7, 124.2, 126.1, 130.1, 131.0, 132.0, 134.8, 159.1, 164.2, 165.7. HRMS (ESI) (M+H)$^+$, calculated for $C_{18}H_{21}N_4O_3$ 341.1614; found 341.1629.

EXAMPLE 10

Synthesis of S-ethyl (S)-11,12,13,13a-tetrahydro-7-methoxy-9-oxo-9H-imidazo -[1,5-a]pyrrolo-[2,1-c][1,4]-benzodiazepine-1-carboxylate (15)

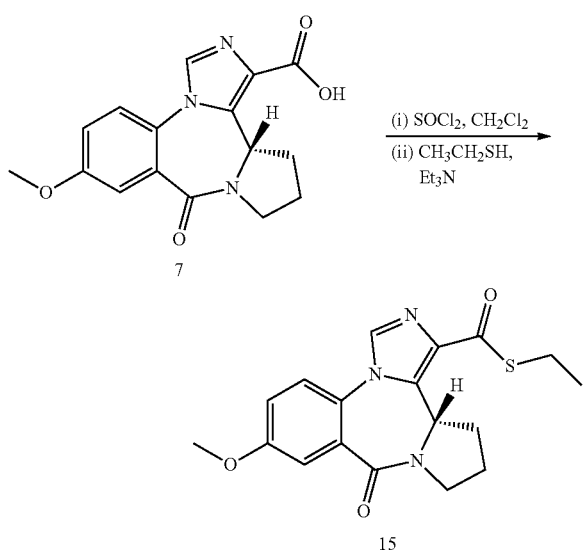

A mixture of (S)-11,12,13,13a-tetrahydro-7-methoxy-9-oxo-9H-imidazo[1,5-a]pyrrolo[2,1-c]-[1,4]-benzodiazepine-l-carboxylic acid (7) (0.15 g, 0.47 mmol), thionyl chloride (0.55 mL, 7.52 mmol) and dry $CH_2Cl_2$ (10 mL) were placed in a well heat dried round bottomed flask. This suspension was allowed to reflux at 60° C. for 1 h under argon. Then solution became a clear yellow color. The absence of starting material was confirmed by TLC (silica gel). The organic solvent and excess thionyl chloride were evaporated under reduced pressure. This evaporation was repeated couple of times with dry $CH_2Cl_2$ (5 mL). Then the yellow residue which was obtained was dissolved in dry $CH_2Cl_2$ (10 mL) and this solution was cooled to 0° C. for 10 min under argon. Ethanethiol (2 mL), followed by $Et_3N$ (0.28 mL, 2.35 mmol) was added to the reaction mixture and allowed to stir at rt for 7 h. After the completion of the reaction (TLC, silica gel), the solvent was removed under reduced pressure. The residue was quenched with ice cold water (5 mL) and extracted with $CH_2Cl_2$ (8 mL×3). The combined organic layer was washed with brine (5 mL). The solvent was removed under reduced pressure and the residue which resulted was subjected to purification on column chromatography [silica gel, EtoAc/hexane (8:2)] to yield pure 15 as a solid in 70% yield. M.p 228-230° C.; $[\alpha]_D^{25}$=−14.29 (c 0.28%, in $CH_2Cl_2$); $^1$H NMR (300 MHz, $CDCl_3$) δ 1.34 (t, 3H, J=7.5 Hz), 2.17-2.23 (m, 3H), 3.00 (q, 2H, J=7.5 Hz), 3.42-3.58 (m, 2H), 3.74-3.81 (m, 1H), 3.91 (s, 3H), 4.71 (d, 1H, J=7.2 Hz), 7.16 (dd, 1H, J=9.0 Hz, 2.9 Hz), 7.31 (d, 1H, J=9.0 Hz), 7.59 (d, 1H, J=2.9 Hz), 7.80 (s, 1H); $^{13}$C NMR (75 MHz, $CDCl_3$) δ 14.6, 23.0, 24.4, 28.6, 46.5, 53.3, 55.9, 114.5, 119.8, 124.5, 125.9, 130.6, 132.5, 134.6, 135.5, 159.5, 163.6, 188.1. HRMS (ESI) (M+H), calculated for $C_{18}H_{19}N_3O_3SNa$ 380.1045; found 380.1047.

EXAMPLE 11

Determination of Selectivity for α4-$GABA_AR$

Figure 12:
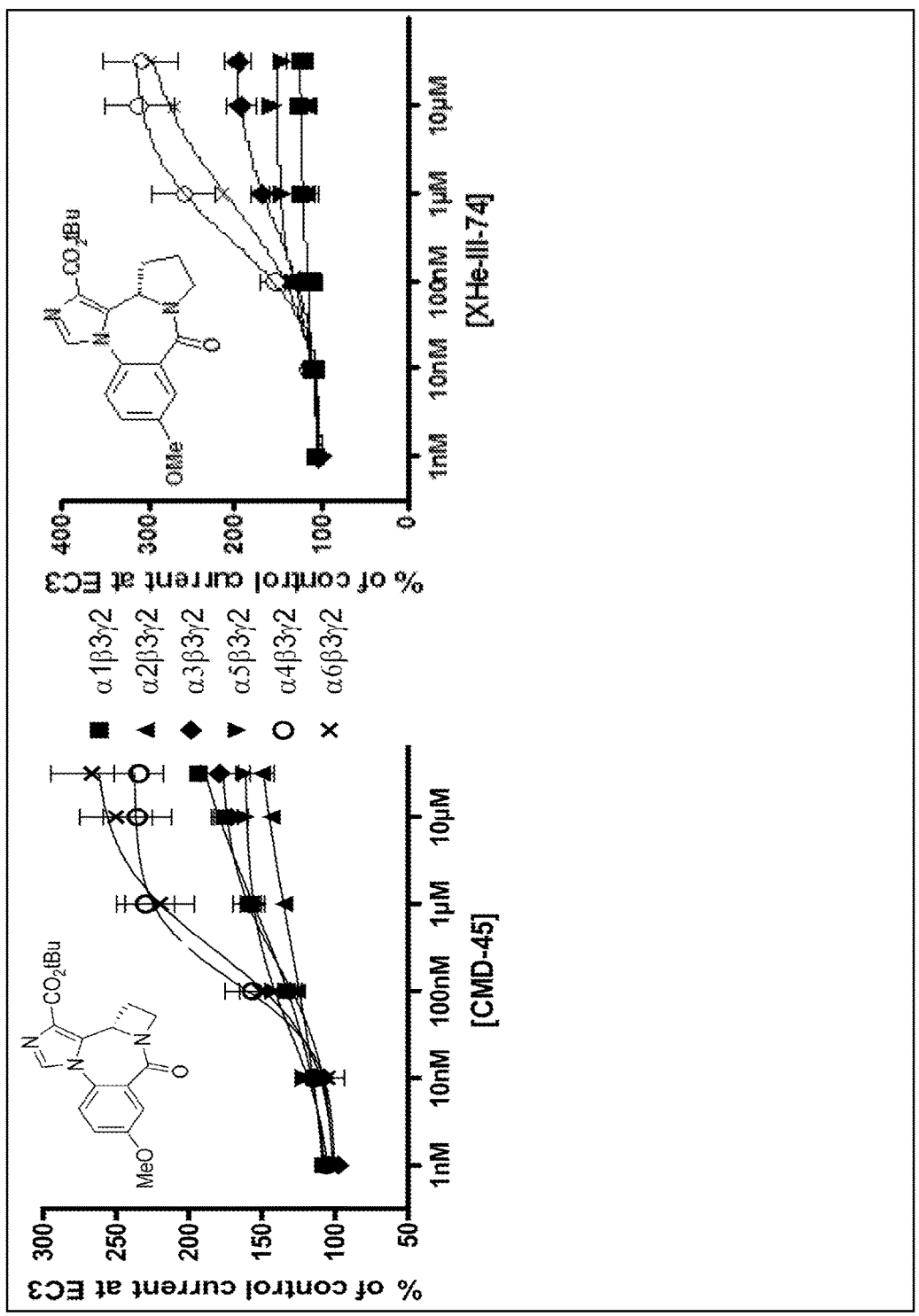
FIG. 12 shows compounds from that exhibit functional selectivity bias in favor of α4 or α6 $GABA_A R$. Selectivity is quantified by dose-response curves showing greater inward currents (i.e., agonist activity) by action of $GABA_A R$ bearing α4 or α6 compared to other α-subtypes.

Two compounds having selective activity bias for α4-$GABA_AR$ were identified (FIG. 12). Patch clamp assays were used to quantify chloride flux induced inward currents resulting from agonism of $GABA_AR$ containing single α-subunits. These results demonstrate the ability to finely discriminate functional activity of $GABA_AR$ receptor-ligand interactions. These studies also demonstrated efficacy of our compound CMD-45, a novel 8-methoxy imidazobenzodiazepine with selectivity bias in favor or α4 and α6-$GABA_AR$ (FIG. 12). These results support the hypothesis that targeting α4-containing $GABA_AR$ will elicit spontaneous ASM relaxation by overcoming contractile effects of a pure hyperpolarizing agent (tetraethylammonium) or G-coupled contractile agonist (substance P).

EXAMPLE 12

Figure 13:
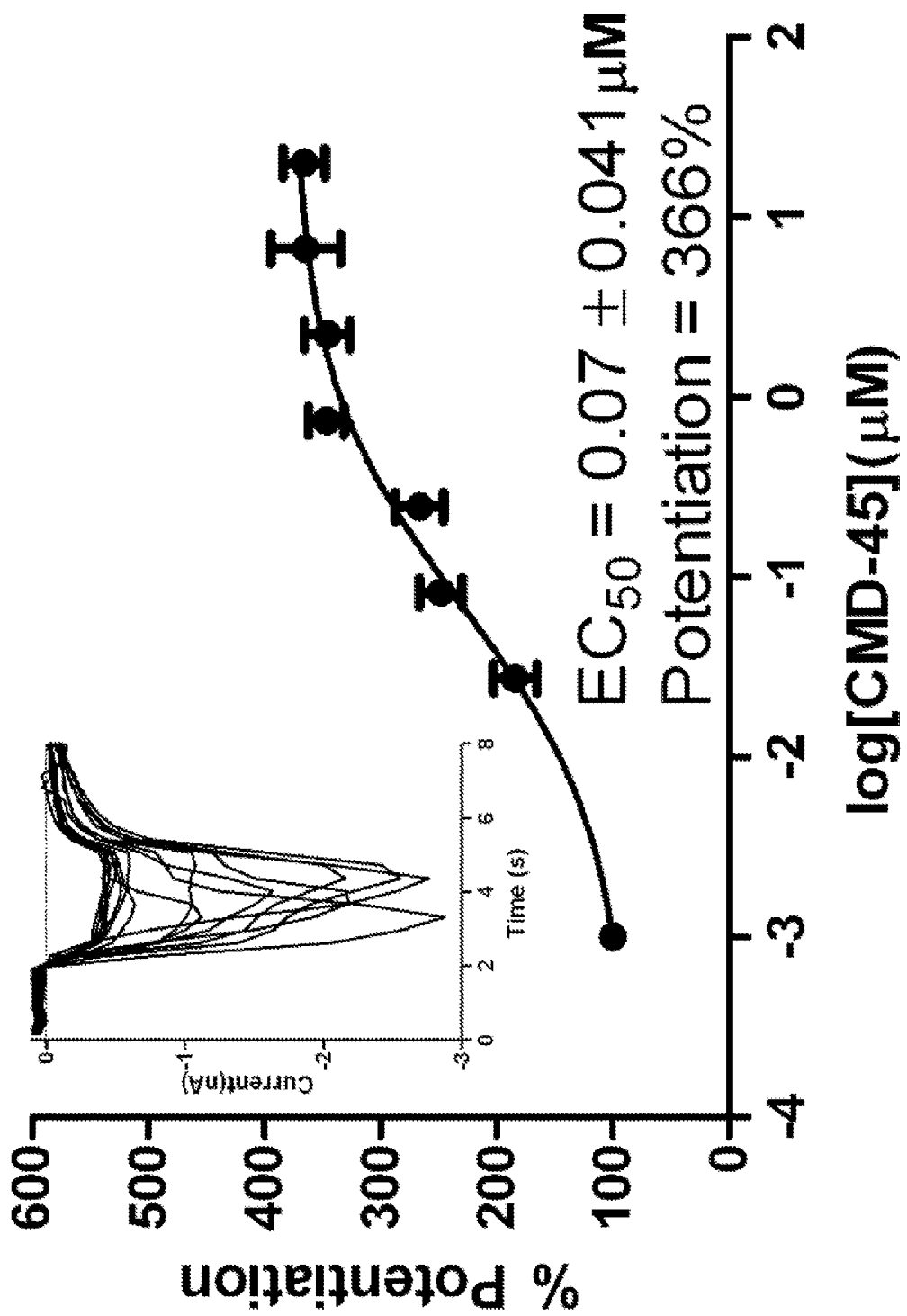
FIG. 13 shows membrane polarization effects of GABAA agonists CMD-45 and XHE(II)-074 on human Jurkat E6-1 cells. Inserts show inward rectifying currents (mA) at various doses. Compounds tested with 0.1 μM GABA. Curves show average of four determinations at indicated doses and standard deviations.
Figure 13:
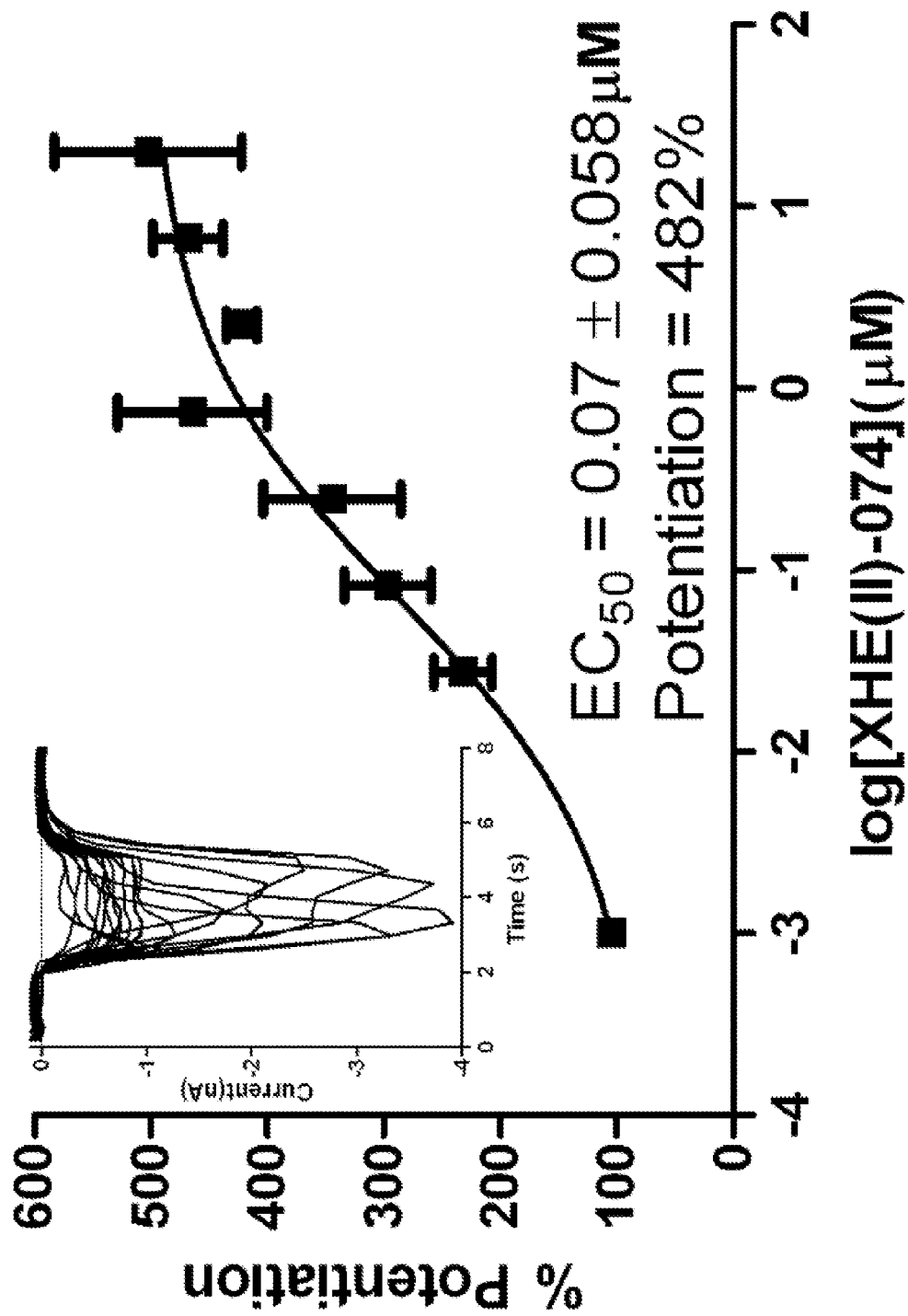

Membrane Polarization Effects of $GABA_A$ Agonists CMD-45 and XHE(II)-074 on Human Jurkat E6-1 Cells Both compounds were investigated using a CD4+ T-lymphocyte cell line (Jurkat E6-1) for potentiation of GABA using automated patch clamp (IonFlux). In contrast to manual patch clamp assays; this high throughput system enables dose dependent efficacy testing of more than 20 test conditions per day. In preliminary assay development studies, hyperpolarizing membrane dose-response signals can be generated upon exposure to CMD-45 or XHe-III-74 (α4-selective agonists) (FIG. 13).

Reference Example 1

Laser Capture Microdissection

Since pharmacologic targeting of airway smooth muscle $GABA_A$ subunits requires accurate subunit identification, laser capture microdissection (LCMD) was used to select airway smooth muscle cells devoid of surrounding epithelium, nerves, vascular structures, and fibroblasts for RNA isolation prior to RT-PCR analyses to provide greater assurance that our results were not contaminated by other cell types. Interspecies conservation of endogenous GABAA subunit expression was confirmed by comparing airway tissue from both guinea pig and human airways. Tracheal rings were embedded in OCT® compound followed cryopreservation using isopentane/dry ice. Frozen sections (6 um) were placed on a single 1 mm PEN-membrane coated slide (PALM Microlaser Technologies) and processed for RNA using a LCMD staining kit (Ambion AM1935). Histological confirmation of stained airway smooth muscle guided laser dissection, with only central portions of the airway smooth muscle layer being captured to minimize contamination from other cell types. Airway smooth muscle RNA was isolated using the Micro scale RNA isolation kit® (Ambion AM1931) and underwent RT-PCR using GABAA subunit specific primers that employed primer designs that flanked large genomic introns to distinguish mRNA from genomicderived PCR products. RNA from guinea pig and human brain served as positive controls and samples devoid of input cDNA (water blanks) served as negative controls.

Laser capture microdissection allowed for accurate sampling of only those cells displaying airway smooth muscle cell morphology from native tissue. Using gene specific primers we demonstrate restricted, yet abundant expression of mRNA encoding the α4 and α5 subunit (and no expression of mRNA encoding the other GABAA alpha subunits—results not shown). In addition, we also confirmed the presence of complimentary subunits (β, γ, δ) required to form α GABAA receptor of the typical extra-synaptic phenotype (FIG. 1). Since GABAA receptor a subunits present in airway smooth muscle cells qualitatively show concordance between human and guinea pig samples, this finding substantiates using guinea pig airway for functional organ bath studies.

Reference Example 2

Cultured Human Airway Smooth Muscle Cells

Human immortalized bronchial smooth muscle cell lines prepared as described were grown to confluence in M199 media (Gibco) containing 10% fetal bovine serum, 0.25 ng/ml epidermal growth factor, 1 ng/ml fibroblast growth factor, ITS supplement (1 mg/ml insulin, 0.55 mg/ml transferrin, 0.67 ug/ml sodium selenium) and antibiotics (100 units/ml penicillin G sodium, 100 µg/ml streptomycin sulfate, 0.25 µg/ml amphotericin B) in a humidified atmosphere of 5% $CO_2$/95% air at 37° C. Twenty four hours prior to study, cells were fed with serum and growth factor free media.

Reference Example 3

Preparation of Guinea Pig Tracheal Ring Organ Baths

Male Hartley guinea pigs (approximately 400 g) were anesthetized with intraperitoneal pentobarbital (100 mg/kg). Trachea were removed and dissected under a dissecting microscope into closed rings comprised of two cartilaginous segments. Epithelium was removed by gentle abrasion on the tracheal lumen with cotton. Tissues were placed into cold Krebs-Henseleit (KH) buffer (in mM: NaCl 118, KCl 5.6, $CaCl_2$ 0.5, $MgSO_4$ 0.24, $NaH_2PO_4$ 1.3, $NaHCO_3$ 25, glucose 5.6, pH 7.4) containing indomethacin 10 uM (DMSO final concentration in organ baths of 0.01%) to block tone due to endogenous release of prostanoids.

Tissues were hung in a water-jacketed (37° C.) 2-ml organ bath (Radnoti Glass Technology, Inc., Monrovia, Calif.) and attached to a Grass FT03 force transducer (Grass Telefactor, West Warwick, R.I.) coupled to a computer via BioPac hardware and Acqknowledge 7.3.3 software (Biopac Systems, Inc., Goleta, Calif.). KH buffer was continuously bubbled with 95% oxygen and 5% carbon dioxide and tissues were allowed to equilibrate at 1 g isotonic force for 1 hour with fresh KH buffer changes every 15 min.

EXAMPLE 13

$GABA_A$ α4-Selective Ligand CMD-45 Relaxation of an Acetylcholine (Ach) Induced Contraction in Murine Tracheal Rings Adult male C57/B16 wild type mice or adult male mice globally deficient in the GABAA a4 subunit (from Dr. Gregg Homanics, University of Pittsburgh) were euthanized with an overdose of sodium pentobarbital. Tracheas were rapidly removed and placed in modified Krebs-Henseleit buffer of the following composition in mM: 115 NaCl, 2.5 KCl, 1.91 $CaCl_2$, 2.46 $MgSO_4$, 1.38 $NaH_2PO_4$, 25 $NaHCO_3$, 5.56 D-glucose: pH 7.4 Connective tissue was removed under a dissecting microscope and tracheas were cut in half axially. One-half trachea was used in each chamber of a myograph bath (DMT: Ann Arbor, Mich.), one-half used for vehicle treatment and the other half used for drug (i.e. CMD-45) treatment. The tissue was held at a resting tension of 5 mN, at 37° C. with bubbled oxygenation (95% $O_2$/5% $CO_2$) and the buffer was exchanged every 15 minutes for 1 hour. Tension was continuously digitally recorded using BioPac hardware connected to Acknowledge software. Follow this equilibration period, 3 acetylcholine dose response curves were constructed (ACh; 100 mM-1 mM). An ACh ~EC50 was determined for each tracheal ring based on these dose response curves.

Figure 2:
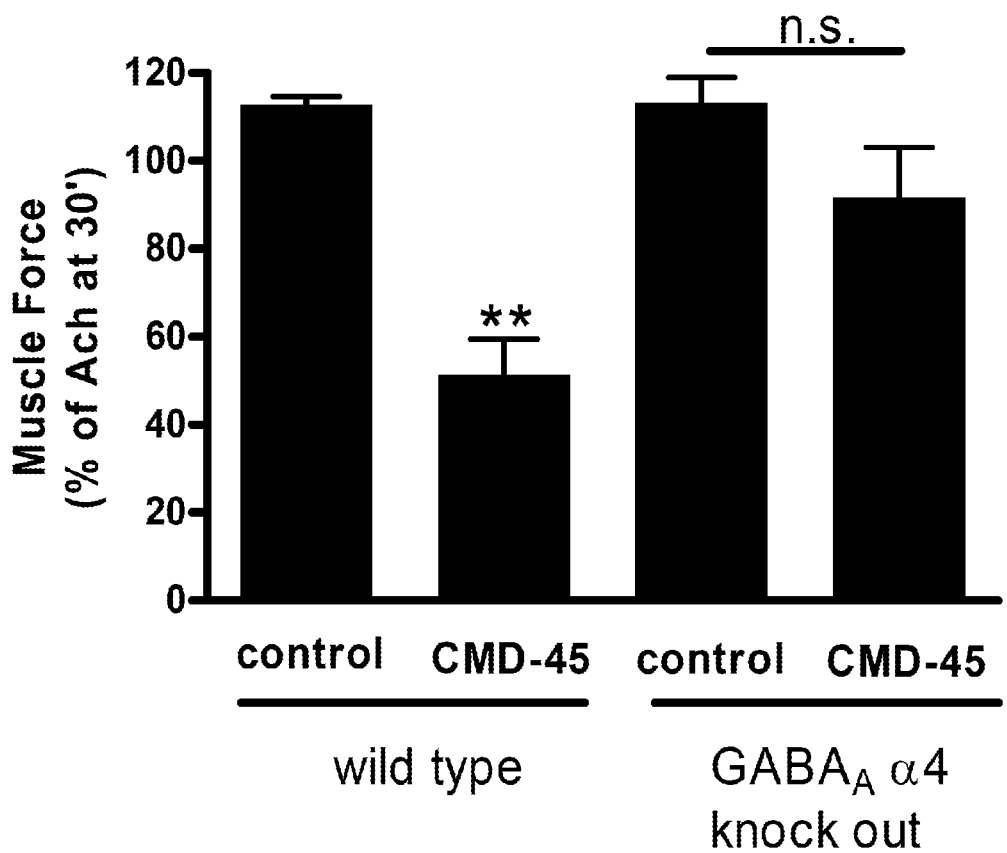
FIG. 2 shows $GABA_A$ α4-selective ligand CMD-45 relaxation of an acetylcholine (Ach) induced contraction in murine tracheal rings from wild-type but not $GABA_A$ α4 knockout mice. **p<0.01 compared to wild type vehicle control (0.1% DMSO). n=4.

In relaxation studies, tracheal ring were contracted to the determined ~EC50 and force was allowed to plateau. Single concentrations of vehicle (0.1% DMSO) or CMD-45 (100 uM) were added and continuous muscle force was measured over 30 minutes. The data are expressed as the percent of remaining tone at 30 minutes relative to the initial force achieved with the EC50 concentration of acetylcholine. Each 'n' represents a single tracheal segment from a single mouse. See FIG. 2.

EXAMPLE 14

Membrane Potential Fluorescent Assay

To determine whether activation of $GABA_A$ receptors induces membrane potential changes in cultured human airway smooth muscle cells the FLIPR in vitro fluorescent dye assay (Molecular Devices) was used. Human airway smooth muscle cells (prepared as described in Reference Examples 1 and 2) were grown to 100% confluence in 96 well black-walled plates and were washed with warmed (37° C.) low chloride buffer (consisting of in mM: 160 sodium-D-gluconate, 4.5 potassium-D-gluconate, 2 $CaCl_2$, 1 $MgCl_2$, 10 D-glucose, and 10 Hepes pH 7.4) four times. A stock solution (100% dye) of FLIPR blue dye was prepared by reconstitution of 1 vial (125 mg) with 100 ml of the low chloride buffer (assay buffer). A 50% working stock was prepared by further diluting the reconstituted blue dye 1:1 with assay buffer and was used to load cells (90 ul/well) over 20 minutes at 37° C. All reagents were dissolved in assay buffer. Baseline fluorescence was measured for 3 min prior to the first control additions (assay buffer). Three minutes later, airway smooth muscle cells were exposed to varying concentrations of THIP (0-10 mM) to determine a dose response. The fluorescence produced by membrane potential change following solution additions was quantified after subtracting changes induced by assay buffer alone. For subsequent antagonist assays, the first solution injected was either assay buffer, vehicle control (0.05% DMSO final), or the $GABA_A$ receptor antagonist picrotoxin (200 uM final) followed THIP (either 0.5 or 1 mM).

Figure 3A:
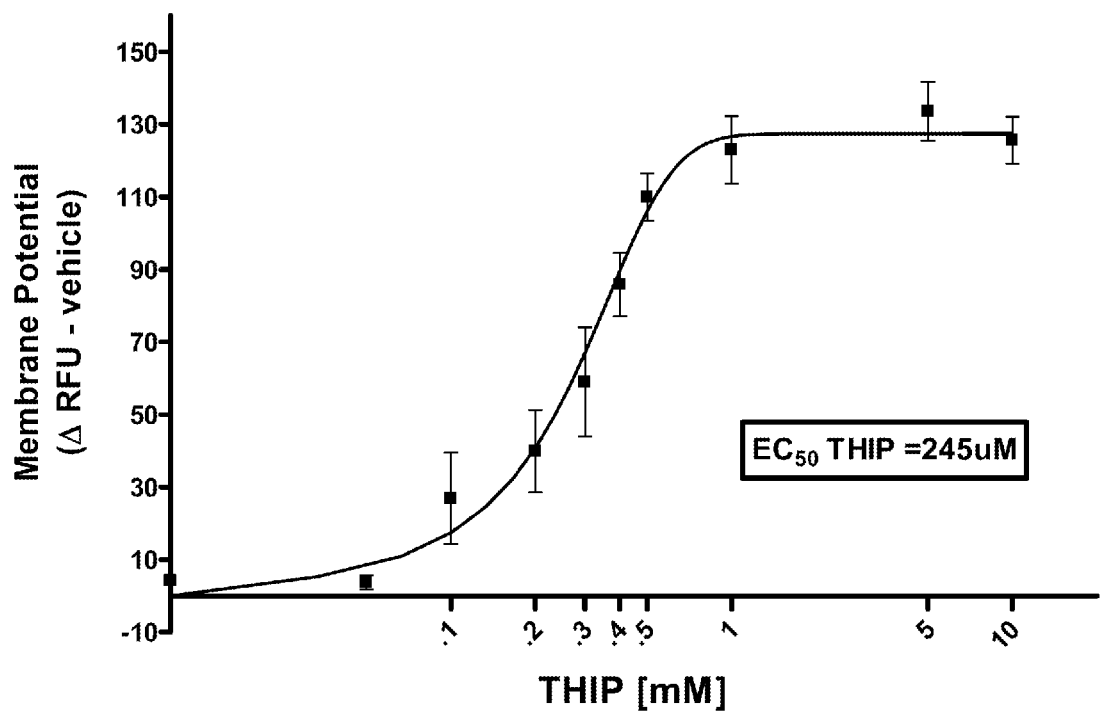
FIG. 3 shows (A) dose response curve of THIP (from 0 to 10 mM) eliciting a change in relative fluorescence. EC50=245 uM. (n=12); (B) illustration of attenuation of THIP-induced fluorescent changes under conditions of $GABA_A$ receptor antagonism. Concomitant representative tracings of relative fluorescence unit (RFU) changes over time evoked by addition of THIP. Lower Tracing: RFU changes following injection of DMSO vehicle (0.1%; negative control) followed by THIP (500 uM); Upper Tracing: RFU changes following injection of the GABAA receptor antagonist picrotoxin (200 uM in 0.1% DMSO) and subsequent injection of THIP (500 uM); (C) picrotoxin (picro) mediated antagonism of THIP induced changes in membrane potential at 2 different THIP concentrations (500 uM and 1 mM). (n=12 per group, * p<0.05, **p<0.01 compared to THIP alone).

THIP displayed a dose dependent enhancement of fluorescence (FIG. 3A) with an EC50 of 245 uM (n=12; 3 separate cell cultures repeated 4 times per concentration).

Figure 3B:
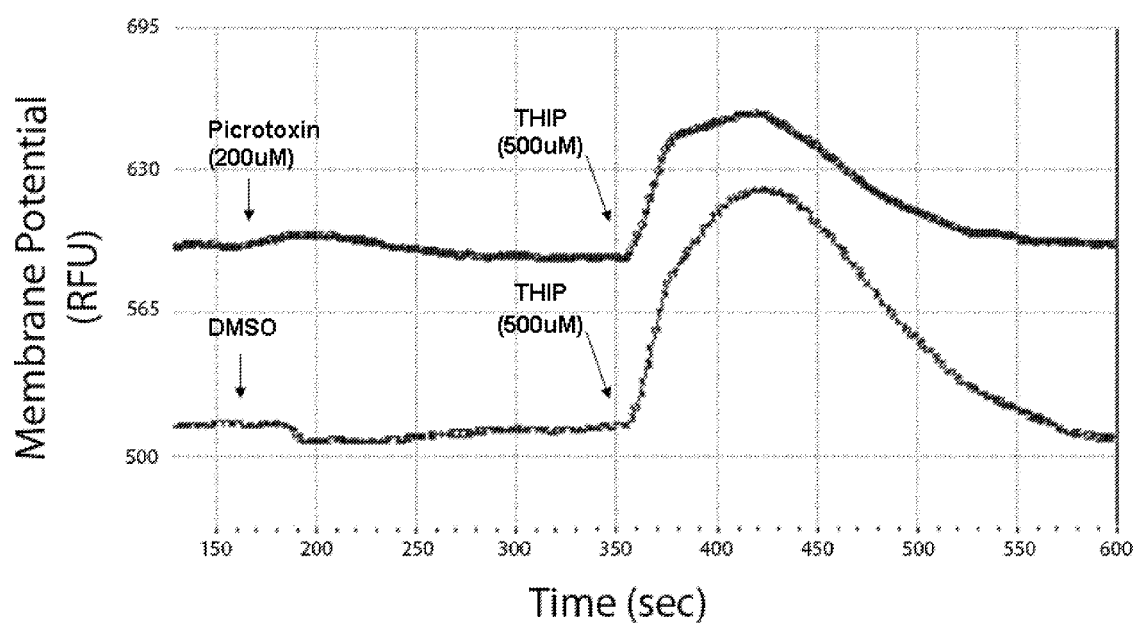
Figure 3C:
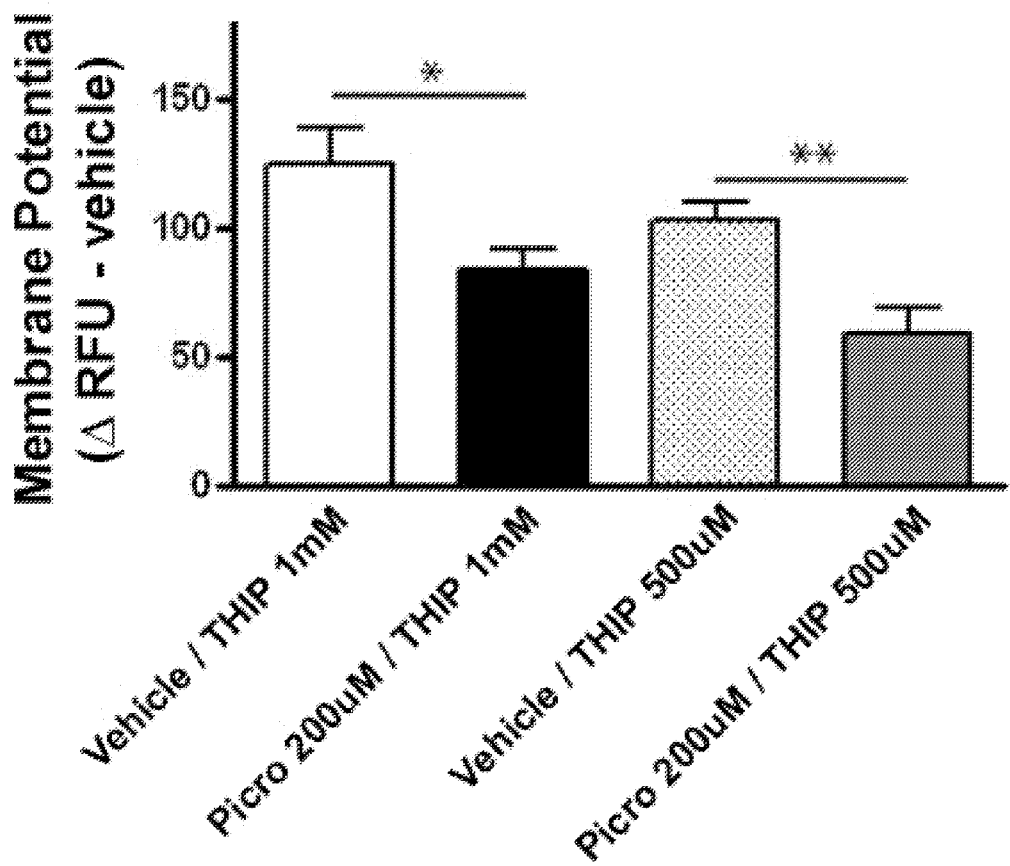

To insure these results were not attributable to any non-specific fluorescent changes produced by GABA mimetics acting directly with the dye itself, cell-free assays were performed demonstrating no effect of our drugs on fluorescence in the presence of dye alone. Since picrotoxin demonstrated no non-specific fluorescent changes, it was therefore used to antagonize THIP mediated membrane potential changes (FIG. 3B). Picrotoxin antagonism of THIP mediated membrane potential changes persisted even under conditions of high dose THIP (1 mM and 0.5 mM) in agreement with its ability to serve as a non-competitive antagonist at the GABAA receptor (FIG. 3C).

EXAMPLE 15

Electrophysiology of Human Airway Smooth Muscle Cells

To corroborate the membrane potentiometric dye findings, whether or not targeted activation of α4 containing $GABA_A$ receptors induced appropriate electrophysiologic changes was assessed. On the day of the assay, human airway smooth muscle cells (prepared as described in Reference Examples 1 and 2) were released from collagen-coated plates with collagenase type IV (Sigma C5138; 500 units/ml). The cells were resuspended in external buffer solution (In mM: NaCl 147, $MgCl_2$ 2, $CaCl_2$ 2, HEPES 10, dextrose 10; pH 7.2, osmolarity 320 mOsm) and rocked at room temperature to allow cells to obtain a spherical shape. Approximately 1 million cells were centrifuged (300×g, 3 min), washed ×2 in external buffer, and loaded (final volume of 400 uL) into a Fluxion microfluidic plate with each experimental group representing an ordered arrangement of 20 cells in parallel whole cell configuration. Following generation of adequate cellular membrane seals (40-120 MΩ), whole cell recordings were obtained under voltage clamp conditions (–80 mV) to a dose response to THIP (0.3 uM-300 uM). In separate assays cells were also co-treated simultaneously with 20 uM gabazine (GABAA receptor antagonist) and 25 uM THIP. In addition, to confirm that THIP-induced currents were due to chloride efflux, in separate experiments the intraclelualar buffer (in mM: $MgCl_2$ 4, EGTA 10, HEPES 10, CsCl 130, Mg-ATP 4, CsOH 10, pH 7.2, 290 mOsM) was modified by replacing 140 mM CsCl with 140 Cs gluconate to inhibit the magnitude of the outward current at –80 mV.

Figure 4A:
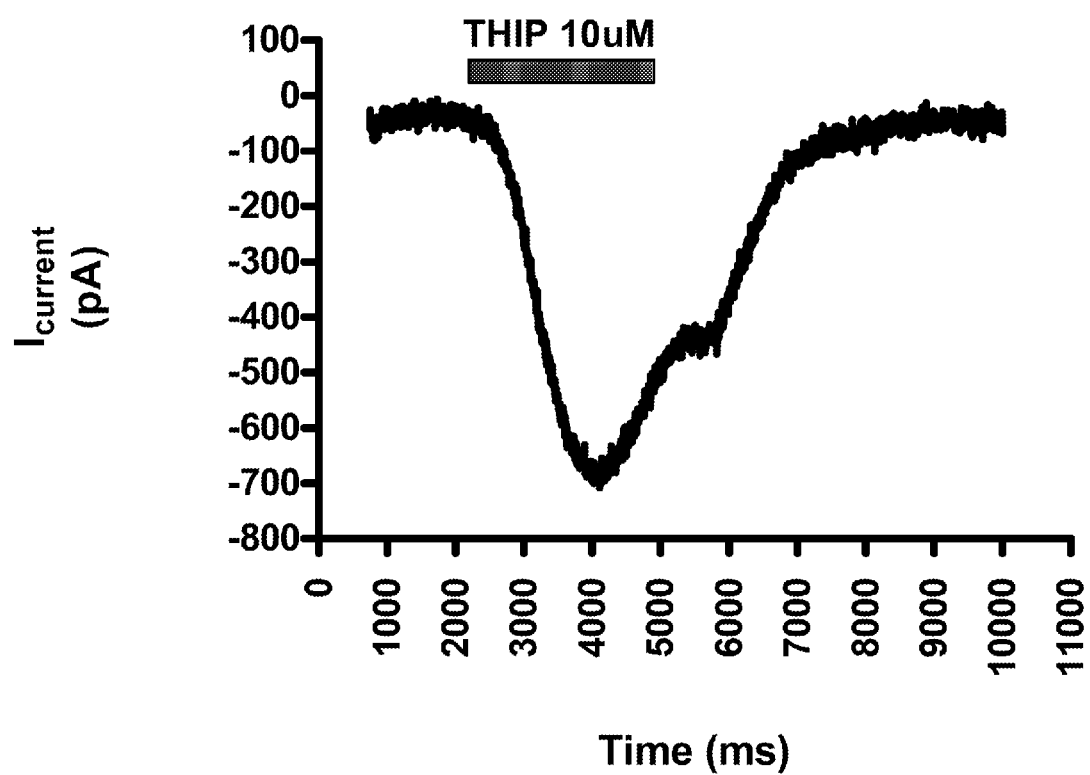
FIG. 4 shows (A) compiled and smoothed tracings (pA/ms) of evoked current from human airway smooth muscle cells following exposure to 10 uM THIP (representative of 11/12 arrays of whole cell configurations with mean current of −670.4+27.6 pA). Each array consisted of 20 human airway smooth muscle cells simultaneously held in parallel whole cell configuration on a microfluidic Fluxion™ automated patchclamp platform with a minimal seal resistance >300 Mohms; (B) dose response curve of THIP (0 to 300 uM) eliciting a current from human airway smooth muscle cells held in whole cell configuration and voltage clamped at −80 mV. EC50=15 uM. Data is obtained from 4 separate experiments; (C) gabazine or chloride free buffer attenuation of THIP induced whole cell currents. Representative tracings depicting THIP-induced currents over time for human airway smooth muscle cells held in voltage clamp at −80 mV under: control conditions (Cs Cl/THIP 25 uM), selective GABAA receptor antagonism (Gabazine/THIP 25 uM), and removal of chloride from the buffer (Cs gluconate/THIP 25 uM).
Figure 4B:
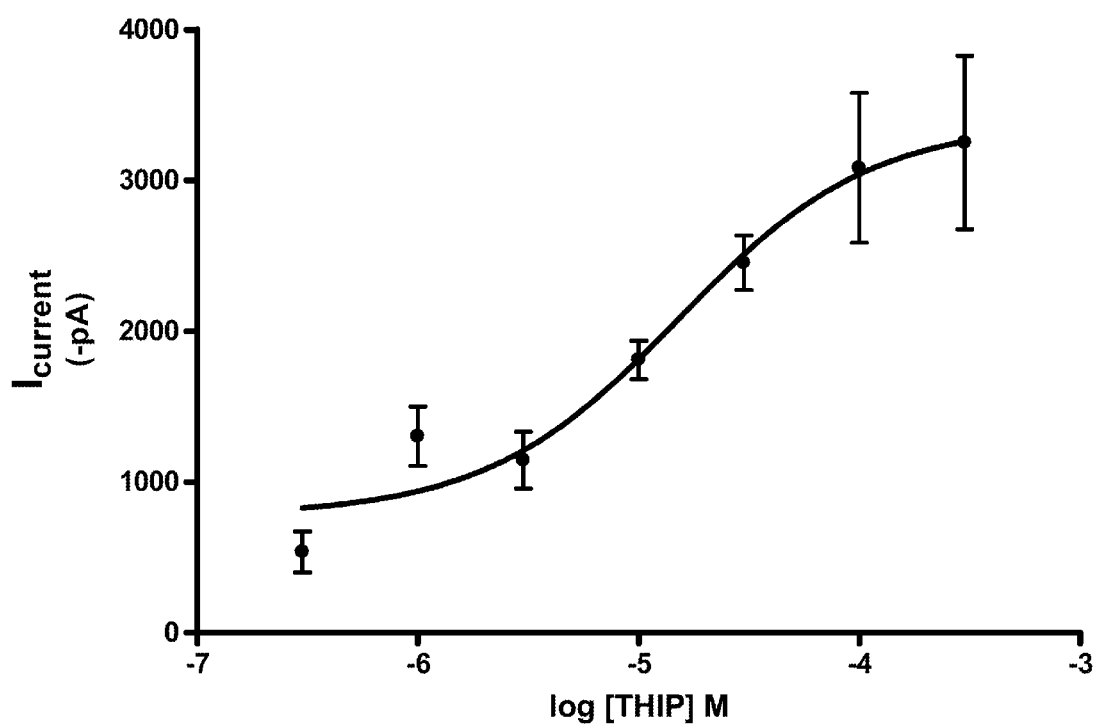

Using a microfluidic platform that allowed for 20 human airway smooth muscle cells to simultaneously achieve whole cell configuration in parallel, a robust current upon exposure to 10 uM THIP was demonstrated (FIG. 4A). In addition, utilizing graded additions of THIP (0-300 uM) an EC50 of approximately 15 uM was demonstrated for THIP (FIG. B), a finding in agreement with a mixed population of airway smooth muscle cells demonstrating heterogeneous α4/α5 $GABA_A$ receptor subunit expression. To confirm that the currents were indeed secondary to THIP-mediated activation of $GABA_A$ receptors, two experimental validations were performed. First, attenuation of the THIP-induced current (25 uM) under conditions of GABAA receptor antagonism (gabazine 25 uM) was demonstrated. Second, that following the removal of chloride from our buffer (but replacing it with equiosmotic gluconate) the ability of THIP to induce a current is lost following the removal of chloride from our buffer (but replacing it with equiosmotic gluconate) (FIG. 4C).

EXAMPLE 16

Preliminary Contractile Challenges

Following equilibration, the capsaicin analog N-vanillylnonanamide (10 µM final) was added to the organ baths prepared according to Reference Example 3 to first activate and then deplete nonadrenergic, noncholinergic (NANC) nerves. After N-vanillylnonanamide induced force had returned to baseline (~50 min), the tracheal rings were washed and then subjected to two cycles of increasing cumulative concentrations of acetylcholine (0.1 µM to 0.1 mM) to determine the EC50 concentrations of acetylcholine required for each individual ring. To avoid bias between treatment groups, tissues were contracted to individually calculated EC50's for acetylcholine and tissues with similar Emax values were randomly assigned to treatments within individual experiments. Following extensive KH buffer changes (8-9 times) tissues were allowed to stabilize at isotonic resting tension (~1.0 g). To remove confounding effects of other pro-contractile pathways each bath received a complement of antagonists 20 minutes prior to subsequent contractile challenge. The antagonists included pyrilamine (10 µM; H1 histamine receptor antagonist), and tetrodotoxin (1 µM; antagonist of endogenous neuronal-mediated cholinergic or C-fiber effects).

EXAMPLE 17

In Vitro Assessment of Two α4 Subunit Containing $GABA_A$ Receptor Selective Agonists on $β_2$-Adrenoceptor Mediated Airway Smooth Muscle Relaxation following an $EC_{50}$ Contractile Stimulus with Acetylcholine Guinea pig (GP) tracheal rings were contracted with an $EC_{50}$ concentration of acetylcholine and allowed to achieve a steady-state plateau of increased force (typically 15 min). Tracheal rings were randomly assigned to one of three groups; isoproterenol treated controls, isoproterenol dose response in the presence of an α4 $GABA_A$ selective agonist (taurine or THIP), or pretreatment with a $GABA_A$ receptor antagonist followed by isoproterenol dose response in the presence of an α4 subunit selective agonist. All groups received cumulatively increasing concentrations of isoproterenol in ½ log increments (0.1 mM to 10 µM). To determine the effect of selective $GABA_A$ activation on isoproterenol-mediated relaxation, a single dose of an α4 selective agonist (500 uM THIP or taurine 200 uM) was administered to the study group just prior to a modestly effective concentration of isoproterenol under this regimen ($10^{-8.5}$M). To confirm the effect of THIP or taurine was not attributable to non-specific effects elicited by activation of non-$GABA_A$ receptors, the third group received pretreatment with a single dose of the selective $GABA_A$ antagonist gabazine 15 min prior to contractile challenge with exogenous acetylcholine.

Figure 5A:
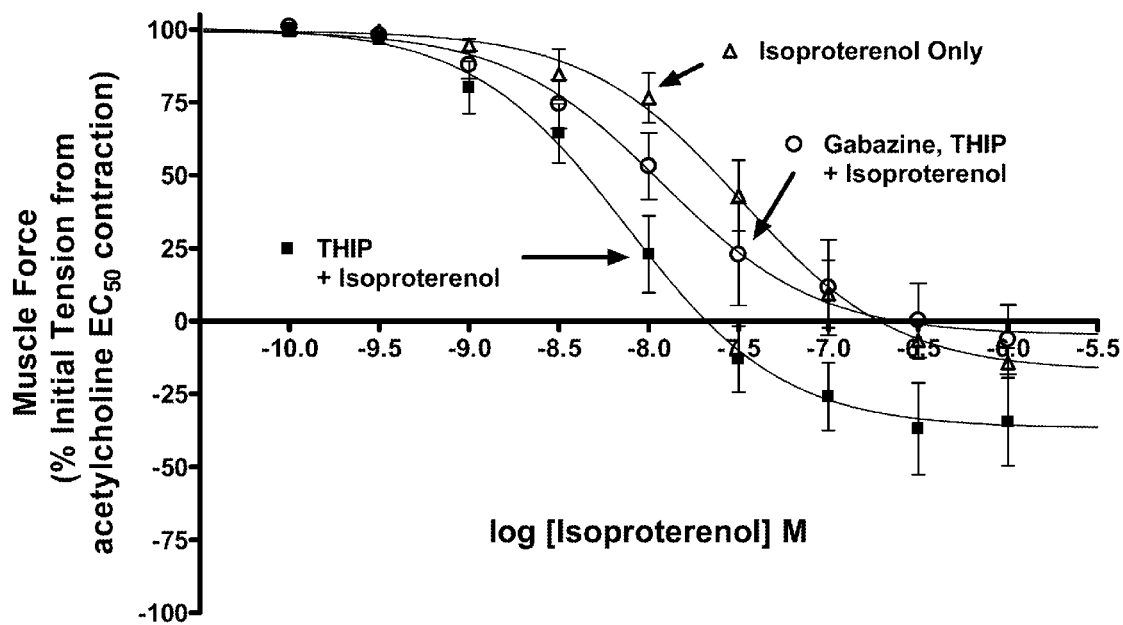
FIG. 5 shows (A) compiled isoproterenol concentration-response curves comparing treatment with isoproterenol only (EC50=32.8 mM; n=8, Δ) to isoproterenol after a single concentration of 500 uM THIP (EC50=7.6 mM; n=8, ■) and isoproterenol with a single concentration of 500 uM THIP subsequent to 500 μM gabazine pretreatment (EC50=11.8 mM; n=8, ○). Selective $GABA_A$ receptor subunit activation results in a significant several fold reduction in the EC50 for isoproterenol response and this THIP-mediated pro-relaxant effect is eliminated by $GABA_A$ receptor antagonist pretreatment; (B) THIP treatment also resulted in a significant potentiation of relaxation even at a low concentration (10 mM) of isoproterenol [muscle force=22.9±13.2% (n=8) of initial acetylcholine-induced force for THIP plus isoproterenol vs. 76.5±8.5% for isoproterenol alone (n=8); p<0.01], while pretreatment with gabazine reversed this THIP effect [muscle force=53.1±11.4% (n=8); p>0.05 compared to isoproterenol alone]. **p<0.01, n.s.=not significant.
Figure 5B:
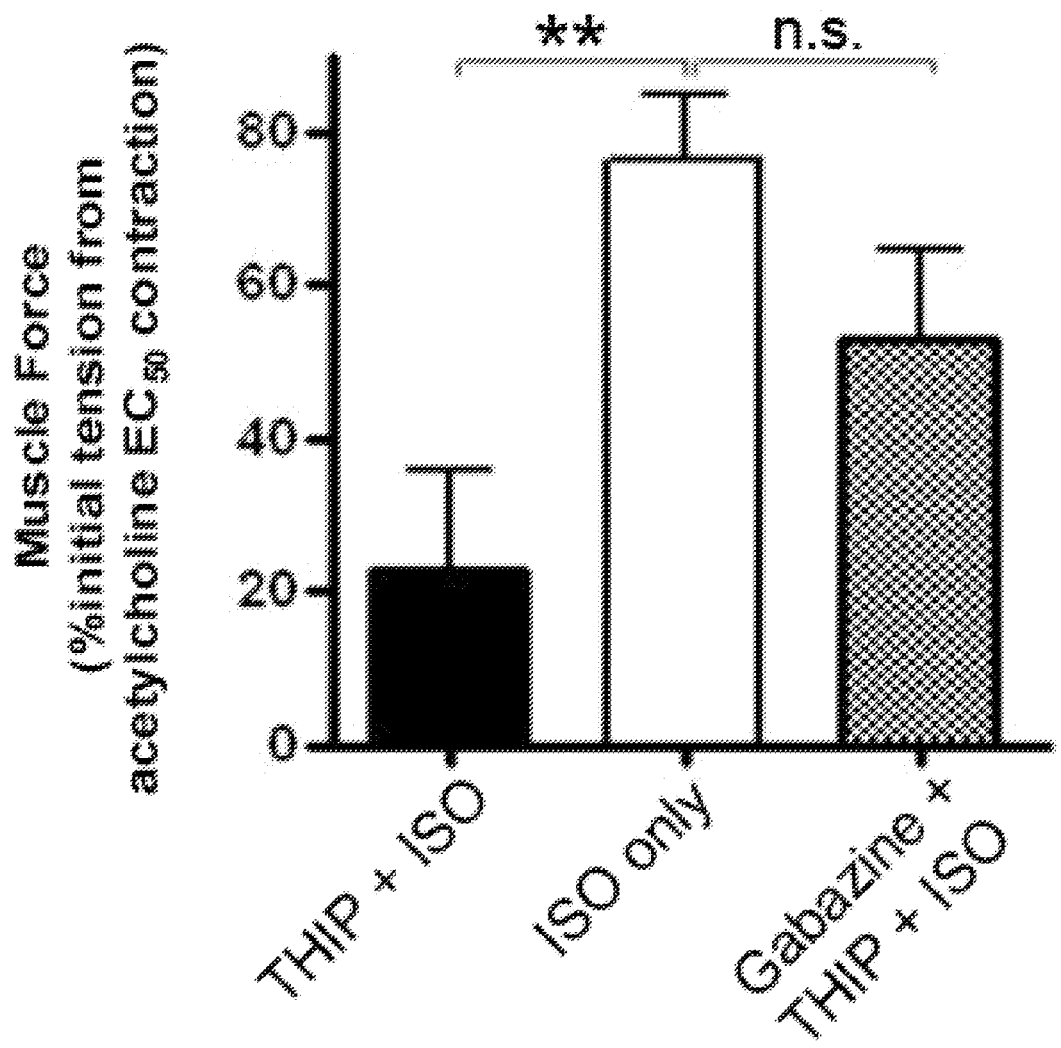

Selective α-subunit $GABA_A$ receptor activation with THIP significantly potentiated the relaxant effects of isoproterenol after an acetylcholine contraction (FIG. 5A). In guinea pig tracheal rings, co-treatment with THIP and isoproterenol resulted in a significant leftward shift in the isoproterenol relaxation concentration-response curve compared with treatment with isoproterenol alone [EC50=7.6 mM (n=8) vs. 32.8 mM (n=8); p<0.001]. To prove that the shift in EC50 observed was due to selective and specific activation of $GABA_A$ receptors, pretreatment with the selective antagonist gabazine was performed. Pretreatment with gabazine significantly reversed the THIP potentiation of isoproterenol-mediated relaxation [EC50=11.8 ±0.6 mM (n=8) vs. EC50=7.6±0.5 mM (n=8); p<0.01] after an acetylcholine contractile stimulus and significantly returned the concentration-response curve toward baseline [EC50=11.8±0.6 mM (n=8) vs 32.8 mM (n=8) respectively; p>0.05]. In addition to a significant shift in the EC50 of the isoproterenol concentration-response curve, THIP treatment also resulted in a significant potentiation of relaxation even at a low concentration (10 mM) of isoproterenol (FIG. 5B) [muscle force=22.9 ±13.2% (n=8) of initial acetylcholine-induced force for THIP plus isoproterenol vs. 76.5±8.5% for isoproterenol alone (n=8); p<0.01], while pretreatment with gabazine reversed this THIP effect [muscle force=53.1±11.4% (n=8); p>0.05 compared to isoproterenol alone]. In each case n represents total number of individual rings in a treatment group.

Figure 6:
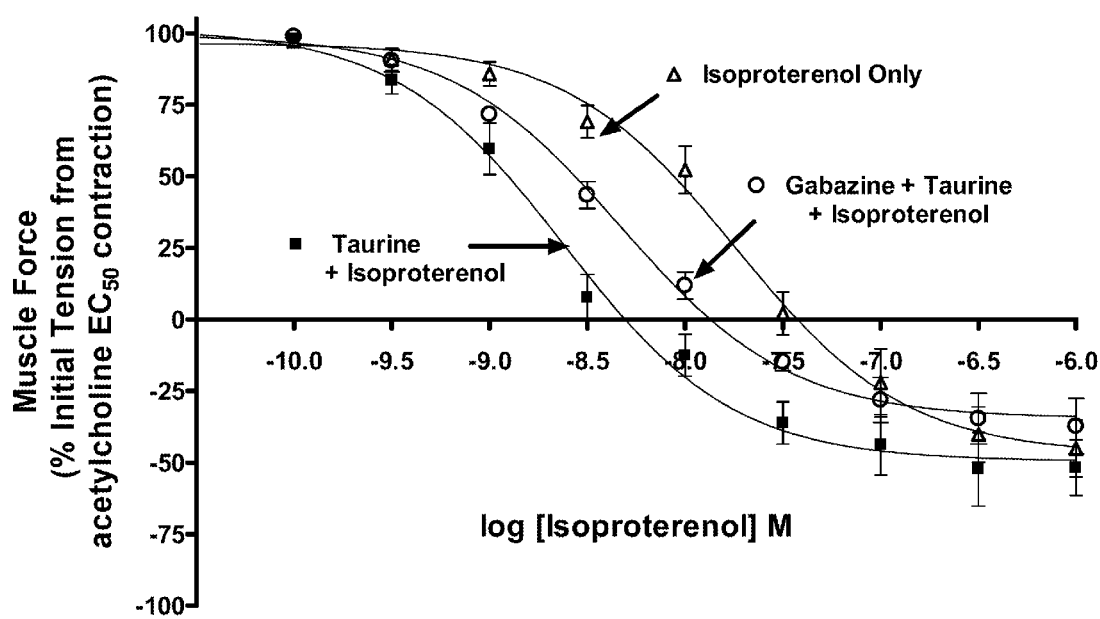
FIG. 6 shows compiled isoproterenol concentration-response curves comparing treatment with isoproterenol only (EC50=15.8 mM (n=6), Δ) to isoproterenol after a single concentration of 200 uM taurine (EC50=2.4 mM (n=7), ■) and isoproterenol with a single concentration of 200 uM taurine subsequent to 200 μM gabazine pretreatment (EC50=4.7 mM (n=7), ○). Taurine treatment results in a several fold reduction in the EC50 for isoproterenol response, and this pro-relaxant effect is significantly but partially reversed (p<0.05 respectively) by GABAA receptor antagonist pretreatment.

Utilizing the same paradigm outlined with THIP above, it was found that taurine (200 uM) potentiated isoproterenol-mediated relaxation of acetylcholine pre-contracted airway smooth muscle (FIG. 6). Co-treatment with taurine and isoproterenol resulted in a significant leftward shift in the isoproterenol relaxation concentration-response curve compared with treatment with isoproterenol alone [EC50=2.4 mM (n=7) vs. 15.8 mM (n=6), respectively; p<0.01]. To demonstrate that α4 containing $GABA_A$ receptor activation is an important component of taurine's effect, the $GABA_A$ selective antagonist gabazine (200 uM) was used in this experimental permutation to block taurine's effect. As seen with the THIP studies, pretreatment with gabazine significantly reversed the potentiation of isoproterenol-mediated relaxation provided by taurine [EC50=4.7 mM (n=7) vs 2.4 mM (n=7); p<0.05]. However in agreement with a partial role of $GABA_A$ receptor activation in taurine mediated relaxation, gabazine did not completely reverse the relaxation afforded by taurine treatment [EC50=4.7 mM (n=7) vs 15.8 mM (n=6); p<0.05]. Each n represents the total number of individual rings in a treatment group.

EXAMPLE 18

In Vitro Assessment of a Novel 8-methoxy imidazobenzodiazepine (13) (CM-D-45; a Third α4 Subunit Containing $GABA_A$ Receptor Selective Agonist) to Directly Relax Airway Smooth Muscle Following Either a tetraethylammonium chloride (TEA) or Substance P Mediated Contraction To determine the direct relaxant effect of α4 subunit containing $GABA_A$ receptor activation using different contractile agonists, GP tracheal rings prepared according to Reference Example 3 were contracted with a single dose (10 mM) of TEA or (1 uM) substance P. Following a plateau in the generated muscle force, a single dose of CM-D-45 (200 um) or vehicle control (DMSO 0.1%) was added to the organ bath buffer and the percentage of relaxation achieved was assessed over 15 minutes in comparison to intra-experimental matched vehicle controls.

Figure 7A:
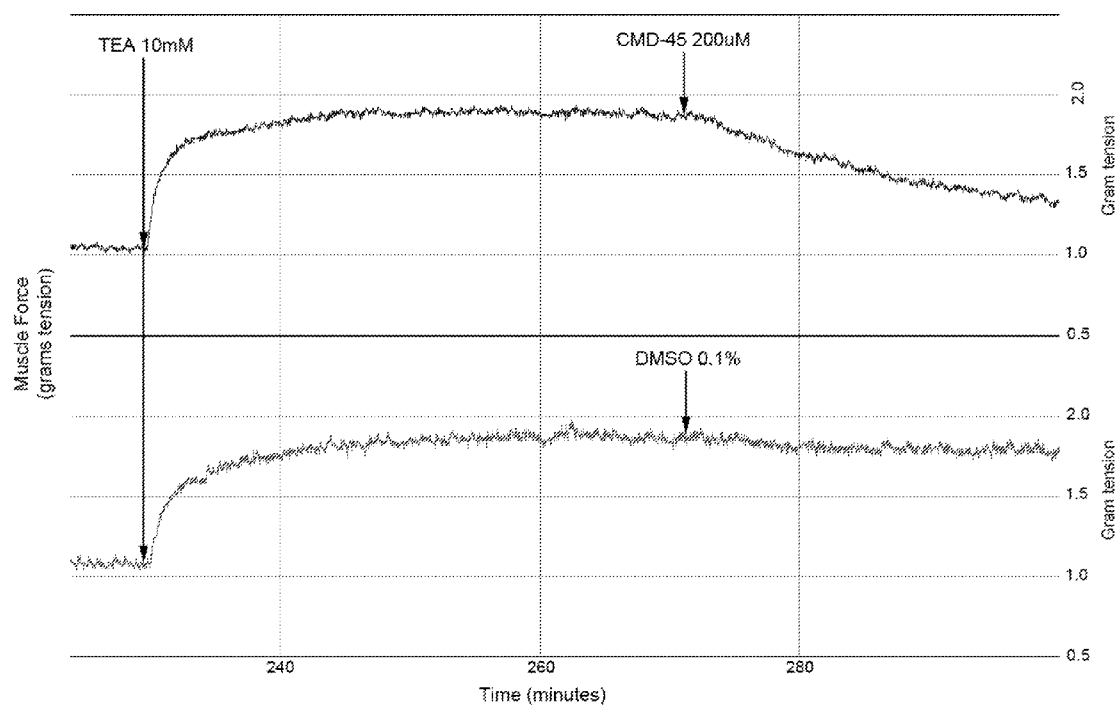
FIG. 7 shows (A) representative tracings (in muscle force/time) illustrating direct relaxation achieved by CM-D-45 following a contraction achieved by 10 mM TEA (upper tracing) compared to 0.1% DMSO vehicle control (lower tracing); (B) CM-D-45 induces a significant degree of spontaneous relaxation following a 10 mM TEA mediated contraction compared to treatment with 0.1% DMSO vehicle control at 15 minutes following drug addition. [muscle force=54.3±14.3% (n=13) of initial TEA-induced force following CM-D-45 treatment vs. 99.1±9.5% for vehicle control alone (n=13); **=p<0.0001]; (C) CM-D-45 also induces significant spontaneous relaxation following a 1 uM substance P mediated contraction compared to treatment with 0.1% DMSO vehicle control at 15 minutes following drug addition. [muscle force=61.3±16.9% (n=10) of initial TEA-induced force following CM-D-45 treatment vs. 89.5±5.3% for vehicle control alone (n=10); *=p<0.001].
Figure 7B:
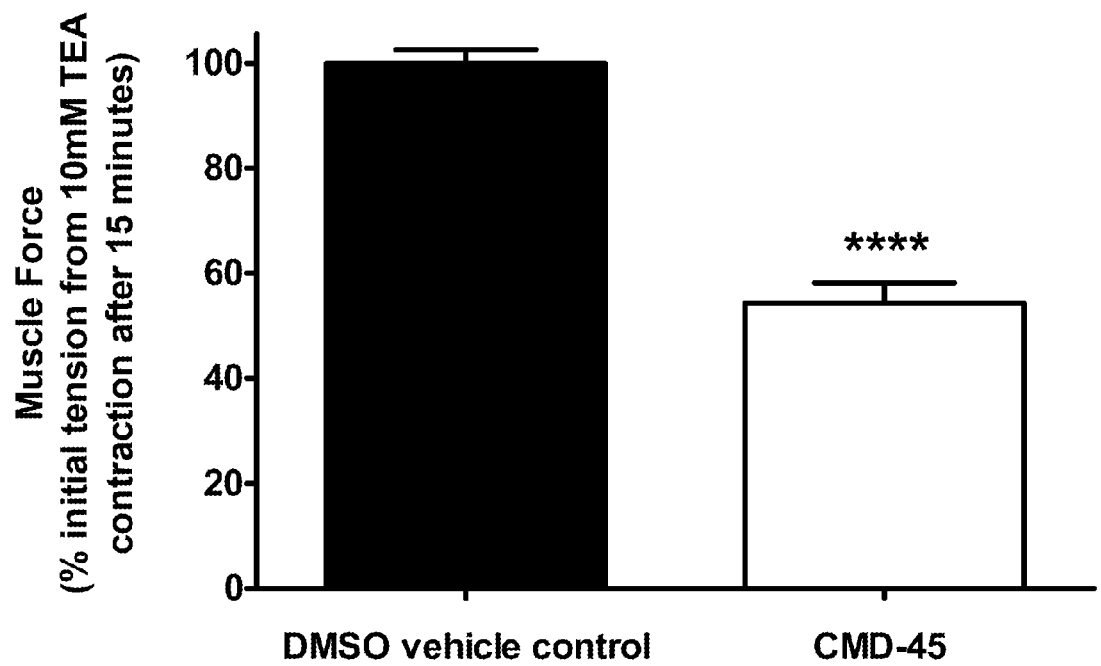
Figure 7C:
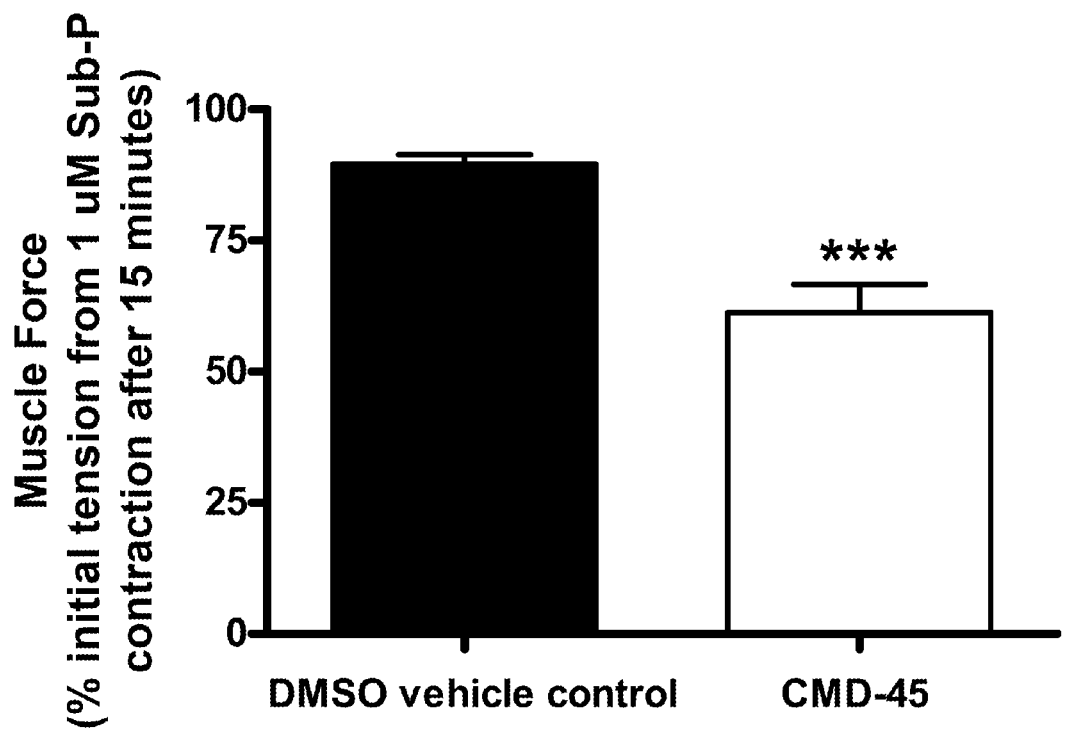

Following a plateau in the force generated by TEA (10 mM), addition of 200 uM CM-D-45 resulted in direct relaxation compared to matched DMSO (vehicle) treated controls (FIG. 7A). Treatment of TEA-precontracted airway smooth muscle with CM-D-45 resulted in a significant decrease in initial muscle force (reported as % gram tension remaining from pre-treatment levels) over 15 minutes (54.3% +14.3; n=14) compared to DMSO 0.1% treated tissues (99.9% +9.5; n=13; p<0.0001). Similar results were achieved following challenge with a neurokinin receptor-mediated airway smooth muscle contraction using substance P. As before, CM-D-45 treatment induced a significant direct relaxation of precontracted airway smooth muscle (61.3% +5.3; n=10) compared to matched vehicle controls (89.52% +1.9; n=8; p<0.001) illustrating that this effect is not limited to a specific contractile agent. Each n represents the total number of individual rings in a treatment group.

EXAMPLE 19

Airway Smooth Muscle Contraction in Mouse Ex Vivo Tracheal Rings

Figure 8:
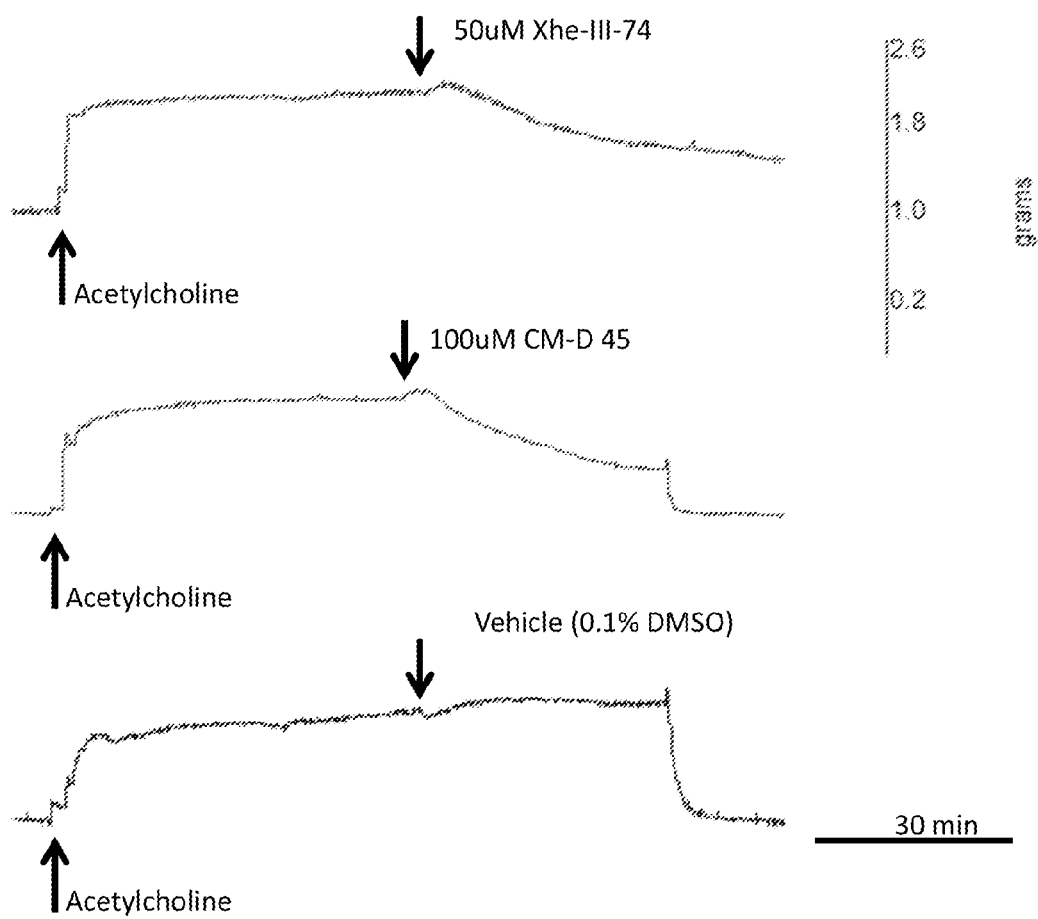
FIG. 8 shows airway smooth muscle force in mouse ex vivo tracheal rings.
Figure 9:
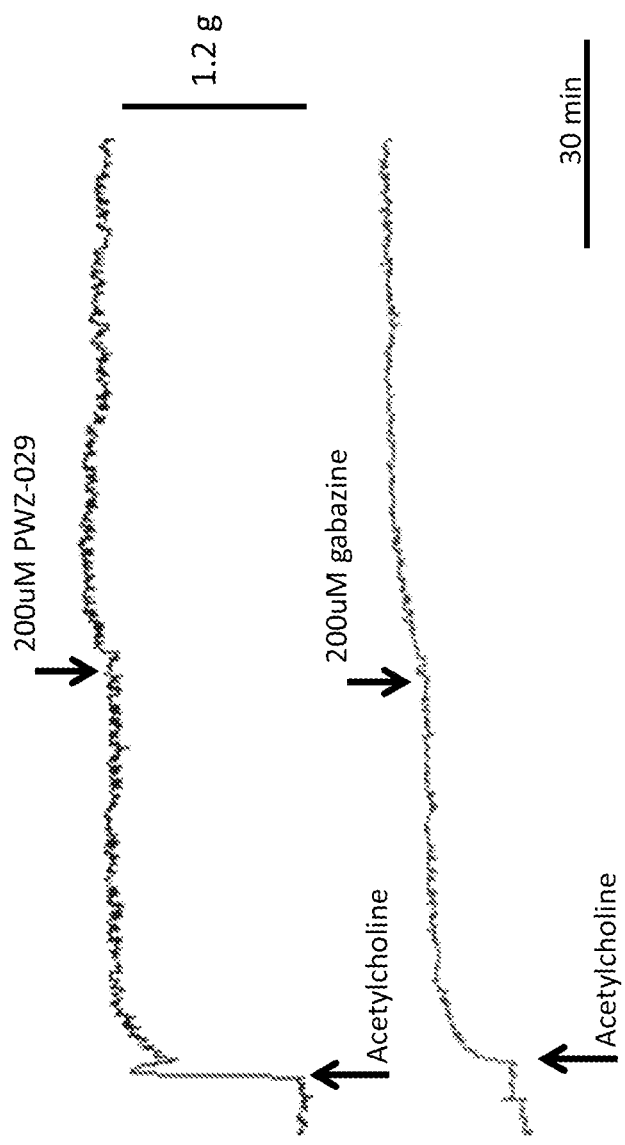
FIG. 9 shows airway smooth muscle force in guinea pig ex vivo tracheal rings.
Figure 10A:
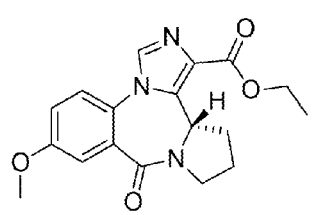
FIGS. 10A and 10B show various compounds according to the present invention.
Figure 10A:
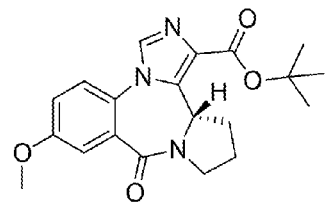
Figure 10A:
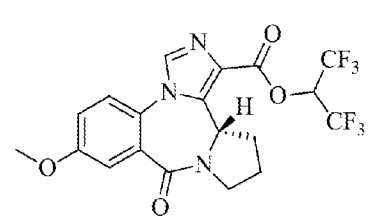
Figure 10A:
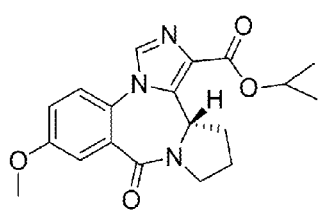
Figure 10A:
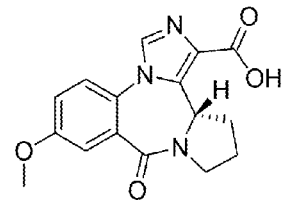
Figure 10A:
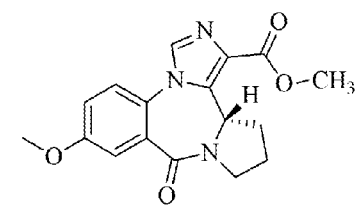
Figure 10A:
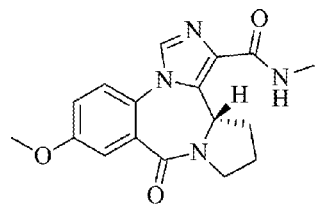
Figure 10A:
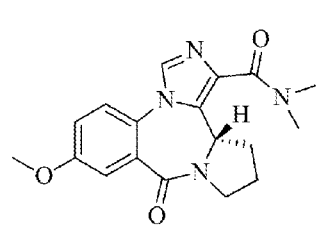
Figure 10A:
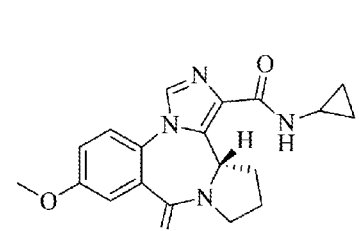
Figure 10A:
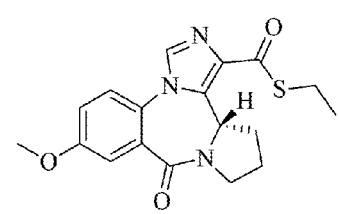
Figure 10B:
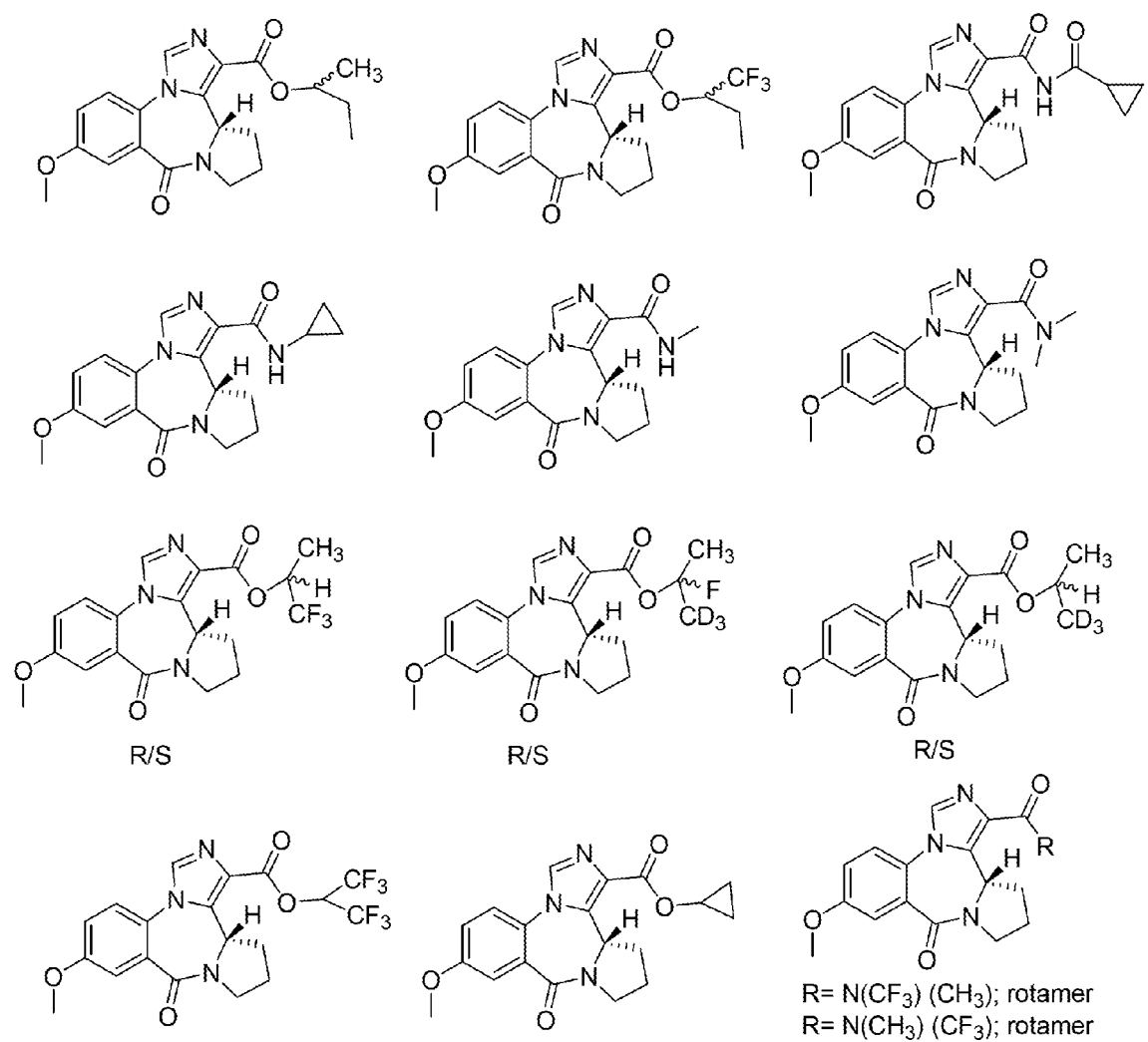
Figure 11A:
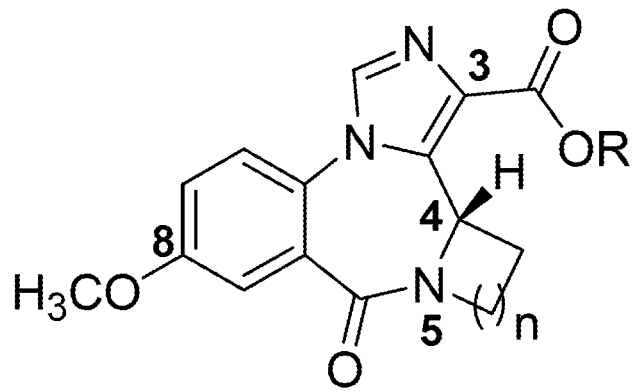
FIGS. 11A, 11B and 11C show various compounds according to the present invention.
Figure 11B:
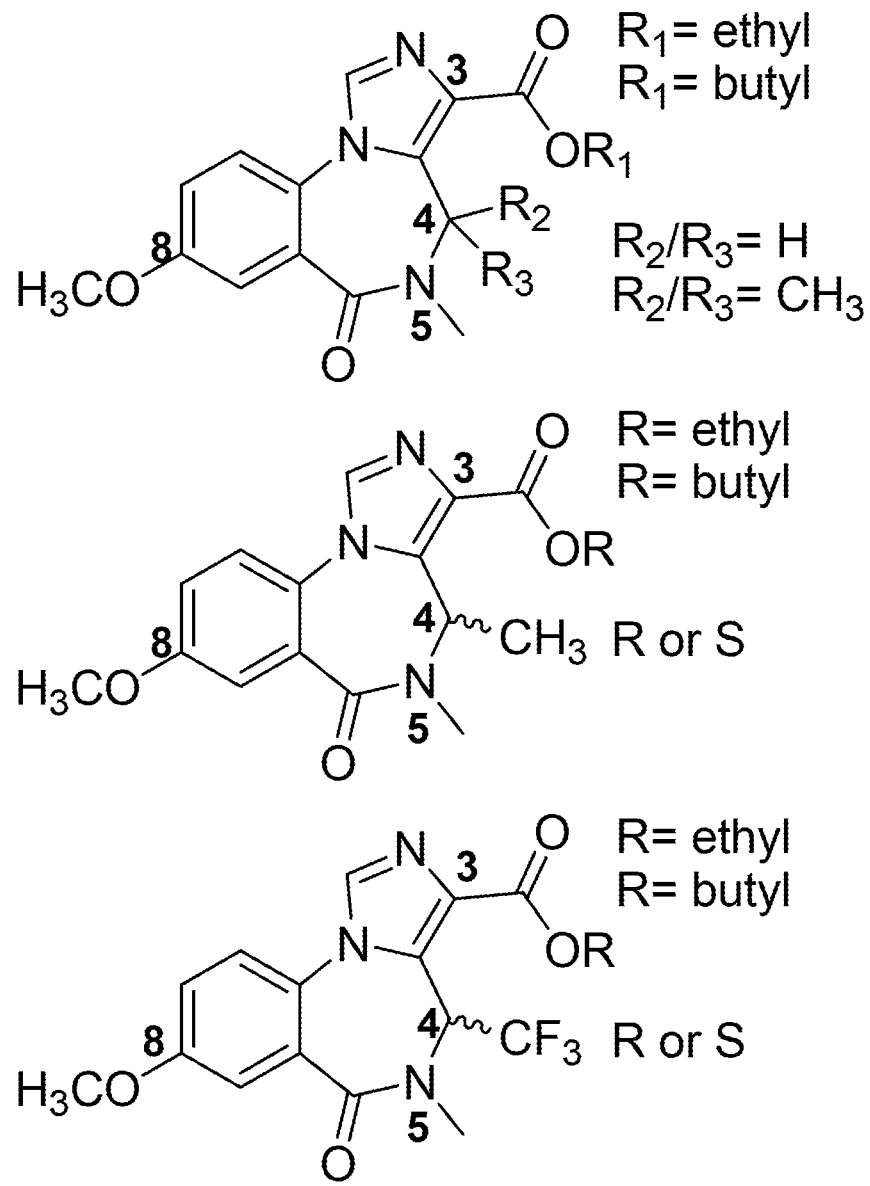
Figure 11C:
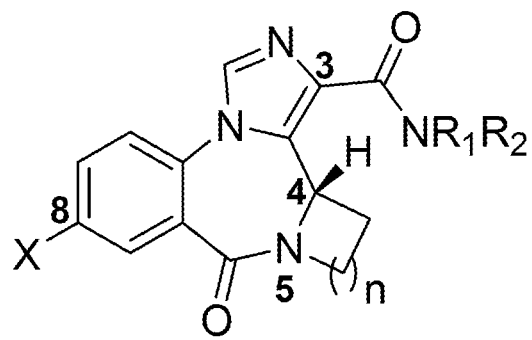
Figure 11C:
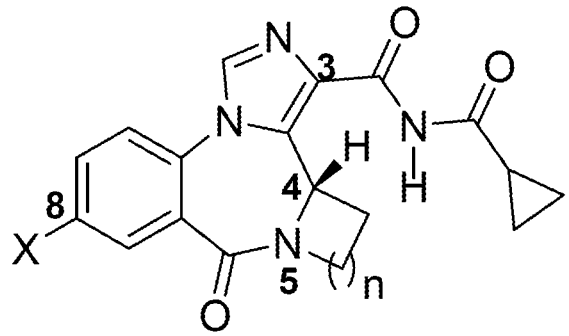
Figure 11C:
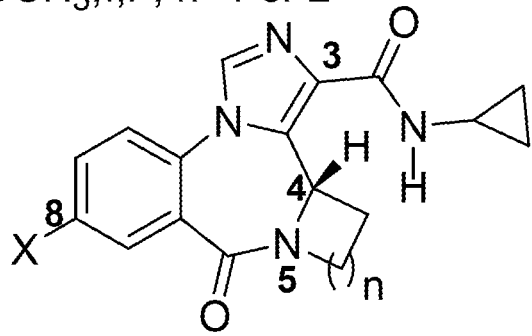

All animal care protocols were approved by the Columbia University Institutional Animal Care and Use Committee (IACUC). C57 wild type or C57 mice (male, ~20 g) genetically deficient in the $GABA_A$ α4 subunit were anesthetized with 100 mg/kg pentobarbital. Trachea were removed and divided in half but left as a closed ring and suspended in a physiological buffer solution at 4° C. Closed tracheal rings were suspended in a myograph (DMT®) under 0.5 g resting tension at 37° C. with bubbled oxygenation 95% $O_2$/5% $CO_2$ and allowed to equilibrate for 1 h at resting tension with buffer exchanges every 15 min. Continuous digital recording of airway smooth muscle contractile force was done with Biopac hardware connected to Acknowledge v 7.3.3 software. Preliminary contractile challenges with performed with acetylcholine dose responses (0.1 mM-100 uM) 3 times with buffer exchanges and resetting of resting tension between each dose response. The mouse tracheal rings were contracted with acetylcholine (an $EC_{50}$ concentration for each ring). Following stabilization of the contractile force, the $GABA_A$ α4/α6 selective subunit agonists or their vehicle were applied. Relaxation was measured as the percent of remaining contractile force at various time points after the addition of the $GABA_A$ α4 ligands or the vehicle control (0.1% DMSO). The 50 uM Xhe-III-74 results in a similar magnitude of relaxation as that afforded by 100 uM CM-D 45. (See FIG. 8).

EXAMPLE 20

Airway Smooth Muscle Force in Guinea Pig Ex Vivo Tracheal Rings

Male (400 g) Dunkin Hartley guinea pigs were anesthetized with 100 mg/kg pentobarbital. Trachea were removed and divided into 8 closed circular rings each comprised of 2 cartilagenous segments. Adventitia and epithelium were dissected off under a microscope. Closed rings were suspended in 2 ml Radnoti organ baths connected to a Grass FT03 force transducer under 1 g resting tension at 37° C. with bubbled oxygenation 95% $O_2$/5% $CO_2$ and allowed to equilibrate for 1 h at resting tension with buffer exchanges every 15 min. Continuous digital recording of airway smooth muscle contractile force was done with Biopac hardware connected to Acknowledge v 7.3.3 software. Preliminary contractile challenges with performed with acetylcholine dose responses (0.1 nM-100 uM) 3 times with buffer exchanges and resetting of resting tension between each dose response. The Guinea pig tracheal rings were contracted with acetylcholine (an EC50 concentration for each ring). Following stabilization of the contractile force, the $GABA_A$ α5 selective negative modulator or the $GABA_A$ non-selective antagonist gabazine was added to the buffer. The increase in force demonstrated by PWZ-029 indicate a role for the $GABA_A$ receptors containing the α5 subunit in the tonic maintenance of airway

EXAMPLE 21

Human Airway Smooth Muscle Study

In accordance with Columbia University's IRB, discarded regions of healthy human donor lungs will be employed in our studies (deemed not human subjects research under 45 CFR 46). Upon availability, epithelial layer will be dissected from the underlying muscle layer and immediately processed for organ bath studies. In functional organ bath studies, intact airway smooth muscle strips from trachea or first generation bronchi (including small adjoining segments of the cartilaginous ring) are used rather than intact rings. Briefly, tissues are attached inferiorly to a fixed hook and superiorly to a Grass FT03 force transducer (Grass Telefactor, West Warwick, R.I.) such that muscle contraction align in the vertical plane between the anchoring hook below and transducer above to give continuous digital recordings of muscle force over time. Tissues undergo preliminary contractile challenges with either TEA or acetylcholine (at EC50). Human airway smooth muscle strips are then contracted with a classic contractile mediator (acetylcholine, histamine, leukotriene D4, substance P, KCl or TEA) and following the establishment of a stable contraction test compounds (novel GABAAR agonists and controls (vehicle, gabazine, muscimol)) are then applied to determine the prorelaxant effects during maintenance of contraction. Subsequent changes in ASM force are then measured 15 min after treatment and expressed as the percent of change in muscle force elicited from the plateau achieved by the induced contraction. A two-tailed Student t-test is employed and data presented as means±SE; $P<0.05$ are considered significant.

EXAMPLE 22

Allergen-Induced Asthma Model

Compound efficacy will be evaluated in an acute OVA challenge model in compliance with protocols approved by the IACUC at UW-Milwaukee. BALB/c mice will remain naïve (control) or challenged with OVA (10 µg i.p. in alum) on days 0 and 7, followed by aerosol OVA challenge (1% solution) on days 14 and 16. At least 2 doses of test compound (or vehicle control) will be administered i.p. to groups of 10 mice each on days 13-17. Maximum starting doses of test compound will be predetermined from pilot step-wise "no observable adverse effect level" (NOAEL) studies in normal mice (observations will include changes in weight, respiration, lethargy, CNS signs, and gastrointestinal distress; brains will be harvested at the NOAEL for compound quantification by LC-MS (80). Longitudinal AHR measurements will be made on days 0, 13, and 17 upon exposure to nebulized vehicle (PBS) or doubling concentrations of methacholine (0.625-10 mg/ml) using the Buxco dual chamber airway mechanics (NAM) system (Buxco, Sharon, Conn.), following manufacturer's instructions. Specific airway resistance (sRAW) will be calculated using FinePointe software. After the final AHR measurement, mice will be euthanized, blood collected, and bronchoalveolar lavage (BAL) fluid collected (with 1 ml PBS); lungs then removed and lobes separated. Formalin fixed paraffin sections will be prepared from one lobe (including large and small airways) and processed for standard H&E (for general histolopathology and inflammation) and PAS (for mucous cell; as cells/mm of basement membrane) staining Other sections will be processed for immunohistochemical staining with monoclonal antibodies to α-smooth muscle actin (Abcam) or MUC5AC (Abcam) and fluorescent-labeled rabbit anti-mouse IgG (Life Technologies). To assay ASM hyperplasia, mice will be will be given an i.p. injection of 100 µg 5-ethynyl-2'-deoxyuridine (EdU; Invitrogen) 96 hr. prior to euthanasia. EdU is an alkyne thymidine analog and incorporates into DNA during active synthesis. EdU incorporation (stained nuclei) will be detected by treating paraffin lung sections with azide-fluorophore (Alexa Fluor 594; Invitrogen) followed by fluorescent microscopy. All histological preparations will be blinded for microscopy and scoring. Lung homogenates and sera of the other lobe will be assayed for cytokine profiles and OVA specific IgE (82), respectively. Cytokines will be assayed using a multiplex immune assay system (Bio-Plex™; Bio-Rad; initially a panel of 23 cytokines representing a wide range of Th1/Th2/Th17 cytokines will be used, but the panel may be later reduced based on experimental results to economize). BALF cells will also be counted as described (83). Where appropriate, a two-tailed paired Student's t-test or the Mann-Whitney nonparametric test will be used to determine statistical significance at $p<0.05$.

EXAMPLE 23

Virus-Induced Asthma Model

Efficacy of $GABA_4R$ compounds in chronic lung disease will be studied in a virus induced asthma model. C57BL/6 mice (at 6-20 weeks of age; groups of 10) will be inoculated intranasally with 2×105 pfu SeV (Strain 52; ATCC) or UV-inactivated SeV (UV-SeV) (69), at day 0. Mice are monitored daily for weight and activity; with chronic disease being well established by day 49 post-inoculation (P-I). Four experimental groups will be arranged, with test compound (or vehicle) administered i.p. during days 49-56 P-I. For prophylactic studies, treatment would be administered during days 13-21, followed by disease measurement at days 49-56; to model a dosing regimen that corresponds to childhood treatment following RSV exposure (thus, investigating if immune modulation early after viral infection or during the acute post-infection phase can influence development of later inflammatory lung disease). Serial noninvasive AHR measurements (sRAW) in response to methacholine will be measured in all Groups on days 13, 49, and 56 PI. Following AHR measurements on day 56, animals will be euthanized and BALF, blood, and tissue samples will obtained. BALF will be collected in 1 ml PBS, centrifuged, and the cell supernatants collected for cytokine analysis as above. The cell pellet will be resuspended in RPMI and samples taken for differential cell counts (Diff-Quik) and flow cytometry. For flow cytometry, cell preparations will be stained with fluorophore labeled monoclonal antibodies to mouse CD1d (Invitrogen) and Mac-3 (BD) for M2 macrophages or CD3 and NK1.1 (both Invitrogen) for NKT cells. Antibody labeled cells will be examined with a FACS Calibur instrument (BD Biosciences) and data analyzed with FlowJo software (Tree Star, Ashland, Oreg.) (69, 70, 84). All other lung tissue and biochemical testing will be performed and data analyzed as in the OVA model.

EXAMPLE 24

COPD Model

Efficacy of GABAAR compounds will be studied by LPS lung challenge in mice as a model of human COPD. LPS is a proinflammatory stimulant that is present as a contaminant in cigarette smoke, air pollution, and organic dusts. In humans, chronic exposure to LPS-laden dusts results in decreased lung function. In the acute model, LPS induces a mixed inflammatory reaction with increases in neutrophils and increased tumor necrosis factor (TNF), IL-1, and other mediators in brochoalveolar fluid. Prior to administration, each test compound is diluted in a buffer solution vehicle (phosphate buffered saline, pH 7.4) and filter sterilized. Test compound is administered i.p. in a total volume of 100 ul, in each of the indicated days (thus 3 doses). Approximately one hour after the final i.p. compound administration, mice receive LPS intratracheally using a non-surgical procedure. Mice are first anesthetized by subcutaneous (s.c.) injection with ketamine hydrochloride and xylazine hydrochloride solution (Cat. no. K113; Sigma; 50 mg/kg ketamine HCl). LPS (Cat. no. L2880; Sigma, type 055:B5), dissolved in 50 µL sterile 0.9% NaCl, is instilled intratracheally (i.t.) (20 µg LPS/mouse) via a cannula and syringe (2×25 µl), followed by 100 µl air. Sham-treated mice are instilled i.t. with 50 µL sterile 0.9% NaCl. After i.t. treatment, mice are kept in an upright position for 10 min to allow the fluid to spread throughout the lungs. Mice are allowed to recover from anesthesia and the sacrificed 24 h after using cervical CO2 asphyxiation. Blood is collected via heart puncture in EDTA-containing tubes, immediately centrifuged (2000×g, 10 min, 4° C.) and plasma was stored at −80° C. Lungs tissue is removed and snap-frozen for RNA-isolation and MPO analysis. For immunohistochemical analyses lung tissue is placed in 10% phosphate-buffered formalin (pH 7.4).

EXAMPLE 25

Immune Arthritis Model

Groups of 8-10 male DBA/1j mice (Jackson Laboratories, Bar Harbor, Me., USA) 8-10 weeks of age are immunized with 200 mg bovine collagen II (bCII, Chondrex, Redmond, Wash., USA) in 50% complete Freund's adjuvant intradermally at the base of the tail. Mice are similarly boosted 21 days later with 100 mg of bCII in incomplete Freund's adjuvant. Groups of control mice are treated with sham immunizations without bCII. Food and water consumption, body weights, as well as clinically observable joint inflammation are measured throughout the treatment course. Beginning after the initial immunization, mice are administered GABAA receptor agents of the instant invention 3 times per week for 8 weeks. Compound dosing will be determined as described in Example 22. Serum collagen-specific IgG, IgG1, and IgG2a antibodies in individual control and experimental mice 8 weeks after the final immunization are characterized by microtiter plate ELISA. In the ELISA bCII is used as antigen for coating the plate wells and isotype-specific, fluorophore-conjugated rabbit anti-mouse antibodies are used to quantify primary antibody binding. Wells in the ELISA plates are read using a standard fluorescent plate reader. Compound efficacy will be evidenced by reduction of clinical joint inflammation and/or reduction in IgG antibody titers to bCII in the treated in comparison to control mice.

EXAMPLE 26

Autoimmune Diabetes Model

Non-obese diabetic (NOD) have been used for 30 years in the study of diabetes. NOD mice are characterized by insulitis, a leukocytic infiltrate of the pancreatic islets. Decreases in pancreatic insulin content occur spontaneously in females at about 12 weeks of age and several weeks later in males. Diabetic mice are hypoinsulinemic and hyperglucagonemic, indicating a selective destruction of pancreatic islet beta cells. Compounds of the instant invention are dosed QD or BID for 28 days via one of the route of administration (PO, IP, IM, SC); control animals are similarly given vehicle doses. Doses are determined as described in Example 22. 8-10 mice are assigned per group. Animals are monitored twice per week for body weight, food consumption, water intake, and blood or urine glucose, are measured. Urine glucose can be determined using commonly available test strips (Bayer Diastix). Efficacy of compounds is evidenced by reduction in one or more of these clinical markers in the treated versus the control groups.

All patents, publications and references cited herein are hereby fully incorporated by reference. In case of conflict between the present disclosure and incorporated patents, publications and references, the present disclosure should control.

What is claimed is:
1. A compound according to formula (I):

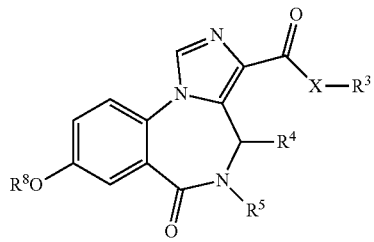

or a stereoisomer or pharmaceutically acceptable salt thereof,
wherein
$R^3$ is
$X$ is —O—;
$R^4$ is selected from $C_{1-4}$ alkyl;
$R^5$ is selected from H or $C_{1-4}$ alkyl;
or $R^4$ and $R^5$ together form a 4- or 5-membered heterocyclic ring which is saturated or unsaturated; wherein the ring contains from 1-3 heteroatoms selected from O, N, S, Si, and P; and
$R^8$ is $C_{1-4}$ alkyl or $C_{3-4}$ cycloalkyl;
with the proviso that $R^8$ is not $CH_3$ when $R_4$ and $R_5$ are a $C_{2-3}$ alkylene chain and form a 4- or 5- membered ring.

2. The compound according to claim 1, or a pharmaceutically acceptable salt thereof, wherein $R^4$ and $R^5$ form the 4- or 5-membered heterocyclic ring.

3. The compound according to claim 2, or a pharmaceutically acceptable salt thereof, wherein the ring contains 2-3 heteroatoms.

4. The compound according to claim 2, or a pharmaceutically acceptable salt thereof, wherein the ring has 5 member atoms.

5. The compound according to claim 1, or a pharmaceutically acceptable salt thereof, wherein $R^3$ contains at least one deuterium ($^2$H) in place of a hydrogen.

6. The compound according to claim 1, or a pharmaceutically acceptable salt whereof, wherein $R^8$ contains at least one deuterium ($^2$H) in place of a hydrogen.

7. The compound according to claim 1, or a pharmaceutically acceptable salt thereof, wherein the compound is a compound of formula (IIA) or (IIB):

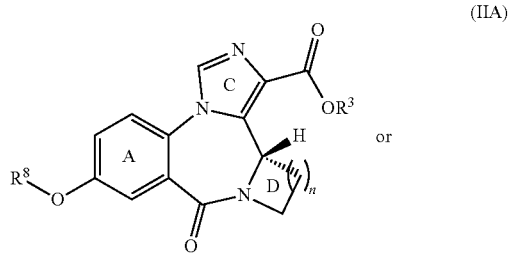

or

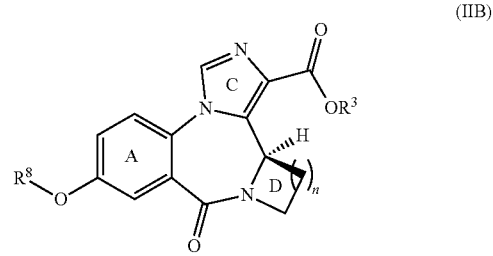

wherein $R^8$ is $-CD_3$, ethyl t-butyl or cyclopropyl;

$R^3$ is H; and n is 1 or 2.

8. A pharmaceutical composition comprising a compound according to claim 1, or a pharmaceutically acceptable salt thereof, and a pharmaceutically acceptable carrier.

9. A method of reducing airway constriction comprising administering to a subject in need thereof an effective amount of the compound of claim 1, or a pharmaceutically acceptable salt thereof.

10. A method of reducing lung inflammation comprising administering to a subject in need thereof an effective amount of the compound of claim 1, or a pharmaceutically acceptable salt thereof.

* * * * *

UNITED STATES PATENT AND TRADEMARK OFFICE
CERTIFICATE OF CORRECTION

PATENT NO. : 9,879,020 B2
APPLICATION NO. : 14/429808
DATED : January 30, 2018
INVENTOR(S) : Douglas C. Stafford et al.

It is certified that error appears in the above-identified patent and that said Letters Patent is hereby corrected as shown below:

In the Claims

Column 40, Claim 1, Line 18: replace "$R^3$ is" with --$R^3$ is H;--

Signed and Sealed this
Twenty-ninth Day of May, 2018

Andrei Iancu
*Director of the United States Patent and Trademark Office*